(12) United States Patent
Iljima et al.

(10) Patent No.: US 8,866,134 B2
(45) Date of Patent: Oct. 21, 2014

(54) LIGHT-EMITTING DEVICE AND PHOTOVOLTAIC CELL, AND METHOD FOR MANUFACTURING THE SAME

(75) Inventors: Takayuki Iljima, Tsukuba (JP); Kenta Tanaka, Tsukuba (JP); Masanobu Tanaka, Ibaraki (JP); Hideyuki Higashimura, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 14 days.

(21) Appl. No.: 13/807,226

(22) PCT Filed: Jun. 24, 2011

(86) PCT No.: PCT/JP2011/064575
§ 371 (c)(1),
(2), (4) Date: Dec. 27, 2012

(87) PCT Pub. No.: WO2012/002284
PCT Pub. Date: Jan. 5, 2012

(65) Prior Publication Data
US 2013/0099224 A1 Apr. 25, 2013

(30) Foreign Application Priority Data

Jun. 29, 2010 (JP) ................................. 2010-147687
Oct. 8, 2010 (JP) ................................. 2010-228224
Mar. 28, 2011 (JP) ................................. 2011-069375
Mar. 28, 2011 (JP) ................................. 2011-070712

(51) Int. Cl.
*H01L 29/06* (2006.01)
*H01L 51/52* (2006.01)
(Continued)

(52) U.S. Cl.
CPC ............ *H01L 51/5012* (2013.01); *C08G 61/02* (2013.01); *C08G 2261/412* (2013.01); *C07D 471/04* (2013.01); *H01L 51/0039* (2013.01);
(Continued)

(58) Field of Classification Search
USPC .............. 257/40, 59, 213, 472, 734, E21.158, 257/E33.061, E51.018; 313/504; 438/46, 438/82
See application file for complete search history.

(56) References Cited

U.S. PATENT DOCUMENTS

2005/0247938 A1* 11/2005 Okamoto et al. ................ 257/59
2009/0078946 A1* 3/2009 Jeong et al. ..................... 257/94
(Continued)

FOREIGN PATENT DOCUMENTS

JP        9-330791 A    12/1997
JP        2007-154174 A   6/2007
(Continued)

OTHER PUBLICATIONS

Wenjin Zeng, et al., "Polymer Light-Emitting Diodes with Cathodes Printed from Conducting Ag Paste", Advanced Materials, 2007, pp. 810-814, vol. 19.

*Primary Examiner* — Dao H Nguyen
(74) *Attorney, Agent, or Firm* — Sughrue Mion, PLLC

(57) ABSTRACT

Provided are a light-emitting device and a photovoltaic cell having excellent characteristics. A light-emitting device (10) includes a cathode (34), an anode (32), a light-emitting layer (50) interposed between the cathode (34) and the anode (32), and an electron injection layer (44) provided between the cathode (34) and the light-emitting layer (50) and connected to the cathode (34), in which at least one of the anode (32) and the cathode (34) contains a conductive material having an aspect ratio of 1.5 or more, and the electron injection layer (44) contains an organic compound having at least one of an ionic group and a polar group.

13 Claims, 2 Drawing Sheets

(51) Int. Cl.
*C08G 61/02* (2006.01)
*C07D 471/04* (2006.01)
*H01L 51/00* (2006.01)
*H01L 51/50* (2006.01)
*H01L 51/42* (2006.01)

(52) U.S. Cl.
CPC ......... *H01L 51/0003* (2013.01); *H01L 51/0002* (2013.01); *C08G 2261/149* (2013.01); *Y02E 10/549* (2013.01); *C08G 2261/411* (2013.01); *H01L 51/42* (2013.01); *H01L 51/5076* (2013.01); *H01L 51/0037* (2013.01); *H01L 51/4253* (2013.01); *H01L 51/424* (2013.01); *C08G 2261/1424* (2013.01); *H01L 51/5092* (2013.01); *C08G 2261/3142* (2013.01); *C08G 2261/95* (2013.01); *C08G 2261/1426* (2013.01)
USPC ............... 257/40; 257/59; 257/213; 257/472; 257/734; 257/E21.158; 257/E33.061; 257/E51.018; 313/504; 438/46; 438/82

(56) References Cited

U.S. PATENT DOCUMENTS

| | | | |
|---|---|---|---|
| 2009/0091254 A1* | 4/2009 | Jeong et al. | 313/504 |
| 2009/0233086 A1 | 9/2009 | Hirai | |
| 2010/0157202 A1 | 6/2010 | Kobayashi et al. | |
| 2012/0025185 A1* | 2/2012 | Kasamatsu | 257/40 |
| 2012/0119643 A1 | 5/2012 | Yamamoto | |
| 2013/0112951 A1* | 5/2013 | Xia et al. | 257/40 |

FOREIGN PATENT DOCUMENTS

| | | |
|---|---|---|
| JP | 2007-311358 A | 11/2007 |
| JP | 2008-140559 A | 6/2008 |
| JP | 2009-105042 A | 5/2009 |
| JP | 2009-224183 A | 10/2009 |
| JP | 2011-034711 A | 2/2011 |
| WO | 2006/128352 A1 | 12/2006 |
| WO | 2007/009331 A1 | 1/2007 |

* cited by examiner

LIGHT-EMITTING DEVICE AND PHOTOVOLTAIC CELL, AND METHOD FOR MANUFACTURING THE SAME

CROSS REFERENCE TO RELATED APPLICATIONS

This application is a National Stage of International Application No. PCT/JP2011/064575 filed Jun. 24, 2011, claiming priority based on Japanese Patent Application Nos. 2010-147687, filed Jun. 29, 2010, 2010-228224 filed Oct. 8, 2010, 2011-070712 filed Mar. 28, 2011 and 2011-069375 filed Mar. 28, 2011, the contents of all of which are incorporated herein by reference in their entirety.

TECHNICAL FIELD

The present invention relates to a light-emitting device and a photovoltaic cell, and a method for manufacturing the same.

BACKGROUND ART

For improving light emitting efficiency and photovoltaic efficiency in an electronic device such as a light-emitting device containing organic compounds as materials for a light-emitting layer and a photovoltaic cell containing organic compounds as materials for a charge separating layer, an electron injection characteristic is required to be improved in such electronic device.

To improve the electron injection characteristic, (1) a method for forming a cathode by depositing a metal layer having a small work function further on a metal layer having a large work function such as aluminum using a deposition method; (2) a method for forming a cathode by depositing an alloy layer in which the alloy is made of a metal having a large work function and a metal having a small work function using a deposition method; and (3) a method for forming an electron injection layer made of a material such as an alkali metal compound and an alkali earth metal compound stacked by a deposition method on a cathode made of a metal layer formed by a deposition method are known.

When a deposition method is used for forming a metal layer or an alloy layer, a batch process based on a vacuum system is required. As a result, problems of reduction in yield caused by losing continuity of the manufacturing process and increase in manufacturing cost arise.

To solve these problems, a light-emitting device in which an electron injection layer, a cathode, and the like are formed by a coating method that forms a coating film using a coating solution has been reported (Patent Document 1 and Non Patent Document 1).

RELATED ART DOCUMENTS

Patent Document

Patent Document 1: WO 2007/009331

Non Patent Document

Non Patent Document 1: Advanced Materials 2007, 19, 810

DISCLOSURE OF INVENTION

Problem to be Solved by the Invention

However, when higher electric conductivity of electrodes including an anode and a cathode is tried to be achieved, thicknesses of the electrodes are required to be thick. This may cause deterioration of transparency of emitting light because electrode transparency is reduced, and as a result, brightness of the light-emitting device may be deteriorated. Therefore, when the thickness of the electrode becomes thick, it is difficult to form a light-emitting device that emits light from a side of electrode having a thick thickness. In addition, when the thickness of the electrode becomes thick, manufacturing cost may become high because the amount of used materials is increased.

The present invention aims to provide a light-emitting device that has excellent electric conductivity even in the case of thin thickness of electrode, has an improved electron injection characteristic from the cathode, and further has excellent light-emitting brightness and a method for manufacturing the same that can improve productivity, and a photovoltaic cell that has excellent electric conductivity even in the case of thin thickness of the electrode, has an improved electron injection characteristic to the cathode, and further has excellent photovoltaic efficiency and a method for manufacturing the same that can improve productivity.

Means for Solving Problem

The inventors of the present invention have eagerly investigated and have accomplished the present invention. According to the present invention, following [1] to [15] are provided:

[1] A light-emitting device comprising:
a cathode, an anode, a light-emitting layer interposed between the cathode and the anode, and an electron injection layer provided between the cathode and the light-emitting layer and connected to the cathode, wherein
at least one of the cathode and the anode comprises a conductive material having an aspect ratio of 1.5 or more, and
the electron injection layer comprises an organic compound having at least one of an ionic group and a polar group.

[2] The light-emitting device according to above [1], wherein the light-emitting device further comprises a substrate, and the cathode, the electron injection layer, the light-emitting layer and the anode are stacked on the substrate in this order such that the cathode is closer to the substrate.

[3] The light-emitting device according to above [1] or [2], wherein the cathode has optical transparency.

[4] The light-emitting device according to any one of above [1] to [3], wherein the conductive material contains a material selected from the group consisting of a metal, a metal oxide, a carbon material, and combinations thereof.

[5] The light-emitting device according to any one of above [1] to [4], wherein the ionic group is at least one group selected from the group consisting of:
a group represented by formula: —SM, a group represented by formula: —C(=O)SM, a group represented by formula: —CS$_2$M, a group represented by formula: —OM, a group represented by formula: —CO$_2$M, a group represented by formula: —NM$_2$, a group represented by formula: —NRM, a group represented by formula: —PO$_3$M, a group represented by formula: —OP(=O)(OM)$_2$, a group represented by formula: —P(=O)(OM)$_2$, a group represented by formula: —C(=O)NM$_2$, a group represented by formula: —C(=O)NRM, a group represented by formula: —C(=S)NRM, a group represented by formula: —C(=S)NM$_2$, a group represented by formula:

—B(OM)₂, a group represented by formula: —BR₃M, a group represented by formula: —B(OR)₃M, a group represented by formula: —SO₂M, a group represented by formula: —SO₂M, a group represented by formula: —NRC(=O)OM, a group represented by formula: —NRC(=O)SM, a group represented by formula: —NRC(=S)OM, a group represented by formula: —NRC(=S)SM, a group represented by formula: —OC(=O)NM₂, a group represented by formula: —OC(=O)NRM, a group represented by formula: —OC(=S)NM₂, a group represented by formula: —OC(=S)NRM, a group represented by formula: —SC(=O)NM₂, a group represented by formula: —SC(=O)NRM, a group represented by formula: —SC(=S)NM₂, a group represented by formula: —SC(=S)NRM, a group represented by formula: —NRC(=O)NM₂, a group represented by formula: —NRC(=O)NRM, a group represented by formula: —NRC(=S)NM₂, a group represented by formula: —NRC(=S)NRM, a group represented by formula: —NR₃M', a group represented by formula: —PR₃M', a group represented by formula: —OR₂M', a group represented by formula: —SR₂M', a group represented by formula: —IRM', a group represented by eliminating a hydrogen atom from an aromatic ring selected from aromatic compounds represented by following formula (n-1) to formula (n-13), wherein R represents a hydrogen atom or a hydrocarbyl group optionally having a substituent, M represents a metal cation or an ammonium cation that may have a substituent, and M' represents an anion:

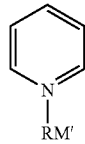
(n-1)

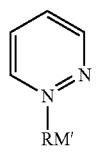
(n-2)

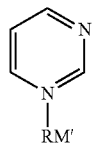
(n-3)

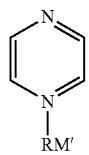
(n-4)

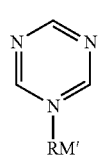
(n-5)

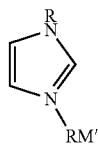
(n-6)

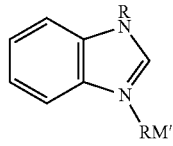
(n-7)

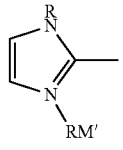
(n-8)

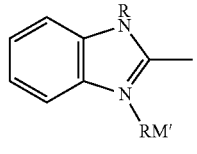
(n-9)

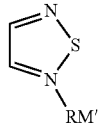
(n-10)

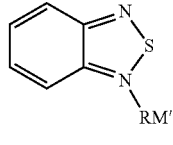
(n-11)

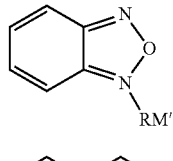
(n-12)

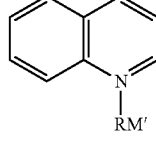
(n-13)

[6] The light-emitting device according to above [1] to [5], wherein the polar group is at least one group selected from the group consisting of a carboxy group, a sulfo group, a hydroxy group, a mercapto group, an amino group, a hydrocarbylamino group, a cyano group, a pyrrolidonyl group, a monovalent heterocyclic group and a group represented by following formula (I) to formula (IX):

$$—O—(R'O)_m—R''\qquad(I)$$

$$—R'''\!\!\!\begin{array}{c}—O\\(OR')_m\end{array}\qquad(II)$$

$$—S—(R'S)_q—R''\qquad(III)$$

—C(=O)—(R'—C(=O))$_q$—R" (IV)

—C(=S)—(R'—C(=S))$_q$—R" (V)

—N{(R')$_q$R"}$_2$ (VI)

—C(=O)O—(R'—C(=O)O)$_q$—R" (VII)

—C(=O)—O—(R'O)$_q$—R" (VIII)

—NHC(=O)—(R'NHC(=O))$_q$—R" (IX)

wherein, in formula (I) to formula (IX),
R' represents a hydrocarbylene group optionally having a substituent,
R" represents a hydrogen atom, a hydrocarbyl group optionally having a substituent, a carboxy group, a sulfo group, a hydroxy group, a mercapto group, an amino group, a group represented by formula: —NR$^c_2$, a cyano group, or a group represented by formula: —C(=O)NR$^c_2$,
R'" represents a trivalent hydrocarbon group optionally having a substituent,
m represents an integer of 1 or more,
q represents an integer of zero or more,
R$^c$ represents an alkyl group having 1 to 30 carbon atoms that may have a substituent, or an aryl group having 6 to 50 carbon atoms that may have a substituent, and
when R', R", and R'" are each plurally present, each R', R", and R'" may be the same as or different from each other.

[7] The light-emitting device according to any one of above [1] to [6], wherein the organic compound having at least one of an ionic group and a polar group is a conjugated compound.

[8] The light-emitting device according to above [7], wherein the conjugated compound has a structural unit represented by following formula (X):

wherein, in formula (X), Ar$^1$ represents an aromatic group having a valence of (n$^1$+1); R$^1$ represents a direct bond or a group having a valence of (m$^1$+1); X$^1$ represents a group having an ionic group or a polar group; m$^1$ and n$^1$ are each independently an integer of 1 or more; when R$^1$ is a direct bond, m$^1$ is 1; when R$^1$, X$^1$ and m$^1$ are each plural, each R$^1$, X$^1$, and m$^1$ may be the same as or different from each other,
or a structural unit represented by following formula (XI):

wherein, in formula (XI), Ar$^2$ represents an aromatic group having a valence of (n$^2$+2); R$^2$ represents a direct bond or a group having a valence of (m$^2$+1); X$^2$ represents a group having an ionic group or a polar group; m$^2$ and n$^2$ are each independently an integer of 1 or more; when R$^2$ is a direct bond, m$^2$ is 1; when R$^2$, X$^2$ and m$^2$ are each plural, each R$^2$, X$^2$ and m$^2$ may be the same as or different from each other,
or both of structural units represented by formula (X) and formula (XI).

[9] The light-emitting device according to above [8], wherein Ar$^1$ represents a group optionally having a substituent and represented by eliminating (n$^1$+1) hydrogen atoms from an aromatic ring of aromatic compounds represented by any one of the following formulae; and Ar$^2$ represents a group optionally having a substituent and represented by eliminating (n$^2$+2) hydrogen atoms from an aromatic ring of aromatic compounds represented by any one of the following formulae.

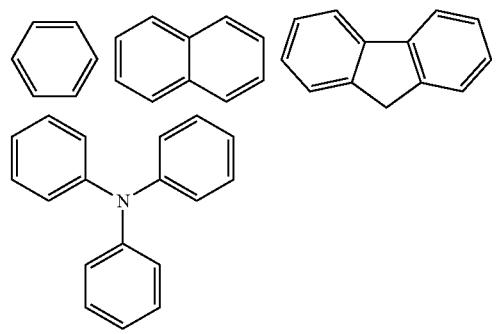

[10] The light-emitting device according to any one of above [1] to [9], wherein at least one of the cathode, the anode, and the electron injection layer contains an ionic compound.

[11] The light-emitting device according to above [10], wherein the ionic compound is a compound having a structure represented by following formula (h-1):

M$^{m+}_a$X$^{m'-}_b$ (h-1)

wherein, in formula (h-1), M$^{m+}$ represents a metal cation; represents an anion; a and b are each independently an integer of 1 or more; when M$^{m+}$ and are each plurally present, each M$^{m+}$ and may be the same as or different from each other.

[12] The light-emitting device according to above [10] or [11], wherein the electron injection layer contains the ionic compound, and the ratio of the ionic compound in the electron injection layer is 0.1 parts by weight or more and 100 parts by weight or less, with respect to 100 parts by weight of the organic compound having at least one of an ionic group and polar group.

[13] A method for manufacturing a light-emitting device according to any one of above [1] to [12] comprising a cathode, an anode, a light-emitting layer interposed between the cathode and the anode, and an electron injection layer provided between the cathode and the light-emitting layer and connected to the cathode, the method comprising the steps of:
applying a coating solution that comprises a conductive material having an aspect ratio of 1.5 or more, thereby forming at least one of the cathode and the anode, and
applying a coating solution that comprises an organic compound having at least one of an ionic group and a polar group, thereby forming the electron injection layer connected to the cathode.

[14] A photovoltaic cell comprising:
a cathode, an anode, a charge separating layer interposed between the cathode and the anode, and an electron injection layer provided between the cathode and the charge separating layer and connected to the cathode, wherein
at least one of the cathode and the anode comprises a conductive material having an aspect ratio of 1.5 or more, and the electron injection layer comprises an organic compound having at least one of an ionic group and a polar group.

[15] A method for manufacturing a photovoltaic cell comprising a cathode, an anode, a charge separating layer interposed between the cathode and the anode, and an electron injection layer provided between the cathode and the charge separating layer and connected to the cathode, the method comprising the steps of:

applying a coating solution that contains an organic compound having at least one of an ionic group and a polar group, thereby forming the electron injection layer connected to the cathode, and applying a coating solution that contains the conductive material having the aspect ratio of 1.5 or more, thereby forming at least one of the cathode and the anode.

Effect of the Invention

A light-emitting device and a photovoltaic cell of the present invention comprise electrodes made by using a material that can reduce an electrode thickness while improving electric conductivity and an electron injection layer made by using a material that has an excellent electron injection characteristic. Therefore, with the light-emitting device and the photovoltaic cell of the present invention, light transparency can be improved because of the improvement of transparency of the electrodes and further the electron injection characteristic of the electron injection layer can be improved. As a result, the light-emitting brightness of the light-emitting device and the photovoltaic efficiency of the photovoltaic cell can be improved.

With the method for manufacturing a light-emitting device and a photovoltaic cell of the present invention, the formation step of the cathode and the following formation step of a charge injection layer are performed as a convenient coating method that can be performed at normal pressure (atmospheric pressure). Therefore, the light-emitting device and the photovoltaic cell having excellent characteristics can be manufactured in convenient steps with high productivity because the formation step of the electron injection layer and the formation step of the cathode can be continuously performed at normal pressure. In addition, the manufacturing cost can be reduced because the amount of the used material can be reduced by reduction in the electrode thickness.

DESCRIPTION OF EMBODIMENTS

Figure 1:
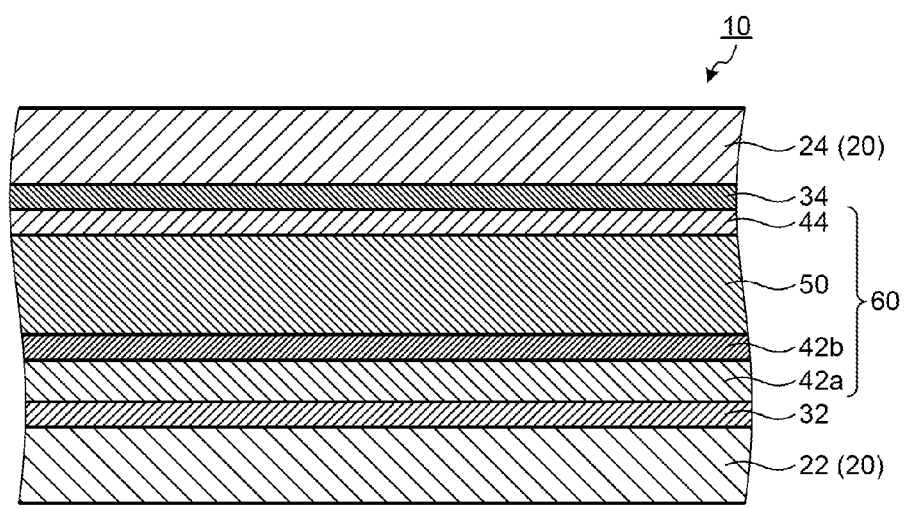
FIG. 1 is a cross-sectional view schematically illustrating an example of constitution of a light-emitting device.

Hereinafter, embodiments of the present invention will be described with reference to the drawings. Each drawing only schematically illustrates shapes, sizes, and arrangements of constituents in such a degree that the present invention can be understood. The present invention is not limited by the following description, and each constituent can be modified within a range without departing from the scope of the present invention. In each drawing used for the following description, the same reference numerals may be assigned to the same constituents and overlapped description may be omitted. Elements of the present invention are not always manufactured or used in the arrangement illustrated in the drawings. Hereinafter, one direction of the thickness direction of the substrate may be described as "upper" and the other direction of the thickness direction of the substrate may be described as "lower".

<Constitution Example of Light-Emitting Device>

With reference to FIG. 1, an example of constitution of a light-emitting device will be described.

A light-emitting device according to an embodiment of the present invention comprises: a cathode, an anode, a light-emitting layer interposed between the cathode and the anode, and an electron injection layer provided between the cathode and the light-emitting layer and connected to the cathode, in which at least one of the cathode and the anode contains a conductive material having an aspect ratio of 1.5 or more, and the electron injection layer contains an organic compound having at least one of an ionic group and a polar group.

FIG. 1 is a cross-sectional view schematically illustrating an example of constitution of a light-emitting device.

As illustrated in FIG. 1, a light-emitting device 10 comprises an anode 32 and a cathode 34 as basic constituents, and a layered structure body 60 interposed between the anode 32 and the cathode 34.

The layered structure body 60 is constituted by stacking a plurality of organic layers. At least one layer of the organic layers is a light-emitting layer 50. The layered structure body 60 also has an electron injection layer 44 as at least one organic layer of the organic layers. The electron injection layer 44 is provided between the cathode 34 and the light-emitting layer 50.

Although the layered structure body 60 can be constituted by only the organic layers, the layered structure body 60 may further comprise inorganic layers made of inorganic materials or layers made by mixing an organic material and an inorganic material.

In this embodiment, the anode 32 is provided on one of the two main surfaces facing each other in a direction of the thickness of a first substrate 22. A hole injection layer 42a is provided so as to be connected to the anode 32.

A hole transport layer 42b is provided so as to be connected to the hole injection layer 42a. The light-emitting layer 50 is provided so as to be connected to the hole transport layer 42b. The electron injection layer 44 is provided so as to be connected to the light-emitting layer 50. The cathode 34 is provided so as to be connected to the electron injection layer 44. A second substrate 24 is provided so as to be connected to the cathode 34.

The layered body 60 is stacked on the anode 32. In this constitution example, the layered structure body 60 is composed of the hole injection layer 42a, the hole transport layer 42b, the light-emitting layer 50, and the electron injection layer 44, and is composed of the organic layers that are interposed between the anode 32 and the cathode 34.

The light-emitting device 10 is characterized in that at least one of the cathode 34 and the anode 32 contains a conductive material having an aspect ratio of 1.5 or more, and the electron injection layer 44 contains an organic compound having at least one of an ionic group and a polar group.

Hereinafter, the constituents of the light-emitting device 10 will be specifically described.

—Substrate—

Each of substrates 20 constituting the light-emitting device 10 (the first substrate 22 and the second substrate 24) can be provided so as to be connected to one of the anode 32 and the cathode 34. The substrates 20 may be constituted by a material that is not chemically changed during formation of other layers such as the electron injection layer and the light-emitting layer. Examples of the material for the substrates 20 may include glasses, plastics such as polyethylene terephthalate, polyethylene, polypropylene, and polycarbonate, and silicon.

—Cathode—

In the light-emitting device 10, a material for the cathode 34 is preferably a material capable of being applied onto the substrates 20 by a coating method using a coating solution, and the material for the cathode 34 preferably contains a conductive material having an aspect ratio of 1.5 or more.

Examples of the conductive material may include a material containing one or more materials selected from the group consisting of a metal, a metal oxide, and a carbon material. Examples of the conductive materials may include a metal such as aluminum, gold, platinum, silver, and copper and an alloy thereof; a metal oxide comprising indium oxide, zinc oxide, tin oxide and mixtures thereof such as indium-tin oxide (ITO), aluminum-zinc oxide (AZO), indium-zinc oxide (IZO), tin-antimony oxide and NESA; and a carbon material such as carbon nanotube and graphite. These conductive materials can be used singly or in combination of two or more materials.

Transition metals are preferable as the metal because of their excellent stability as metals. Metals of group 11 in the periodic table are more preferable and silver is further preferable. These metals can be used singly or in combination of two or more metals.

ITO and IZO are preferable as the metal oxides.

As the carbon materials, carbon nanotube and graphite are more preferable, and carbon nanotube is further preferable.

An aspect ratio refers to a ratio of the longest diameter and the shortest diameter (longest diameter/shortest diameter) in a rod-like body, wire-like body, and the like. When an aspect ratio has a distribution, the aspect ratio refers to the average value. Here, the average value refers to an arithmetic average value. An aspect ratio of the conductive material can be determined with reference to a photograph taken by using a scanning electron microscope.

The aspect ratio is preferably 2 or more, more preferably 5 or more, further preferably 10 or more, particularly preferably 50 or more, especially preferably 100 or more, and extremely preferably 300 or more because electric conductivity of the cathode is improved.

When the aspect ratio is less than 1.5, formation of electric conduction paths may be insufficient. This may cause reduction in electric conductivity.

The upper limit of the aspect ratio is not limited. The aspect ratio is preferably $10^7$ or less, more preferably $10^6$ or less, further preferably $10^5$ or less, particularly preferably $10^4$, and especially preferably $10^3$ or less because dispersibility is improved.

The conductive material having the aspect ratio of 1.5 or more is preferably a nano-structure body.

The nano-structure body is a metal, a metal oxide, or a carbon material or a combination of two or more of these materials having nano-order diameter. The shortest diameter of the nano-structure body is usually 1 nm or more and less than 1,000 nm. The shortest diameter of the nano-structure body is preferably 800 nm or less, more preferably 600 nm or less, further preferably 300 nm or less, particularly preferably 150 nm or less, and especially preferably 100 nm or less because electric conductivity and dispersibility are improved.

The lowest limit of the shortest diameter of the nano-structure body is usually 1 nm. The shortest diameter of the nano-structure body is preferably 5 nm or more, more preferably 10 nm or more, and further preferably 30 nm or more because electric conductivity is improved.

The longest diameter of the nano-structure body is usually 1,000 nm or more, preferably 1,300 nm or more, more preferably 1,600 nm or more, further preferably 2,000 nm or more, particularly preferably 2,500 nm or more, and especially preferably 3,000 nm or more because electric conductivity is improved. The longest diameter of the nano-structure body is usually 1 cm or less, preferably 1 mm or less, more preferably 0.5 mm or less, further preferably 0.3 mm or less, and especially preferably 0.1 mm or less.

From the characteristics of shapes, example of the nano-structure body may include an anisotropic nano-particle, a nano-wire, a nano-tube, a nano-rod, and a nano-sheet.

The nano-rod, the nano-tube, and the nano-wire are preferable as the nano-structure body because these nano-structure bodies are easy to be synthesized and can secure a sufficient aspect ratio. An aspect ratio of the nano-rod is preferably 1.5 to 20 and more preferably 5 to 15. An aspect ratio of the nano-wire is preferably 20 to $10^5$ and more preferably 100 to $10^4$.

From the characteristics of shapes, examples of silver as the conductive material of the cathode may include anisotropic silver nano-particle, a silver nano-wire, a silver nano-tube, a silver nano-rod, and a silver nano-sheet. The silver nano-rod, the silver nano-tube, and the silver nano-wire are preferable because these silver nano-structure bodies are easy to be synthesized and can secure a sufficient aspect ratio.

The conductive material according to the present invention having an aspect ratio of 1.5 or more is commercially available or can be manufactured by using conventionally known methods. A liquid phase method, a gas phase method, or the like can be used as the method for manufacturing the conductive material having an aspect ratio of 1.5 or more. The conductive material having an aspect ratio of 1.5 or more manufactured by any methods may be used.

A method for manufacturing a gold nano-structure is disclosed in JP 2006-233252 A as a method for manufacturing nano-structure bodies. A method for manufacturing a silver nano-structure is disclosed in Xia, Y. et al., Chem. Mater. (2002), 14, 4736-4745; and Xia, Y. et al., Nano Letters (2003) 3, 955-960; and Xia, Y. et al., J. Mater. Chem. (2008) 18, 437-441. A method for manufacturing a copper nano-structure is disclosed in JP 2002-266007 A. A method for manufacturing a cobalt nano-structure is disclosed in JP 2004-149871 A.

At the time of formation of the cathode by a coating method, a spin coating method, a casting method, a microgravure coating method, a gravure coating method, a bar coating method, a roll coating method, a wire-bar coating method, a dip coating method, a spray coating method, a screen printing method, a flexographic printing method, an offset printing method, an ink-jet printing method, a capillary coating method, and a nozzle coating method can be employed to form a film, when the film made of a coating solution containing a conductive material having an aspect ratio of 1.5 or more is formed by coating.

A solvent used for the coating solution is preferably a solvent that can dissolve the material of the cathode or a solvent that can homogeneously disperse the material of the cathode. Examples of the solvent may include chlorinated hydrocarbon solvents such as chloroform, methylene chloride, 1,2-dichloroethane, 1,1,2-trichloroethane, chlorobenzene, and o-dichlorobenzene; ether solvents such as tetrahydrofuran and dioxane; aromatic hydrocarbon solvents such as toluene and xylene; aliphatic hydrocarbon solvents such as cyclohexane, methylcyclohexane, pentane, hexane, heptane, octane, nonane, and decane; ketone solvents such as acetone, methyl ethyl ketone, and cyclohexanone; ester solvents such as ethyl acetate, butyl acetate, and ethyl cellosolve acetate; polyvalent alcohols and derivatives thereof such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; alcohol solvents such as methanol, ethanol, propanol, isopropyl alcohol, and cyclohexanol; sulfoxide solvents such as dimethylsulfoxide; and amide solvents such as N-methyl-2-pyrrolidone and N,N-dimethylformamide. These solvents can be used singly or in combination of two or more solvents.

The cathode has a single layer structure made of only one layer or a stacked structure made of two or more or layers. When the cathode has a stacked structure made of two or more layers, the cathode is formed by, for example, sequentially stacking two or more layers using a coating method or stacking two or more layers that is individually formed by a casting method and the like by a lamination method.

The cathode 34 optionally contains an ionic compound other than the conductive material having an aspect ratio of 1.5 or more.

Here, the ionic compound contains a cation and an anion. The ionic compound optionally contains hydrated water and/or a neutral ligand. The neutral ligand is a nonionic compound having a lone pair that can form a coordinate bond. When the neutral ligand is bonded to the ionic compound, the neutral ligand does not cause change in an oxidation number of the ionic compound. Example of the compound that can be the neutral ligand may include pyridine, 2,2'-bipyridyl, phenanthroline, terpyridine, triphenylphosphine, carbon monoxide, and crown ethers.

Examples of the cation may include a metal cation, an organic cation, and an ammonium cation. The metal cation is preferable as the cation because the metal cation has excellent stability.

Examples of the metal cation may include an alkali metal cation, an alkaline earth metal cation, a typical metal cation and a transition metal cation. The alkali metal cation and the alkaline earth metal cation are preferable as the metal cation.

Examples of the alkali metal cation may include $Li^+$, $Na^+$, $K^+$, $Rb^+$, $Cs^+$, and $Fr^+$. $Li^+$, $Na^+$, $K^+$, $Rb^+$ and $Cs^+$ are preferable as the alkali metal cation, and $Cs^+$ is further preferable.

Examples of the alkaline earth metal cation may include $Mg^{2+}$, $Ca^{2+}$, $Sr^{2+}$, and $Ba^{2+}$.

Examples of the typical metal cation may include $Zn^{2+}$, $Cd^{2+}$, $Hg^+$, $Hg^{2+}$, $Al^{3+}$, $Ga^{3+}$, $In^{3+}$, $Ge^{4+}$, $Sn^{2+}$, $Sn^{4+}$, $Pb^{2+}$, $Pb^{4+}$, $Bi^{3+}$, $Tl^+$, and $Tl^{3+}$.

Examples of the transition metal cation may include $Sc^{3+}$, $Ti^{4+}$, $V^{3+}$, $V^{5+}$, $Cr^{2+}$, $Cr^{3+}$, $Mn^{2+}$, $Mn^{3+}$, $Fe^{2+}$, $Fe^{3+}$, $Co^{2+}$, $Co^{3+}$, $Ni^{2+}$, $Ni^{3+}$, $Cu^+$, $Cu^{2+}$, $Y^{3+}$, $Zr^{4+}$, $Nb^{3+}$, $Nb^{5+}$, $Mo^{4+}$, $Mo^{6+}$, $Ru^{4+}$, $Rh^{3+}$, $Pd^+$, $Pd^{2+}$, $Ag^+$, $Sb^{3+}$, $La^{3+}$, $Ce^{3+}$, $Ce^{4+}$, $Eu^{3+}$, $Hf^{4+}$, $Ta^{5+}$, $W^{6+}$, $Re^{6+}$, $Os^{2+}$, $Os^{4+}$, $Ir^{4+}$, $Pt^{2+}$, and $Pt^{4+}$.

Examples of the organic cation may include onium cations having an aromatic ring containing a nitrogen atom such as imidazolium cation and pyridinium cation; an ammonium cation; and a phosphonium cation.

Examples of the anion may include $F^-$, $Cl^-$, $Br^-$, $I^-$, $OH^-$, $CN^-$, $NO_3^-$, $NO_2^-$, $ClO^-$, $ClO_2^-$, $ClO_3^-$, $ClO_4^-$, $CrO_4^{2-}$, $HSO_4^-$, $SCN^-$, $BF_4^-$, $PF_6^-$, an anion represented by the formula: $R^3O^-$, an anion represented by the formula: $R^4COO^-$, an anion represented by the formula: $R^5SO_3^-$, an anion represented by the formula: $R^6OCO_2^-$, an anion represented by the formula: $R^7SO_2^-$, an anion represented by the formula: $R^8S^-$, an anion represented by the formula: $B(R^9)_4^-$, $CO_3^{2-}$, $S^{2-}$, $S_2^{2-}$, $SO_4^{2-}$, $S_2O_3^{2-}$, $PO_4^{3-}$ and $O^{2-}$. As the anion, $F^-$, $Cl^-$, $Br^-$, $I^-$, $OH^-$, $NO_3^-$, $BF_4^-$, $PF_6^-$, the anion represented by the formula: $R^3O^-$, the anion represented by the formula: $R^4COO^-$, the anion represented by the formula: $R^5SO_3^-$, the anion represented by the formula: $R^6CO_3^-$, the anion represented by the formula: $R^7SO_2^-$, $CO_3^{2-}$, $SO_4^{2-}$, and $PO_4^{3-}$ are preferable; $F^-$, $Cl^-$, $Br^-$, $OH^-$, $NO_3^-$, $BF_4^-$, $PF_6^-$, the anion represented by the formula: $R^3O^-$, the anion represented by the formula: $R^4COO^-$, the anion represented by the formula: $R^5SO_3^-$, $CO_3^{2-}$, and $SO_4^{2-}$ are more preferable; $F^-$, $Cl^-$, $Br^-$, $I^-$, $OH^-$, $NO_3^-$, $BF_4^-$, $PF_6^-$, the anion represented by the formula: $R^4COO^-$, the anion represented by the formula: $R^5SO_3^-$, $CO_3^{2-}$, and $SO_4^{2-}$ are further preferable; and $F^-$, $OH^-$, $NO_3^-$, the anion represented by the formula: $R^4COO^-$, and $CO_3^{2-}$ are particularly preferable.

In the formulae described above, $R^3$, $R^4$, $R^5$, $R^6$, $R^7$, $R^8$, and $R^9$ are each independently a hydrocarbyl group optionally having a substituent.

Example of the hydrocarbyl group optionally having a substituent and are represented by $R^3$, $R^4$, $R^5$, $R^6$, $R^7$, $R^8$, and $R^9$ may include alkyl groups having 1 to 50 carbon atoms such as a methyl group, an ethyl group, a propyl group, an isopropyl group, a butyl group, an isobutyl group, a sec-butyl group, a tert-butyl group, a pentyl group, a hexyl group, a nonyl group, a dodecyl group, a pentadecyl group, an octadecyl group, and a docosyl group; cyclic saturated hydrocarbyl groups having 3 to 50 carbon atoms such as a cyclopropyl group, a cyclobutyl group, cyclopentyl group, a cyclohexyl group, a cyclononyl group, a cyclododecyl group, a norbornyl group, and an adamantyl group; alkenyl groups having 2 to 50 carbon atoms such as an ethenyl group, a propenyl group, a 3-butenyl group, a 2-butenyl group, a 2-pentenyl group, a 2-hexenyl group, a 2-nonenyl group, and a 2-dodecenyl group; aryl groups having 6 to 50 carbon atoms such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-tert-butylphenyl group, a 4-hexylphenyl group, a 4-cyclohexylphenyl group, a 4-adamantylphenyl group, and 4-phenylphenyl group; and arylalkyl groups having 7 to 50 carbon atoms such as a phenylmethyl group, a 1-phenyleneethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group, and a 6-phenyl-1-hexyl group. As the hydrocarbyl group optionally having a substituent, alkyl groups having 1 to 50 carbon atoms and aryl groups having 6 to 50 carbon atoms are preferable; alkyl groups having 1 to 12 carbon atoms and aryl groups having 6 to 18 carbon atoms are more preferable; and alkyl groups having 1 to 6 carbon atoms and aryl groups having 6 to 12 carbon atoms are further preferable. Examples of the substituent that the hydrocarbyl group may have may include an alkoxy group, an aryloxy group, an amino group, an substituted amino group, a silyl group, a substituted silyl group, a halogen atom, an imine residual group, an amido group, an acid imido group, a monovalent heterocyclic group, a mercapto group, a hydroxy group, a carboxy group, a cyano group, and a nitro group. As the substituent that the hydrocarbyl group may have, the amino group, the monovalent heterocyclic group, the mercapto group, the hydroxy group, and the carboxy group are preferable, and the amino group, a pyridyl group, the mercapto group, the hydroxy group, and the carboxy group are more preferable. When the hydrocarbyl group has a plurality of substituents, the substituents may be the same as or different from each other.

The alkoxy group being a substituent that the hydrocarbyl group may have may be a straight chain, a branched chain, or cyclic. The number of carbon atoms in the alkoxy group is usually 1 to 20, and preferably 1 to 10. Examples of the alkoxy group that the hydrocarbyl group may have may include a methoxy group, an ethoxy group, a propyloxy group, an isopropyloxy group, a butoxy group, an isobutoxy group, a sec-butoxy group, a tert-butoxy group, a pentyloxy group, a hexyloxy group, a cyclohexyloxy group, a heptyloxy group, an octyloxy group, a nonyloxy group, a decyloxy group, and a lauryloxy group. Hydrogen atoms in the alkoxy group that the hydrocarbyl group may have are optionally substituted by fluorine atoms. Examples of the alkoxy group substituted by fluorine atoms may include a trifluoromethoxy group, a pentafluoroethoxy group, a perfluorobutoxy group, a perfluorohexyloxy group, a perfluorooctyloxy group, a methoxymethyloxy group, and a 2-methoxyethyloxy group.

The number of carbon atoms in the aryloxy group being a substituent that the hydrocarbyl group may have is usually 6 to 60, and preferably 6 to 48. Examples of the aryloxy group that the hydrocarbyl group may have may include a phenoxy group, a $C_1$-$C_{12}$ alkoxyphenoxy group (here, C represents a carbon atom. The subscript number represents the number of carbon atoms. The description "$C_1$-$C_{12}$" represents that the number of carbon atoms is 1 to 12. The same will apply hereinafter), a $C_1$-$C_{12}$ alkylphenoxy group, a 1-naphthyloxy group, a 2-naphthyloxy group, and a pentafluorophenyloxy group.

Examples of the $C_1$-$C_{12}$ alkoxyphenoxy group may include a methoxyphenoxy group, an ethoxyphenoxy group, a propyloxyphenoxy group, an isopropyloxyphenoxy group, a butoxyphenoxy group, an isobutoxyphenoxy group, a sec-butoxyphenoxy group, a tert-butoxyphenoxy group, a pentyloxyphenoxy group, a hexyloxyphenoxy group, a cyclohexyloxyphenoxy group, a heptyloxyphenoxy group, an octyloxyphenoxy group, a 2-ethylhexyloxyphenoxy group, a nonyloxyphenoxy group, a decyloxyphenoxy group, a 3,7-dimethyloctyloxyphenoxy group, and a lauryloxyphenoxy group.

Examples of the $C_1$-$C_{12}$ alkylphenoxy group may include a methylphenoxy group, an ethylphenoxy group, a dimethylphenoxy group, a propylphenoxy group, 1,3,5-trimethylphenoxy group, a methylethylphenoxy group, an isopropylphenoxy group, a butylphenoxy group, an isobutylphenoxy group, a sec-butylphenoxy group, a tert-butylphenoxy group, a pentylphenoxy group, an isoamylphenoxy group, a hexylphenoxy group, a heptylphenoxy group, an octylphenoxy group, a nonylphenoxy group, a decylphenoxy group, and a dodecylphenoxy group.

Examples of the substituted amino group being a substituent that the hydrocarbyl group may have may include an amino group in which one or more hydrogen atoms in the amino group are substituted by one or more groups selected from the group consisting of an alkyl group, an aryl group, an arylalkyl group, and a monovalent heterocyclic group. The number of carbon atoms in the substituted amino group is usually 1 to 60, and preferably 2 to 48. Examples of the substituted amino group that the hydrocarbyl group may have may include a methylamino group, a dimethylamino group, an ethylamino group, a diethylamino group, a propylamino group, a dipropylamino group, an isopropylamino group, a diisopropylamino group, a butylamino group, an isobutylamino group, a sec-butylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a $C_1$-$C_{12}$ alkoxyphenylamino group, a di($C_1$-$C_{12}$ alkoxyphenyl)amino group, a di($C_1$-$C_{12}$ alkylphenyl)amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl-$C_1$-$C_{12}$ alkylamino group, a $C_1$-$C_{12}$ alkoxyphenyl-$C_1$-$C_{12}$ alkylamino group, a $C_1$-$C_{12}$ alkylphenyl-$C_1$-$C_{12}$ alkylamino group, a di($C_1$-$C_{12}$ alkoxyphenyl-$C_1$-$C_{12}$ alkyl)amino group, a di($C_1$-$C_{12}$ alkylphenyl-$C_1$-$C_{12}$ alkyl)amino group, a 1-naphthyl-$C_1$-$C_{12}$ alkylamino group, and a 2-naphthyl-$C_1$-$C_{12}$ alkylamino group.

Examples of the substituted silyl group being a substituent that the hydrocarbyl group may have may include a silyl group in which one or more hydrogen atoms in the silyl group are substituted by one or more groups selected from the group consisting of an alkyl group, an aryl group, an arylalkyl group, and a monovalent heterocyclic group. The number of carbon atoms in the substituted silyl group is usually 1 to 60, and preferably 2 to 48.

Examples of the halogen atom being a substituent that the hydrocarbyl group may have may include a fluorine atom, a chlorine atom, a bromine atom, and an iodine atom.

The imine residual group being a substituent that the hydrocarbyl group may have refers to a residual group in which, from an imine compound having a structure represented by the formula: H—N=C< or the formula: —N=CH—, one hydrogen atom is eliminated from this structure. Examples of the imine compound may include aldimine, ketimine, and a compound that is made by substituting a hydrogen atom bonded to a nitrogen atom in aldimine with an alkyl group, an aryl group, an arylalkyl group, an arylalkenyl group, and an arylalkynyl group. The number of carbon atoms in the imine residual group is usually 2 to 20, and preferably 2 to 18. Examples of the imine residual group that the hydrocarbyl group may have may include a group represented by the general formula: —CR$^\beta$=N—R$^\gamma$ or the general formula: —N=C(R$^\gamma$)$_2$. In the general formula, R$^\beta$ represents a hydrogen atom, an alkyl group, an aryl group, an arylalkyl group, an arylalkenyl group, and an arylalkynyl group, and R$^\gamma$s independently represent an alkyl group, an aryl group, an arylalkyl group, an arylalkenyl group, and an arylalkynyl group when two R$^\gamma$s exist. When two R$^\gamma$s exist, however, the two R$^\gamma$s may be bonded to each other to integrally form a ring as a divalent group, for example, an alkylene group having 2 to 18 carbon atoms such as an ethylene group, a trimethylene group, a tetramethylene group, pentamethylene group, and hexamethylene group. The following groups are included as the imine residual group that the hydrocarbyl group may have.

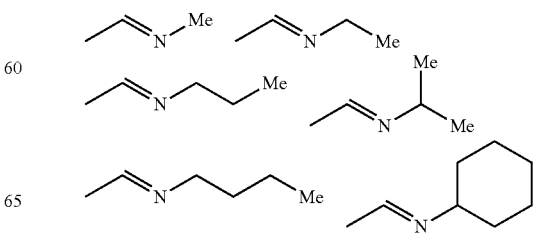

-continued

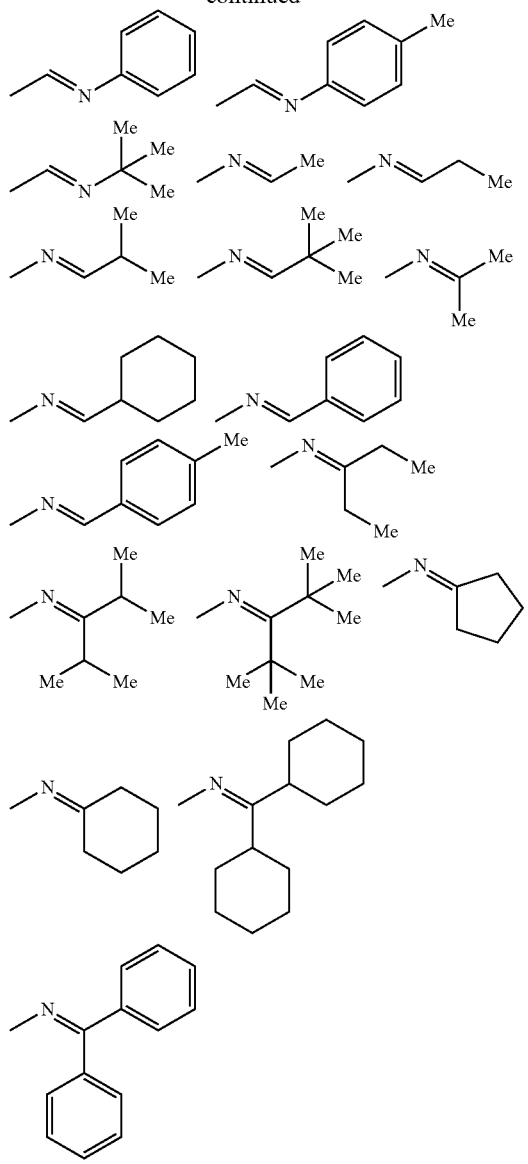
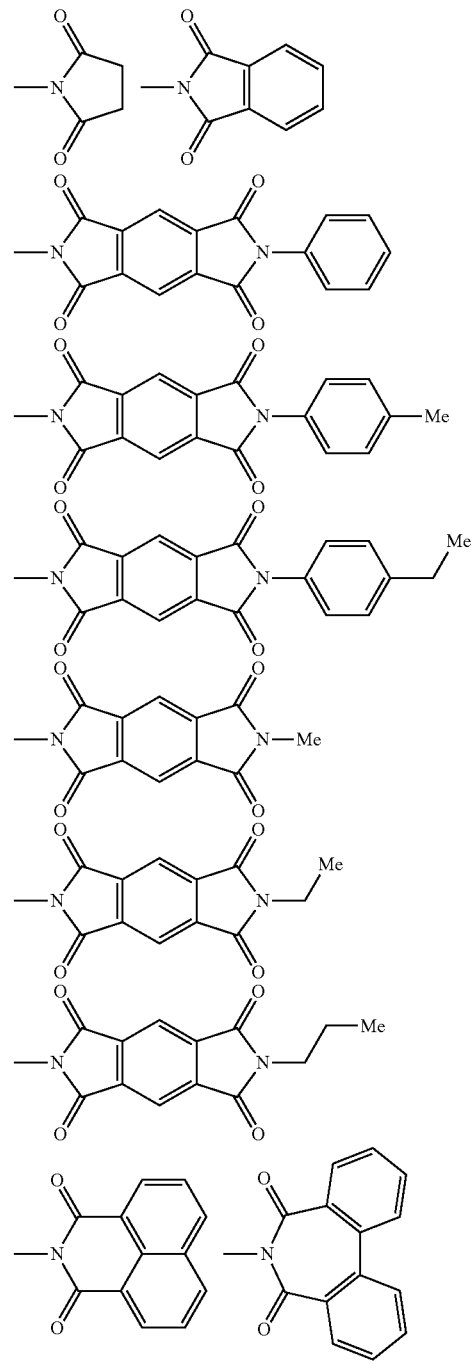

In these formulae, Me represents a methyl group, and the same will apply hereinafter.

The number of carbon atoms in the amido group being a substituent that the hydrocarbyl group may have is usually 1 to 20, and preferably 2 to 18. Examples of the amido group that the hydrocarbyl group may have may include a formamido group, an acetamido group, a propionamido group, a butyramido group, a benzamido group, a trifluoroacetamido group, a pentafluorobenzamido group, a diformamido group, a diacetamido group, a dipropionamido group, a dibutyramido group, a dibenzamido group, a ditrifluoroacetamido group, and a dipentafluorobenzamido group.

The acid imido group being a substituent that the hydrocarbyl group may have is a residual group obtained by eliminating a hydrogen atom bonded to a nitrogen atom of an acid imide from the acid imide. The number of carbon atoms in the acid imido group is usually 4 to 20, and preferably 4 to 18. The following groups are included as examples of the acid imido group.

The monovalent heterocyclic group being a substituent that the hydrocarbyl group may have is a residual atom group in which one hydrogen atom is eliminated from the heterocyclic compound optionally having a substituent. Examples of the hetero ring of the heterocyclic compound may include monocyclic heterocycles such as a pyridine ring, a 1,2-diazine ring, a 1,3-diazine ring, a 1,4-diazine ring, a 1,3,5-triazine ring, a furan ring, a pyrrole ring, a thiophene ring, a pyrazole ring, an imidazole ring, an oxazole ring, a thiazole ring, an oxadiazole ring, a thiadiazole ring, an azadiazole ring; a fused multicyclic hetero ring in which two or more rings selected from monocyclic aromatic rings are fused; and a crosslinkage-containing multicyclic aromatic ring having a structure in which two hetero rings, or one hetero ring and one aromatic ring are crosslinked through a divalent group such as a methylene group, an ethylene group and a carbonyl group. As the hetero rings, the pyridine ring, the 1,2-diazine ring, the 1,3-diazine ring, the 1,4-diazine ring, and the 1,3,5-triazine ring are preferable, and the pyridine ring and the 1,3,5-triazine ring are more preferable.

The ionic compound preferably has a structure represented by the following formula (h-1).

$$M^{m'+}{}_a X^{m'-}{}_b \qquad \text{(h-1)}$$

In formula (h-1), $M^{m'+}$ represents a metal cation. $X^{m'-}$ represents an anion. a and b are each independently an integer of 1 or more. When $M^{m'+}$ and $X^{m'-}$ are each plurally present, each $M^{m'+}$ and $X^{m'-}$ may be the same as or different from each other.

The ionic compound represented by formula (h-1) optionally contains hydrated water and/or a neutral ligand that is described above.

In formula (h-1), preferable a and b are each independently an integer of 1 to 3, and more preferably 1 or 2. Here, a and b are a combination having no charge disproportionation as a whole of the ionic compound represented by formula (h-1).

In formula (h-1), m' represents an integer of 1 or more. Definition, specific examples, and preferable examples of the metal cation represented by $M^{m'+}$ are as described above.

In formula (h-1), n' represents an integer of 1 or more. Definition, specific examples, and preferable examples of the anion represented by $X^{m'-}$ are as described above.

When the ionic compound contains the hydrated water, the ionic compound preferably has a structure represented by the following formula (h-2).

$$M^{m'+}{}_a X^{m'-}{}_b \cdot n''(H_2O) \qquad \text{(h-2)}$$

In formula (h-2), n" represents an integer of 1 or more. Definition, specific examples, and preferable examples of $M^{m'+}$, $X^{m'-}$, a and b are as described above.

Examples of the ionic compound may include lithium fluoride, sodium fluoride, potassium fluoride, cesium fluoride, calcium fluoride, gallium fluoride, lithium hydroxide, sodium hydroxide, potassium hydroxide, cesium hydroxide, calcium hydroxide, lithium hydrogen carbonate, potassium hydrogen carbonate, cesium hydrogen carbonate, barium hydrogen carbonate, lithium carbonate, sodium carbonate, potassium carbonate, cesium carbonate, barium carbonate, magnesium carbonate, calcium carbonate, copper carbonate, iron carbonate, silver carbonate, ammonium carbonate, lithium acetate, sodium acetate, potassium acetate, cesium acetate, barium acetate, magnesium acetate, calcium acetate, silver acetate, copper acetate, ammonium acetate, lithium sulfate, sodium sulfate, potassium sulfate, cesium sulfate, calcium sulfate, magnesium sulfate, aluminum sulfate, zinc sulfate, ammonium sulfate, silver sulfate, copper sulfate, iron sulfate, lead sulfate, potassium sulfite, sodium thiosulfate, lithium nitrate, potassium nitrate, sodium nitrate, cesium nitrate, calcium nitrate, ammonium nitrate, silver nitrate, iron nitrate, copper nitrate, cobalt nitrate, lead nitrate, potassium nitrite, lithium phosphate, tripotassium phosphate, trisodium phosphate, aluminum phosphate, sodium hydrogenphosphate, sodium dihydrogenphosphate, potassium perchlorate, potassium permanganate, potassium chromate, potassium cyanate, potassium thiocyanate, sodium tetrafluoroborate, sodium hexafluorophosphate, ammonium hexafluorophosphate, lithium stearate, sodium stearate, cesium stearate, calcium stearate, sodium myristate, zinc myristate, disodium glutarate, sodium 6-aminohexanoate, sodium thiomalate, sodium 4-aminocyclohexanoate, sodium linoleate, sodium glutamate, lithium benzoate, sodium benzoate, cesium benzoate, sodium terephthalate, 1-butyl-3-methylimidazolium chloride, 1-butylpyridinium hexafluorophosphate, tetrabutylammonium chloride, trimethylbutylammonium chloride, 1-hexyl-1-methylpyrrolidinium chloride, and trihexyl(tetradecyl)phosphonium hexafluorophosphate. Lithium fluoride, sodium fluoride, potassium fluoride, cesium fluoride, calcium fluoride, gallium fluoride, lithium hydroxide, sodium hydroxide, potassium hydroxide, cesium hydroxide, lithium benzoate, sodium benzoate, cesium benzoate, sodium terephthalate, 1-butyl-3-methylimidazolium chloride, 1-butylpyridinium hexafluorophosphate, tetrabutylammonium chloride, trimethylbutylammonium chloride, 1-hexyl-1-methylpyrrolidinium chloride, and trihexyl(tetradecyl)phosphonium hexafluorophosphate are preferable; lithium fluoride, sodium fluoride, potassium fluoride, cesium fluoride, calcium fluoride, gallium fluoride, lithium hydroxide, sodium hydroxide, potassium hydroxide, cesium hydroxide, lithium benzoate, sodium benzoate, cesium benzoate, and sodium terephthalate are more preferable; cesium fluoride, cesium hydroxide, and cesium benzoate are further preferable; and cesium hydroxide is particularly preferable. These ionic compounds optionally contain the hydrated water and the neutral ligand.

Examples of the compound represented by formula (h-2) may include cesium hydroxide monohydrate, cobalt chloride hexahydrate, copper sulfate monohydrate, copper sulfate trihydrate, copper sulfate pentahydrate, sodium sulfate decahydrate, sodium carbonate decahydrate, sodium carbonate monohydrate, aluminum sulfate hexadecahydrate, nickel chloride hexahydrate, tin chloride dihydrate, cobalt iodide hexahydrate, and rhodium chloride trihydrate. Cesium hydroxide monohydrate is preferable.

The ionic compound may be used singly or in combination of two or more compounds. A molecular weight of the ionic compound is preferably less than 1,000, more preferably less than 800, further preferably less than 500, and particular preferably less than 300.

The amount of added ionic compound in the cathode 34 of the light-emitting device of the present invention is usually 0.01 parts by weight or more and 1,000 parts by weight or less, preferably 0.1 parts by weight or more and 100 parts by weight or less, and more preferably 1 part by weight or more and 50 parts by weight or less, with respect to 100 parts by weight of the material of the cathode.

Any other materials can be mixed with the material for the cathode with the proviso that conductivity of the cathode 34 is not seriously impaired. When the material for the cathode is used by mixing with other materials, these materials may be mixed before the cathode 34 is formed, or may be mixed after the cathode 34 is formed.

The cathode 34 of the light-emitting device is preferably has optical transparency. The light-emitting device can emit light from a side closer to the cathode by using the cathode having the optical transparency. The aspect ratio of the conductive material is preferably 10 or more, more preferably 50 or more, further preferably 100 or more, and particularly preferably 300 or more because the optical transparency of the cathode is improved. When the aspect ratio is less than 1.5, the optical transparency may be deteriorated.

The optical transparency can be measured by using total light transmittance. In the present invention, "a cathode has optical transparency" means that a total light transmittance of the cathode is 40% or more. The total light transmittance is preferably 60% or more, further preferably 70% or more, and particularly preferably 80% or more because the characteristics of the light-emitting device are improved.

A thickness of the cathode 34 can be adjusted in consideration of electric conductivity and, in particular, light transparency when the cathode has optical transparency. The thickness of the cathode 34 is preferably 10 nm or more, more preferably 20 nm or more, further preferably 50 nm or more, and particularly preferably 100 nm or more. In addition, the thickness of the cathode 34 is preferably 30 µm or less, more preferably 10 µm or less, further preferably 5 µm or less, particularly preferably 1 µm or less, and especially preferably 500 nm or less.

Preferably, the surface of the cathode formed by the coating method is smooth and has less concavity and convexity. A height difference between a higher part (a convex part) and a lower part (a concave part) in the concavity and convexity of the surface of the cathode is preferably 1 µm or less, more preferably 100 nm or less, particularly preferably 50 nm or less, especially preferably 20 nm or less, and extremely preferably 10 nm or less.

Examples of methods reducing the concavity and convexity of the surface of the cathode may include a method in which a film formed by coating is heated at a temperature of the melting point of the conductive material or higher; a method in which pressure is applied to the surface of a film formed by coating; a method in which a film once formed by applying a coating solution on a provisional substrate is transferred onto a given substrate; and a method in which other material is filled in the concave portion of a film formed by coating.

—Anode—

In the light-emitting device 10, the anode 32 can be formed on the substrate using a material for the anode. The anode can be formed by preparing a substrate in which a conductive thin film formed by using a conductive material such as ITO is previously provided, and patterning the conductive thin film with a prescribed pattern.

A material constituting the anode 32 is preferably contains a conductive material having an aspect ratio of 1.5 or more. Definition, specific examples, and preferable examples of the conductive material having an aspect ratio of 1.5 or more that can be used as a material for the anode are the same as the definition, the specific examples, and the preferable examples of the conductive material having an aspect ratio of 1.5 or more used in the cathode as described above.

Examples of the material constituting the anode 32 may include a conductive metal oxide, a metal, a carbon material, and a conductive polymeric material. Examples of the material for the anode may include the metal oxides such as indium oxide, zinc oxide, tin oxide and mixtures thereof such as ITO, AZO, IZO, and NESA; the metals such as gold, platinum, silver, and copper; the carbon materials such as carbon nanotube and graphite; and the conductive polymeric materials such as conductive polymers including polyaniline, polythiophene (for example, poly(3,4-ethylenedioxythiophen)/polystyrene sulfonic acid), and polypyrrole, and polymers including these conductive polymers. The anode is a single layer structure made of only one layer or a stacked structure made of two or more layers.

A thickness of the anode 32 can be adjusted in consideration of electric conductivity and durability. The thickness of the anode is usually 10 nm or more, preferably 20 nm or more, more preferably 50 nm or more, and further preferably 100 nm or more. In addition, the thickness of the anode 32 is usually 10 µm or less, preferably 1 µm or less, and more preferably 500 nm or less.

Examples of methods for forming the anode 32 may include a vacuum evaporation method, a sputtering method, a lamination method in which a thin metal film is laminated by thermocompression, or a coating method. The coating method is preferable as the method for forming the anode 32. A layer made of a conductive polymeric material, or layer made of a metal oxide, a metal fluoride, or an organic insulation material may be provided between the anode 32 and the electron injection layer 44.

When a coating method in which a coating solution is applied is used as the method for forming the anode 32, examples of the solvent used for the coating solution are the same as the solvent used for the coating solution when the cathode is formed by the coating method as described above.

The anode 32 may contain an ionic compound other than the material for the anode. Definition, specific examples, and preferable examples of the ionic compound used with the material for the anode are the same as the definition, the specific examples, and the preferable examples of the ionic compound in the material used in the cathode as described above.

The ionic compound may be used singly or in combination of two or more compounds. A molecular weight of the ionic compound is preferably less than 1,000, more preferably less than 800, further preferably less than 500, and particularly preferably less than 300.

The amount of added ionic compound in the anode 32 of the light-emitting device of the present invention is usually 0.01 parts by weight or more and 1,000 parts by weight or less, preferably 0.1 parts by weight or more and 100 parts by weight or less, and more preferably 1 part by weight or more and 50 parts by weight or less, with respect to 100 parts by weight of the material of the anode.

Any other materials can be mixed with the material for the anode with proviso that conductivity of the anode 32 is not seriously impaired. Other materials may be mixed before the anode 32 is formed, or may be mixed after the anode 32 is formed.

In the present invention, a layer having a function as an anode even when the layer is formed by a composition that is made by mixing a material for the anode and the other materials is the anode.

The conductive polymeric material is preferable as a material that may be mixed with the material for the anode. Examples of the conductive polymeric material may include polyfluorene and a derivative thereof, polythiophene and a derivative thereof, polyaniline and a derivative thereof, polypyrrole and a derivative thereof, and polyphenylamine and a derivative thereof.

A hole injection material is preferable as the other material that may be mixed with the material for the anode. A layer formed by a composition made by mixing the material for the anode and the hole injection material is a layer having both functions of the hole injection layer and the anode. The layer formed by the composition made by mixing the material for the anode and the hole injection material may be referred to as an anode containing the hole injection material.

Preferably, the surface of the anode 32 formed by the coating method is smooth and has less concavity and convexity. A height difference between a convex portion and a concave portion in the concavity and convexity of the surface of the anode is preferably 1 µm or less, more preferably 100 nm or less, particularly preferably 50 nm or less, especially preferably 20 nm or less, and extremely preferably 10 nm or less.

Examples of methods reducing the concavity and convexity of the surface of the anode 32 may include a method in which a film formed by coating is heated at a temperature of the melting point of the conductive material or higher; a method in which pressure is applied to the surface of a film formed by coating; a method in which a film once formed by applying a coating solution on a provisional substrate is transferred onto a given substrate; and a method in which other material is filled in the concave portion of a film formed by coating.

At least one of the cathode 34 and the anode 32 preferably contains the conductive material having an aspect ratio of 1.5 or more. Both of the cathode 34 and the anode 32 can contain the conductive material having an aspect ratio of 1.5 or more. Preferably, the cathode 34 contains the conductive material having an aspect ratio of 1.5 or more.

—Electron Injection Layer—

The electron injection layer 44 includes an organic compound containing at least one of an ionic group and a polar group. More preferably, the electron injection layer 44 contains an organic compound having both the ionic group and the polar group. The organic compound is preferably a conjugated compound, and more preferably an aromatic compound. The electron injection layer 44 is a single layer structure made of only one layer or a stacked structure made of two or more layers.

In this specification, the conjugated compound refers to a compound having a conjugated system. As the conjugated compound, a compound including a system in which a single bond is continuously connected to a multiple bond (a double bond and a triple bond); unshared electron pairs of a nitrogen atom, an oxygen atom, a sulfur atom, or a phosphorus atom; a vacant p orbital that a boron atom has; or a d orbital for a sigma bonding that a silicon atom has, so that the single bond is interposed by them. An electron transport characteristic is improved in these conjugated compounds. Therefore, a value (%) calculated by the following formula is preferably 50% or more, more preferably 60% or more, more preferably 70% or more, further preferably 80% or more, and particularly preferably 90% or more. Aromatic compounds are especially preferably as the conjugated compound.

Formula: {(The number of atoms in a mother skeleton or a main chain contained in a region where a single bond is interposed between a multiple bond; unshared electron pairs of a nitrogen atom, an oxygen atom, a sulfur atom, or a phosphorus atom; a vacant p orbital that a boron atom has; or a d orbital for a sigma bonding that a silicon atom has and this structure continuously connects)/(The number of total atoms in the mother skeleton or the main chain)}×100

The organic compound having at least one of the ionic group and the polar group contained in the electron injection layer may be used by mixing two or more organic compounds.

Examples of the ionic group that the organic compound contained in the electron injection layer has may include a group represented by the formula: —SM, a group represented by the formula: —C(=O)SM, a group represented by the formula: —CS$_2$M, a group represented by the formula: —OM, a group represented by the formula: —CO$_2$M, a group represented by the formula: —NM$_2$, a group represented by the formula: —NRM, a group represented by the formula: —PO$_3$M, a group represented by the formula: —OP(=O)(OM)$_2$, a group represented by the formula: —P(=O)(OM)$_2$, a group represented by the formula: —C(=O)NM$_2$, a group represented by the formula: —C(=O)NRM, a group represented by the formula: —C(=S)NRM, a group represented by the formula: —C(=S)NM$_2$, a group represented by the formula: —B(OM)$_2$, a group represented by the formula: —BR$_3$M, a group represented by the formula: —B(OR)$_3$M, a group represented by the formula: —SO$_3$M, a group represented by the formula: —SO$_2$M, a group represented by the formula: —NRC(=O)OM, a group represented by the formula: —NRC(=O)SM, a group represented by the formula: —NRC(=S)OM, a group represented by the formula: —NRC(=S)SM, a group represented by the formula: —OC(=O)NM$_2$, a group represented by the formula: —OC(=O)NRM, a group represented by the formula: —OC(=S)NM$_2$, a group represented by the formula: —OC(=S)NRM, a group represented by the formula: —SC(=O)NM$_2$, a group represented by the formula: —SC(=O)NRM, a group represented by the formula: —SC(=S)NM$_2$, a group represented by the formula: —SC(=S)NRM, a group represented by the formula: —NRC(=O)NM$_2$, a group represented by the formula: —NRC(=O)NRM, a group represented by the formula: —NRC(=S)NM$_2$, a group represented by the formula: —NRC(=S)NRM, a group represented by the formula: —NR$_3$M', a group represented by the formula: —PR$_3$M', a group represented by the formula: —OR$_2$M', a group represented by the formula: —SR$_2$M', a group represented by the formula: —IRM', a group made by a residual atom group represented by eliminating a hydrogen atom from an aromatic ring selected from the aromatic compounds represented by following formula (n-1) to formula (n-13) (In formulae, R represents a hydrogen atom or a hydrocarbyl group optionally having a substituent, M represents a metal cation or an ammonium cation that may have a substituent, and M' represents an anion).

(n-1)

(n-2)

(n-3)

(n-4)

(n-5)

(n-6)

-continued

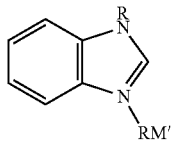 (n-7)

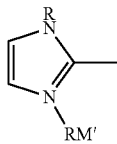 (n-8)

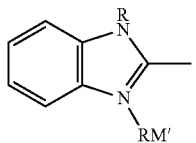 (n-9)

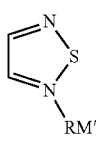 (n-10)

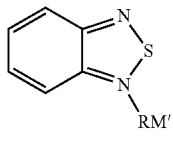 (n-11)

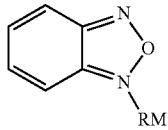 (n-12)

 (n-13)

Other metal cation other than the metal cation represented by M may be accompanied or an anion may be accompanied in these groups so that charge of the total ionic groups is balanced to be zero.

The hydrocarbyl group optionally having a substituent represented by R is a similar group to the hydrocarbyl group optionally having a substituent represented by $R^3$ to $R^9$.

A monovalent, a divalent or a trivalent ion is preferable as the metal cation represented by M. Examples of the metal cation represented by M may include ions of metals such as Li, Na, K, Cs, Be, Mg, Ca, Ba, Ag, Al, Bi, Cu, Fe, Ga, Mn, Pb, Sn, Ti, V, W, Y, Yb, Zn, and Zr. As the metal cation represented by M, ions of Li, Na, K, Cs, Mg, Ca, Ag, and Al are preferable; ions of Li, Na, K, Cs, Mg, and Ca are more preferable; and ions of Li, Na, K, and Cs are further preferable.

Examples of a substituent that an ammonium cation represented by M may have may include alkyl groups having 1 to 10 carbon atoms such as a methyl group, an ethyl group, a propyl group, an isopropyl group, a butyl group, an isobutyl group, a sec-butyl group, and a tert-butyl group.

Examples of the anion represented by M' may include $F^-$, $Cl^-$, $Br^-$, $I^-$, $OH^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$, $PF_6^-$, $CH_3SO_3^-$, $CF_3SO_3^-$, $[(CF_3SO_2)_2N]^-$, a tetrakis(imidazolyl) borate anion, an 8-quinolinolato anion, a 2-methyl-8-quinolinolato anion, and a 2-phenyl-8-quinolinolato anion. As the anion represented by M', $F^-$, $Cl^-$, $Br^-$, $I^-$, $BF_4^-$, $PF_6^-$, $CH_3SO_3^-$, $CF_3SO_3^-$, $[(CF_3SO_2)_2N^-]$, and the tetrakis(imidazolyl)borate anion are preferable; $BF_4^-$, $PF_6^-$, $CH_3SO_3^-$, $CF_3SO_3^-$, $[(CF_3SO_2)_2N]^-$, and the tetrakis(imidazolyl)borate anion are more preferable; and $CH_3SO_3^-$, $CF_3SO_3^-$, $[(CF_3SO_2)_2N]^-$, and the tetrakis(imidazolyl)borate anion are further preferable.

Preferable examples of the ionic group may include the group represented by the formula: —SM, the group represented by the formula: —OM, the group represented by the formula: —CO$_2$M, the group represented by the formula: —NM$_2$, the group represented by the formula: —NRM, the group represented by the formula: —PO$_3$M, the group represented by the formula: —OP(=O)(OM)$_2$, the group represented by the formula: —P(=O)(OM)$_2$, the group represented by the formula: —C(=O)NM$_2$, the group represented by the formula: —C(=O)NRM, the group represented by the formula: —SO$_3$M, the group represented by the formula: —SO$_2$M, the group represented by the formula: —NR$_3$M', and the group represented by formula (n-1), formula (n-5) to formula (n-8), and formula (n-13). More preferable examples of the ionic group may include the group represented by the formula: —CO$_2$M, the group represented by the formula: —PO$_3$M, the group represented by the formula: —OP(=O)(OM)$_2$, the group represented by the formula: —P(=O)(OM)$_2$, the group represented by the formula: —SO$_3$M, the group represented by the formula: —SO$_2$M, the group represented by the formula: —NR$_3$M', and the group represented by formula (n-1), formula (n-5), and formula (n-13). Further preferable examples of the ionic group may include the group represented by the formula: —CO$_2$M, the group represented by the formula: —SO$_3$M, the group represented by the formula: —SO$_2$M, the group represented by the formula: —NR$_3$M', and the group represented by formula (n-1) and formula (n-5). Particularly preferable examples of the ionic group may include the group represented by the formula: —CO$_2$M and the group represented by the formula: —SO$_3$M. Especially preferable example of the ionic group may include the group represented by the formula: —CO$_2$M.

Examples of the polar group that the organic compound contained in the electron injection layer has may include a carboxy group, a sulfo group, a hydroxy group, a mercapto group, an amino group, a hydrocarbylamino group, a cyano group, a pyrrolidonyl group, a monovalent heterocyclic group, and a group represented by the following formula (I) to formula (IX).

 (I)

 (II)

 (III)

 (IV)

 (V)

 (VI)

 (VII)

—C(=O)—O—(R'O)$_q$—R" (VIII)

—NHC(=O)—(R'NHC(=O))$_q$—R" (IX)

In formula (I) to formula (IX), R' represents a hydrocarbylene group optionally having a substituent. R" represents a hydrogen atom, a hydrocarbyl group optionally having a substituent, a carboxy group, a sulfo group, hydroxy group, a mercapto group, an amino group, a group represented by —NR$^c_2$, a cyano group, or group represented by —C(=O)NR$^c_2$. R'" represents a trivalent hydrocarbon group optionally having a substituent. m represents an integer of 1 or more. q represents an integer of zero or more. R$^c$ represents an alkyl group having 1 to 30 carbon atoms optionally having a substituent, or an aryl group having 6 to 50 carbon atoms optionally having a substituent. When R', R", and R'" are each plurally present, each R', R", and R'" may be the same as or different from each other.

The hydrocarbylamino group is an amino group in which one of the hydrogen atoms constituting the amino group is substituted by a hydrocarbyl group optionally having a substituent. Examples of the hydrocarbylamino group may include a methylamino group, an ethylamino group, a propylamino group, an isopropylamino group, a butylamino group, an isobutylamino group, a sec-butylamino group, a tert-butylamino group, a pentylamino group, a hexylamino group, a heptylamino group, an octylamino group, a 2-ethylhexylamino group, a nonylamino group, a decylamino group, a 3,7-dimethyloctylamino group, a dodecylamino group, a trifluoromethylamino group, a phenylamino group, a 1-naphthylamino group, a 2-naphthylamino group, 2-methylphenylamino group, a 3-methylphenylamino group, a 4-methylphenylamino group, a 4-ethylphenylamino group, a 4-propylphenylamino group, a 4-isopropylphenylamino group, a 4-butylphenylamino group, a 4-tert-butylphenylamino group, a 4-hexylphenylamino group, a 4-cyclohexylphenylamino group, a 4-adamantylphenylamino group, and a 4-phenylphenylamino group.

The monovalent heterocyclic group is a similar group to the monovalent heterocyclic group being a substituent that the hydrocarbyl group represented by R$^3$ to R$^9$ as previously described can have.

In formula (I) to formula (IX), examples of the hydrocarbylene group represented by R' may include saturated hydrocarbylene groups having 1 to 50 carbon atoms such as a methylene group, an ethylene group, a 1,2-propylene group, a 1,3-propylene group, a 1,2-butylene group, a 1,3-butylene group, a 1,4-butylene group, a 1,5-pentylene group, a 1,6-hexylene group, a 1,9-nonylene group, and a 1,12-dodecylene group; unsaturated hydrocarbylene groups having 2 to 50 carbon atoms such as an ethenylene group, a propenylene group, a 3-butenylene group, a 2-pentenylene group, a 2-hexenylene group, a 2-nonenylene group, and a 2-dodecenylene group; cyclic saturated hydrocarbylene groups having 3 to 50 carbon atoms such as a cyclopropylene group, a cyclobutylene group, a cyclopentylene group, a cyclohexylene group, a cyclononylene group, a cyclodocecylene group, a norbornylene group, and an adamantylene group; alkenylene groups having 2 to 50 carbon atoms such as an ethenylene group, a propenylene group, a 3-butenylene group, a 2-butenylene, a 2-pentenylene group, a 2-hexenylene group, a 2-nonenylene group, and a 2-dodecenylene group; and arylene groups having 6 to 50 carbon atoms such as a 1,3-phenylene group, 1,4-phenylene, a 1,4-naphthylene group, a 1,5-naphthylene group, a 2,6-naphthylene group, and a biphenyl-4,4'-diyl group.

R' may have a substituent. The substituent may be the same as the substituent that the hydrocarbyl group represented by R$^3$ to R$^9$ as previously described can have. When the substituents are plurally present, the substituents may be the same as or different from each other.

Examples of the hydrocarbyl group represented by R" in formula (I) to formula (IX) may include alkyl groups having 1 to 20 carbon atoms such as a methyl group, an ethyl group, a propyl group, an isopropyl group, a butyl group, an isobutyl group, a sec-butyl group, a tert-butyl group, a pentyl group, a hexyl group, a cyclohexyl group, a heptyl group, an octyl group, a nonyl group, a decyl group, and a lauryl group; and aryl groups having 6 to 30 carbon atoms such as a phenyl group, a 1-naphthyl group, a 2-naphthyl group, a 1-anthracenyl group, a 2-anthracenyl group, and a 9-anthracenyl group. Since solubility of a solvent is excellent, the methyl group, the ethyl group, the phenyl group, the 1-naphthyl group, and the 2-naphthyl group are preferable as R". R" may have a substituent. As the substituent, the same substituent as the substituent that the hydrocarbyl group represented by R$^3$ to R$^9$ as previously described can have may be included. When the substituents are plurally present, the substituents may be the same as or different from each other.

In formula (I) to formula (IX), a trivalent hydrocarbon group represented by R'" and optionally having a substituent is usually a group having 1 to 50 carbon atoms and preferably a group having 1 to 30 carbon atoms. Examples of the trivalent hydrocarbon group optionally having a substituent may include unsubstituted alkanetriyl groups having 1 to 20 carbon atoms such as a methanetriyl group, an ethanetriyl group, a 1,2,3-propanetriyl group, a 1,2,4-butanetriyl group, a 1,2,5-pentanetriyl group, a 1,3,5-pentanetriyl group, a 1,2,6-hexanetriyl group, and a 1,3,6-hexanetriyl group, and substituted alkanetriyl groups in which at least one hydrogen atom in these groups is substituted; unsubstituted trivalent aromatic ring groups having 6 to 30 carbon atoms such as a 1,2,3-benzenetriyl group, a 1,2,4-benzenetriyl group, and a 1,3,5-benzenetriyl group, and groups in which at least one hydrogen atom in these groups is substituted. Since solubility of the conjugated compound into the solvent is excellent, the methanetriyl group, the ethanetriyl group, the 1,2,4-benzenetriyl group, and the 1,3,5-benzenetriyl group are preferable.

In formula (I) to formula (IX), since solubility of the solvent is excellent, a methyl group, a ethyl group, a phenyl group, a 1-naphthyl group, and a 2-naphthyl group are preferable as R$^c$.

In formula (I) and formula (II), m represents an integer of 1 or more. m is preferably 1 to 20, more preferably 3 to 20, further preferably 3 to 15, and particularly preferably 6 to 10.

In formula (III) to formula (IX), q represents an integer of 0 or more. In formula (III), q is preferably 0 to 30, more preferably 3 to 20, further preferably 3 to 10, and particularly preferably 6 to 10. In formula (IV) to formula (VII), q is preferably 0 to 30, more preferably 0 to 20, further preferably 0 to 10, and particularly preferably 0 to 5. In formula (VIII), q is preferably 0 to 30, more preferably 0 to 20, further preferably 3 to 20, and particularly preferably 3 to 10. In formula (IX), q is preferably 0 to 30, more preferably 0 to 20, further preferably 0 to 15, and particularly preferably 0 to 10.

Preferable examples of the polar group may include a carboxy group, a sulfo group, hydroxy group, a mercapto group, an amino group, a hydrocarbylamino group, a cyano group, a pyrrolidonyl group, a monovalent heterocyclic group, a group represented by formula (I), and a group represented by formula (II). More preferable examples may include the carboxy group, the sulfo group, the hydroxy group, the mercapto group, the amino group, the hydrocarbylamino group, the cyano group, the pyrrolidonyl group, a pyridyl group, a 1,3,5-triazyl group, and the group represented by formula (I). Further preferable examples may include the carboxy group, the sulfo group, the mercapto group, the amino group, the pyrrolidonyl group, the pyridyl group, and the group represented by formula (I). Particularly preferable examples may include the carboxy group, the mercapto group, the amino group, the pyrrolidonyl group, the pyridyl group, and the group represented by formula (I). Especially preferable examples may include the carboxy group, the mercapto group, the pyridyl group, and the group represented by formula (I). Extremely preferable example may include the group represented by formula (I).

The conjugated compound that the electron injection layer 44 contains preferably has, for example, a group represented by formula (X) or a structural unit represented by formula (XI), or has both of them.

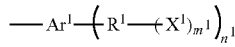

(X)

In formula (X), $Ar^1$ represents an aromatic group having a valence of $(n^1+1)$. $R^1$ represents a direct bond or a group having a valence of $(m^1+1)$. $X^1$ represents a group having at least one of an ionic group and a polar group. $m^1$ and $n^1$ are each independently an integer of 1 or more. When $R^1$ is a direct bond, $m^1$ is 1. When $R^1$, $X^1$ and $m^1$ are each plurally present, each $R^1$, $X^1$, and $m^1$ may be the same as or different from each other.

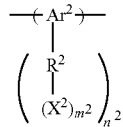

(XI)

In formula (XI), $Ar^2$ represents an aromatic group having a valence of $(n^2+2)$; $R^2$ represents a direct bond or a group having a valence of $(m^2+1)$; and $X^2$ represents a group having at least one of an ionic group and a polar group. $m^2$ and $n^2$ are each independently an integer of 1 or more; when $R^2$ is a direct bond, $m^2$ is 1. When $R^2$, $X^2$ and $m^2$ are each plurally present, each $R^2$, $X^2$ and $m^2$ may be the same as or different from each other.

In formula (X), an aromatic group represented by $Ar^1$ having a valence of $(n^1+1)$ refers to a residual atom group (a residual group) in which $(n^1+1)$ hydrogen atoms are eliminated from an aromatic ring in the aromatic compound having the aromatic ring, and a group optionally having a substituent.

In formula (XI), an aromatic group represented by $Ar^2$ having a valence of $(n^2+2)$ means a residual atom group (a residual group) in which $(n^2+2)$ hydrogen atoms are eliminated from an aromatic ring in the aromatic compound having the aromatic ring, and a group optionally having a substituent.

Examples of the aromatic compounds described above may include organic compounds represented by formula (1) to formula (95). Since synthesizing is easy, as the aromatic compounds described above, the organic compounds represented by formula (1) to formula (12), formula (15) to formula (22), formula (24) to formula (31), formula (37) to formula (40), formula (43) to formula (46), formula (49), formula (50), formula (59) to formula (76), and formula (92) to formula (95) are preferable; the organic compounds represented by formula (1) to formula (3), formula (8) to formula (10), formula (15) to formula (21), formula (24) to formula (31), formula (37), formula (39), formula (43) to formula (45), formula (49), formula (50), formula (59) to formula (76), and formula (92) to formula (95) are more preferable; the organic compounds represented by formula (1) to formula (3), formula (8), formula (10), formula (15), formula (17), formula (21), formula (24), formula (30), formula (59), formula (60), and formula (61) are further preferable; the organic compounds represented by formula (1) to formula (3), formula (8), formula (10), and formula (59) are particularly preferable; and the organic compounds represented by formula (1), formula (2), formula (8) and formula (59) are especially preferable.

(1)

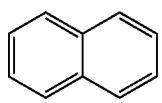

(2)

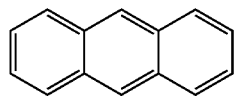

(3)

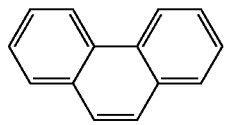

(4)

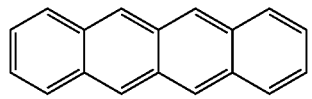

(5)

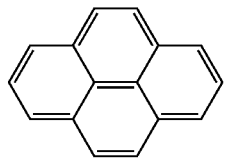

(6)

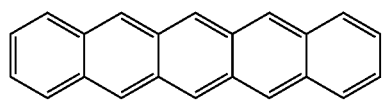

(7)

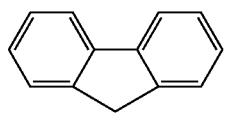

(8)

-continued
(9)
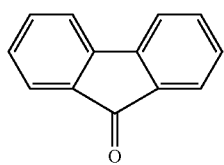
(10)
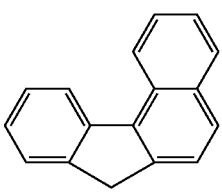
(11)
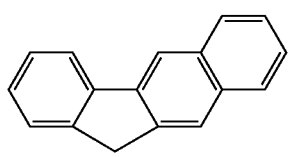
(12)
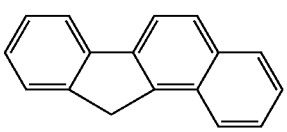
(13)
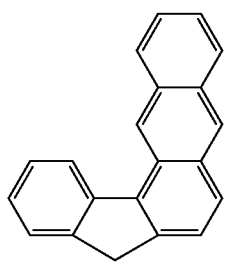
(14)
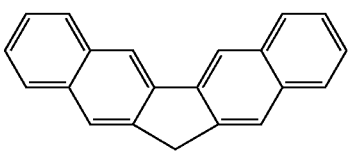
(15)
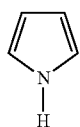
(16)
(17)
(18)
(19)
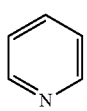
(20)
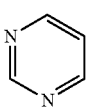
(21)
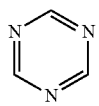
(22)
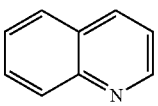
(23)
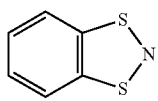
(24)
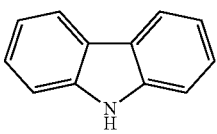
(25)
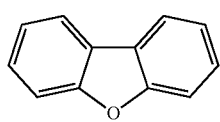
(26)
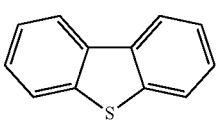
(27)
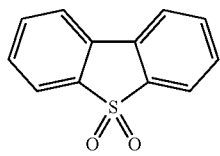
(28)
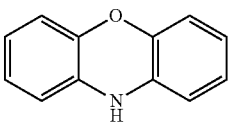

-continued
(29) 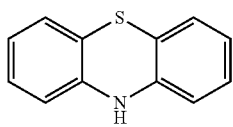
(30) 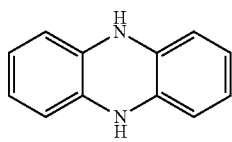
(31) 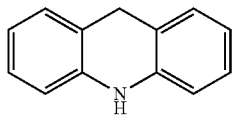
(32) 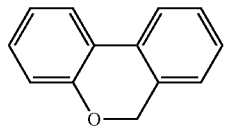
(33) 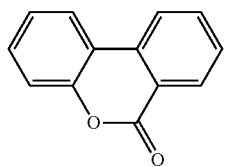
(34) 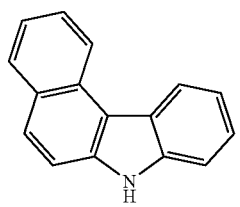
(35) 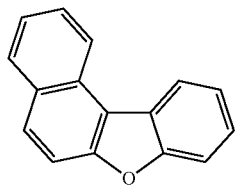
(36) 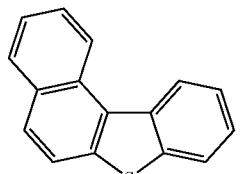
(37) 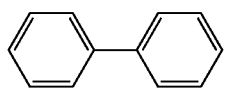
(38) 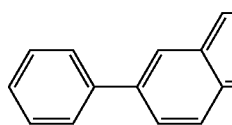
(39) 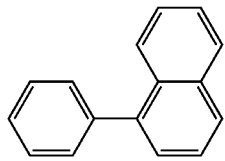
(40) 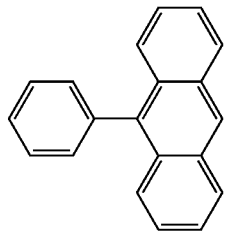
(41) 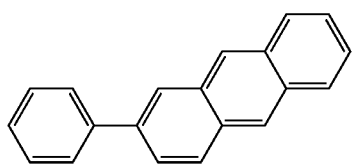
(42) 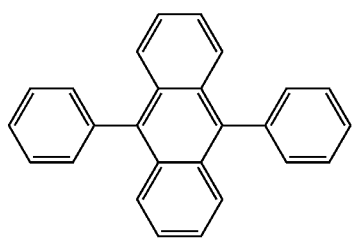
(43) 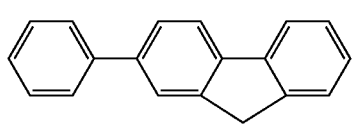
(44) 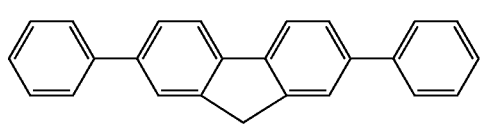
(45) 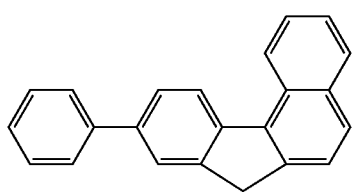
(46) 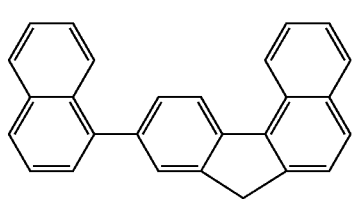

-continued
(47)
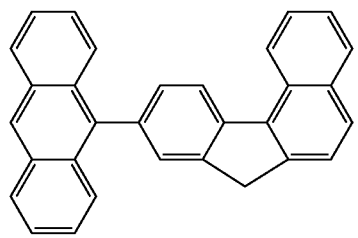
(48)
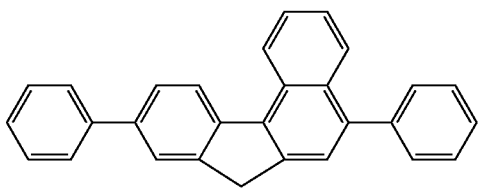
(49)
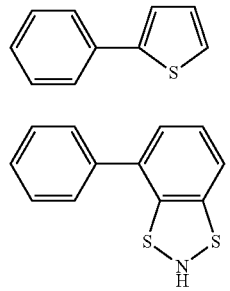
(50)
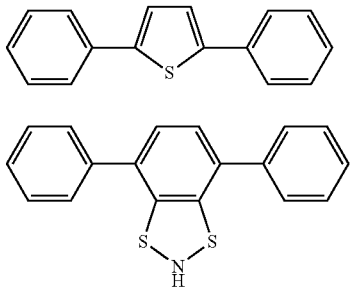
(51)
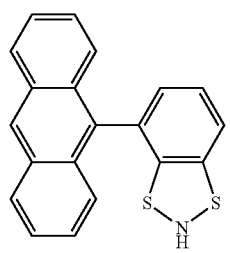
(52)
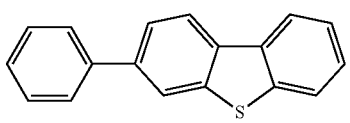
(53)
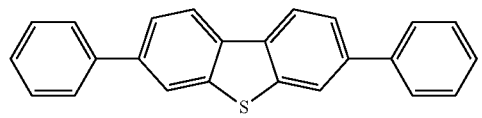
(54)
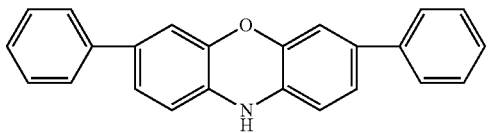
(55)
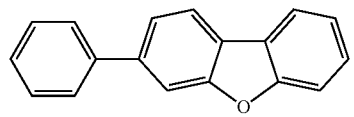
(56)
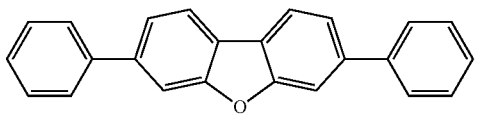
(57)
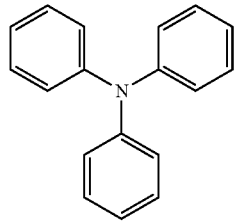
(58)
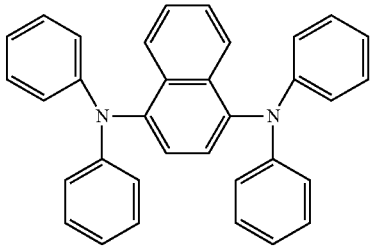
(59)
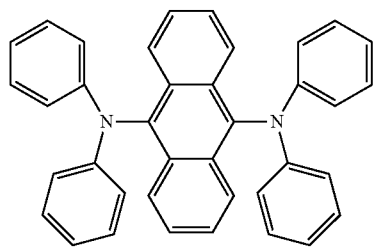
(60)
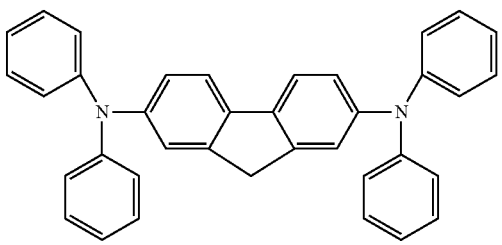

(63)
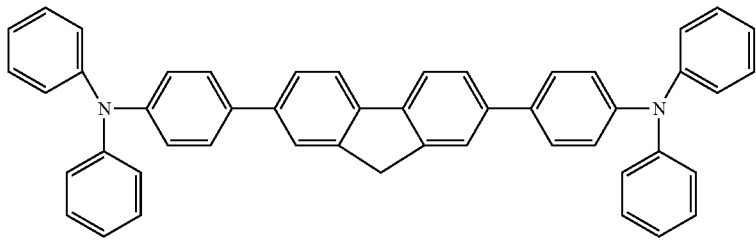
(64)
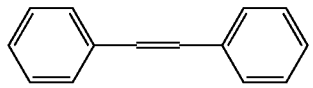
(65)
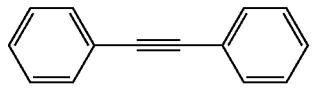
(66)
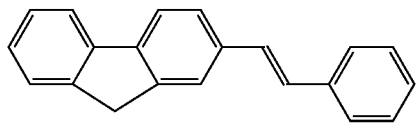
(67)
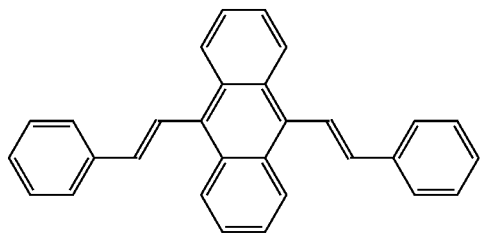
(68)
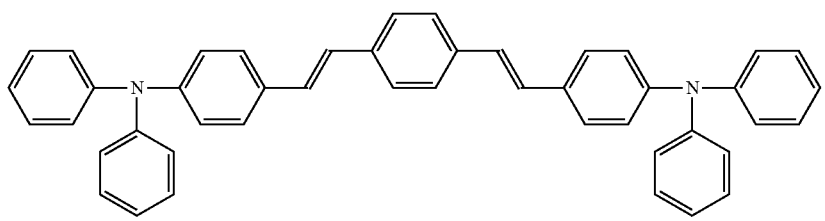
(69)
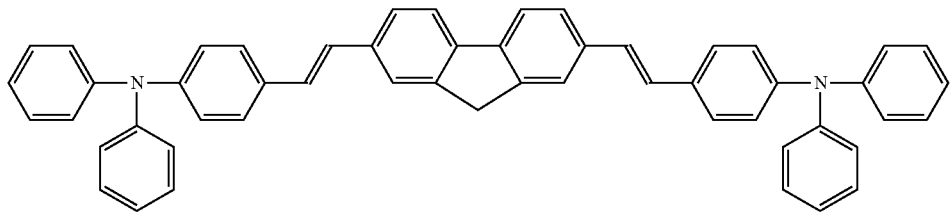
(70)
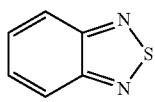
(71)
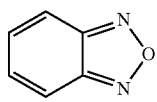
(72)
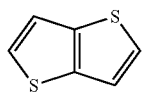
(73)
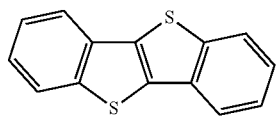
(74)
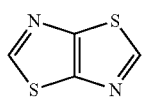
(75)
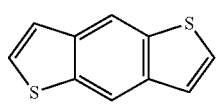
(76)
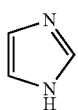
(77)
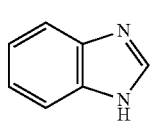

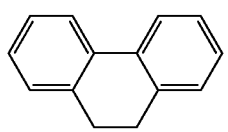
(78)

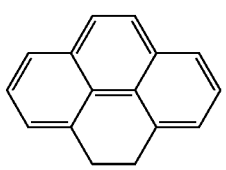
(79)

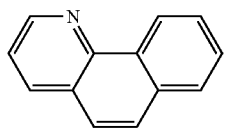
(80)

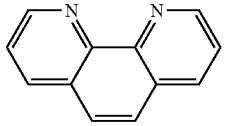
(81)

(82)

(83)

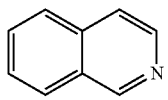
(84)

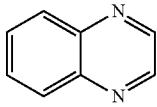
(85)

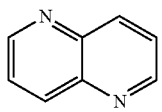
(86)

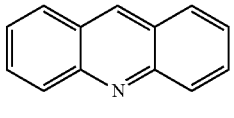
(87)

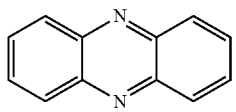
(88)

(89)

(90)

(91)

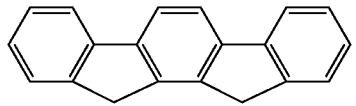
(92)

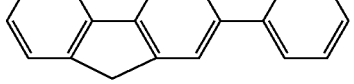
(93)

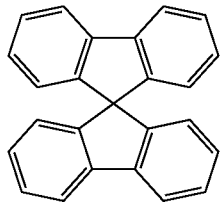
(94)

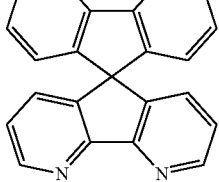
(95)

One or more hydrogen atoms in these aromatic compounds may be substituted by a substituent. Examples of the substituent may include a halogen atom, a hydrocarbyl group optionally having a substituent, a mercapto group, a mercaptocarbonyl group, a mercaptothiocarbonyl group, a hydrocarbylthio group optionally having a substituent, a hydrocarbylthiocarbonyl group optionally having a substituent, a hydrocarbyldithio group optionally having a substituent, a hydroxy group, a hydrocarbyloxy group optionally having a substituent, a carboxy group, a hydrocarbylcarbonyl group optionally having a substituent, an amino group, a hydrocarbylamino group in which hydrogen(s) in the hydrocarbyl group may be substituted by substituent(s), an dihydrocarbylamino group in which hydrogen(s) in the hydrocarbyl group may be substituted by substituent(s), a phosphino group, a hydrocarbylphosphino group in which hydrogen(s) in the hydrocarbyl group may be substituted by substituent(s), a dihydrocarbylphosphino group in which hydrogen(s) in the hydrocarbyl group may be substituted by substituent(s), a monovalent heterocyclic group, a formyl group, a hydrocarbyloxycarbonyl group optionally having a substituent, a hydrocarbylcarbonyloxy group optionally having a substituent, a nitro group, a group represented by the formula: —OP(=O)(OH)$_2$, a group represented by the formula: —P(=O)(OH)$_2$, a carbamoyl group, a hydrocarbylcarbamoyl group in which hydrogen(s) in the hydrocarbyl group may be substituted by substituent(s), a dihydrocarbylcarbamoyl group in which hydrogen(s) in the hydrocarbyl group are optionally substituted by substituent(s), a group represented by the formula: —C(=S)NR$_2$, a group represented by the formula: —B(OH)$_2$, a group represented by the formula: —BR$_2$, a boric acid ester residual group, a group represented by the formula: —Si(OR)$_3$, a sulfo group, a hydrocarbylsulfo group optionally having a substituent, a hydrocarbyl sulfonyl group optionally having a substituent, a sulfino group, a hydrocarbylsulfino group optionally having a substituent, a group represented by the formula: —NRC(=O)OR, a group represented by the formula: —NRC(=O)SR, a group represented by the formula: —NRC(=S)OR, a group represented by the formula: —NRC(=S)SR, a group represented by the formula: —OC(=O)NR$_2$, a group represented by the formula: —SC(=O)NR$_2$, a group represented by the formula: —OC(=S)NR$_2$, a group represented by the formula: —SC(=S)NR$_2$, a group represented by the formula: —NRC(=O)NR$_2$, and a group represented by the formula: —NRC(=S)NR$_2$.

In the groups represented by the formulae described above, R represents a hydrogen atom, or a hydrocarbyl group optionally having a substituent. The plurally present substituents may form a ring by bonding with each other.

Examples of the halogen atom being a substituent that the above described aromatic compound may have may include a fluorine atom, a chlorine atom, a bromine atom, and an iodine atom. The fluorine atom, the chlorine atom, and the bromine atom are preferable as the halogen atom that the aromatic compound can have.

Examples of the hydrocarbyl group optionally having a substituent being a substituent that the above described aromatic compound may have may include alkyl groups having 1 to 50 carbon atoms such as a methyl group, an ethyl group, a propyl group, an isopropyl group, a butyl group, an isobutyl group, a sec-butyl group, a tert-butyl group, a pentyl group, a hexyl group, a nonyl group, a dodecyl group, a pentadecyl group, an octadecyl group, and a docosyl group; cyclic saturated hydrocarbyl groups having 3 to 50 carbon atoms such as a cyclopropyl group, a cyclobutyl group, a cyclopentyl group, a cyclohexyl group, a cyclononyl group, a cyclododecyl group, a norbornyl group, and an adamantyl group; alkenyl groups having 2 to 50 carbon atoms such as an ethenyl group, a propenyl group, a 3-butenyl group, a 2-butenyl group, a 2-pentenyl group, a 2-hexenyl group, a 2-nonenyl group, and a 2-dodecenyl group; aryl groups having 6 to 50 carbon atoms such as a phenyl group, a 1-naphthyl group, a 2-naphthyl group, a 2-methylphenyl group, a 3-methylphenyl group, a 4-methylphenyl group, a 4-ethylphenyl group, a 4-propylphenyl group, a 4-isopropylphenyl group, a 4-butylphenyl group, a 4-tert-butylphenyl group, a 4-hexylphenyl group, a 4-cyclohexylphenyl group, a 4-adamantylphenyl group, and 4-phenylphenyl group; and arylalkyl groups having 7 to 50 carbon atoms such as a phenylmethyl group, a 1-phenyleneethyl group, a 2-phenylethyl group, a 1-phenyl-1-propyl group, a 1-phenyl-2-propyl group, a 2-phenyl-2-propyl group, a 3-phenyl-1-propyl group, a 4-phenyl-1-butyl group, a 5-phenyl-1-pentyl group, and a 6-phenyl-1-hexyl group. As the hydrocarbyl group, the alkyl groups having 1 to 50 carbon atoms and the aryl groups having 6 to 50 carbon atoms are preferable; alkyl groups having 1 to 12 carbon atoms and aryl groups having 6 to 18 carbon atoms are more preferable; and alkyl groups having 6 to 12 carbon atoms and aryl groups having 6 to 12 carbon atoms are further preferable.

The hydrocarbylthio group optionally having a substituent being a substituent that the above described aromatic compound may have is a thio group in which a part of or all of one to three hydrogen atoms, especially one or two hydrogen atoms, constituting the group is or are substituted by hydrocarbyl group(s), optionally having a substituent, which the above described aromatic compound may have (hereinafter, referred to as the "above described hydrocarbyl group"). The hydrocarbylthiocarbonyl group optionally having a substituent being a substituent that the above described aromatic compound may have is a thiocarbonyl group in which a part of or all of one to three hydrogen atoms, especially one or two hydrogen atoms, constituting the group is or are substituted by the above described hydrocarbyl group(s). The hydrocarbyldithio group optionally having a substituent being a substituent that the above described aromatic compound may have is a dithio group in which a part of or all of one to three hydrogen atoms, especially one or two hydrogen atoms, constituting the group is or are substituted by the above described hydrocarbyl groups. The hydrocarbyloxy group optionally having a substituent being a substituent that the above described aromatic compound may have is an oxy group in which a part of or all of one to three hydrogen atoms, especially one or two hydrogen atoms, constituting the group is or are substituted by the above described hydrocarbyl group(s). The hydrocarbylcarbonyl group optionally having a substituent being a substituent that the above described aromatic compound may have is a carbonyl group in which a part of or all of one to three hydrogen atoms, especially one or two hydrogen atoms, constituting the group is or are substituted by the above described hydrocarbyl groups. The hydrocarbyloxycarbonyl group optionally having a substituent being a substituent that the above described aromatic compound may have is an oxycarbonyl group in which a part of or all of one to three hydrogen atoms, especially one or two hydrogen atoms, constituting the group is or are substituted by the above described hydrocarbyl group(s). The hydrocarbylcarbonyloxy group optionally having a substituent being a substituent that the above described aromatic compound may have is a carbonyloxy group in which a part of or all of one to three hydrogen atoms, especially one or two hydrogen atoms, constituting the group is or are substituted by the above described hydrocarbyl group(s).

The hydrocarbylamino group in which a hydrogen atoms in the hydrocarbyl group is optionally substituted by a substituents and the dihydrocarbylamino group in which a hydrogen atom in the hydrocarbyl group may be substituted by a substituents being a substituent that the above described aromatic compound may have are amino groups in which one or two hydrogen(s) constituting each group is or are substituted by the above described hydrocarbyl group(s). The hydrocarbylphosphino group optionally having a substituent and the dihydrocarbylphosphino group optionally having a substituent that the above described aromatic compound may have are phosphino groups in which one or two hydrogens constituting each group is or are substituted by the above described hydrocarbyl group(s).

The hydrocarbylcarbamoyl group in which a hydrogen atom in the hydrocarbyl group is optionally substituted by a substituent and the dihydrocarbylcarbamoyl group in which a hydrogen atom in the hydrocarbyl group is optionally substituted by a substituent being a substituent that the above described aromatic compound may have are carbamoyl groups in which one or two hydrogen(s) constituting each group is or are substituted by the above described hydrocarbyl group(s).

The group represented by the formula: —BR$_2$ and the group represented by the formula: —Si(OR)$_3$ being a substituent that the above described aromatic compound may have are groups in which R is a hydrogen atom or the above described hydrocarbyl group.

Examples of the boric acid ester residual group being a substituent that the above described aromatic compound may have may include groups selected from the group consisting of the group represented by the following formulae.

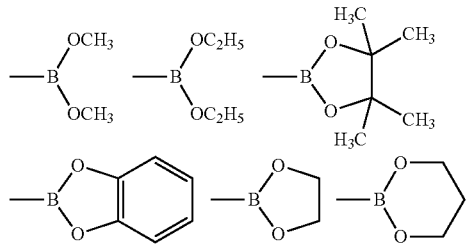

The hydrocarbylsulfo group optionally having a substituent being a substituent that the above described aromatic compound may have is a sulfo group in which one or two hydrogen atom(s) constituting the group is or are substituted by the above described hydrocarbyl group(s). The hydrocarbylsulfonyl group optionally having a substituent being a substituent that the above described aromatic compound may have is a sulfonyl group in which one or two hydrogen atom(s) constituting the group is or are substituted by the above described hydrocarbyl group(s). The hydrocarbylsulfino group optionally having a substituent being a substituent that the above described aromatic compound may have is a sulfino group in which one or two hydrogen atom(s) constituting the group is or are substituted by the above described hydrocarbyl group(s).

The group represented by the formula: —NRC(=O)OR, the group represented by the formula: —NRC(=O)SR, the group represented by the formula: —NRC(=S)OR, the group represented by the formula: —NRC(=S)SR, the group represented by the formula: —OC(=O)NR$_2$, the group represented by the formula: —SC(=O)NR$_2$, the group represented by the formula: —OC(=S)NR$_2$, the group represented by the formula: —SC(=S)NR$_2$, the group represented by the formula: —NRC(=O)NR$_2$, and the group represented by the formula: —NRC(=S)NR$_2$ being substituents that the above described aromatic group may have are groups in which R is a hydrogen atom or the above described hydrocarbyl group.

The monovalent heterocyclic group being a substituent that the above described aromatic compound may have is a residual atom group in which on hydrogen atom is eliminated from the heterocyclic compound optionally having a substituent. Examples of the hetero ring of the heterocyclic compound may include monocyclic heterocycles such as a pyridine ring, a 1,2-diazine ring, a 1,3-diazine ring, a 1,4-diazine ring, a 1,3,5-triazine ring, a furan ring, a pyrrole ring, a thiophene ring, a pyrazole ring, an imidazole ring, an oxazole ring, a thiazole ring, an oxadiazole ring, a thiadiazole ring, an azadiazole ring; a fused multicyclic hetero ring in which two or more rings selected from monocyclic aromatic rings are fused; and a crosslinkage-having multicyclic aromatic ring having a structure in which two hetero rings, or one hetero ring and one aromatic ring are crosslinked through a divalent group such as a methylene group, an ethylene group and a carbonyl group. As the hetero rings, the pyridine ring, the 1,2-diazine ring, the 1,3-diazine ring, the 1,4-diazine ring, and the 1,3,5-triazine ring are preferable, and the pyridine ring and the 1,3,5-triazine ring are more preferable.

Preferable examples of the substituent that the above described aromatic compound may have may include the halogen atom, the hydrocarbyl group optionally having a substituent, the mercapto group, the hydrocarbylthio group optionally having a substituent, the hydrocarbyldithio group optionally having a substituent, the hydroxy group, the hydrocarbyloxy group optionally having a substituent, the carboxy group, the hydrocarbylcarbonyl group optionally having a substituent, the amino group, a hydrocarbylamino group in which hydrogen atom(s) in the hydrocarbyl group is or are optionally substituted by substituent(s), the dihydrocarbylamino group in which hydrogen(s) in the hydrocarbyl group are optionally substituted by substituent(s), the group represented by the formula: —OP(=O)(OH)$_2$, the sulfo group, and the monovalent heterocyclic group; more preferable examples may include the halogen atom, the hydrocarbyl group optionally having a substituent, the mercapto group, the hydroxy group, the hydrocarbyloxy group optionally having a substituent, the carboxy group, the amino group, the group represented by the formula: —P(=O)(OH)$_2$, the sulfo group, and the monovalent heterocyclic group; further preferable examples may include the hydrocarbyl group optionally having a substituent, the mercapto group, the hydrocarbyloxy group optionally having a substituent, the carboxy group, and a pyridyl group optionally having a substituent; and especially preferable examples may include the hydrocarbyl group optionally having a substituent and the hydrocarbyloxy group optionally having a substituent.

In formula (X), a group having at least one of the ionic group and the polar group represented by X' is the group having at least one of the ionic group and the polar group as previously described. Definition of the ionic group, definition of the polar group, specific examples thereof, and preferable examples thereof are as described above.

In formula (XI), a group having at least one of the ionic group and the polar group represented by $X^2$ is the group having at least one of the ionic group and the polar group as previously described. Definition of the ionic group, definition of the polar group, specific examples thereof, and preferable examples thereof are as described above.

In formula (X), examples of the group represented by $R^1$ and having a valence of $(m^1+1)$ may include a hydrocarbyl group optionally having a substituent being a substituent that the above described aromatic compound may have, a residual atom group in which $m^1$ hydrogen atom(s) are eliminated from a monovalent heterocyclic group being a substituent that the above described aromatic compound may have, and a group represented by the formula: —O—(R'O)$_m$—. These groups may form a ring. Preferable examples of the group represented by $R^1$ and having a valence of $(m^1+1)$ may include a residual atom group in which $m^1$ hydrogen atom(s) are eliminated from an alkyl group optionally having a substituent, a residual atom group in which $m^1$ hydrogen atom(s) are eliminated from an aryl group optionally having a substituent, a residual atom group in which $m^1$ hydrogen atom(s) are eliminated from a monovalent heterocyclic group, a residual atom group in which $m^1$ hydrogen atom(s) are eliminated from an alkyl group substituted by a monovalent heterocyclic group, and a residual atom group in which $m^1$ hydrogen atom(s) are eliminated from an aryl group substituted by a monovalent heterocyclic group; more preferable examples may include a residual atom group in which $m^1$ hydrogen atom(s) are eliminated from an alkyl group having 1 to 6 carbon atoms, a residual atom group in which $m^1$ hydrogen atom(s) are eliminated from a phenyl group, a residual atom group in which $m^1$ hydrogen atom(s) are eliminated from a triazinyl group, a residual atom group in which $m^1$ hydrogen atom(s) are eliminated from an alkyl group substituted by a triazinyl group, and a residual atom group in which $m^1$ hydrogen atom(s) are eliminated from an aryl group substituted by a triazinyl group; and further preferable examples may include a residual atom group in which $m^1$ hydrogen atom(s) are eliminated from a hexyl group, a residual atom group in which $m^1$ hydrogen atom(s) are eliminated from a phenyl group, and a residual atom group in which $m^1$ hydrogen atom(s) are eliminated from a phenyl group substituted by a triazinyl group.

In formula (XI), examples of the group represented by $R^2$ and having a valence of $(m^2+1)$ may include a hydrocarbyl group optionally having a substituent being a substituent that the above described aromatic compound may have, a residual atom group in which $m^2$ hydrogen atom(s) are eliminated from a monovalent heterocyclic group being a substituent that the above described aromatic compound may have, and a group represented by the formula: $—O—(R'O)_m—$. These groups may form a ring. Preferable examples of the group having a valence of $(m^2+1)$ may include a residual atom group in which $m^2$ hydrogen atom(s) are eliminated from an alkyl group optionally having a substituent, a residual atom group in which $m^2$ hydrogen atom(s) are eliminated from an aryl group optionally having a substituent, a residual atom group in which $m^2$ hydrogen atom(s) are eliminated from a monovalent heterocyclic group, a residual atom group in which $m^2$ hydrogen atom(s) are eliminated from an alkyl group substituted by a monovalent heterocyclic group, and a residual atom group in which $m^2$ hydrogen atom(s) are eliminated from an aryl group substituted by a monovalent heterocyclic group; more preferable examples may include a residual atom group in which $m^2$ hydrogen atom(s) are eliminated from an alkyl group having 1 to 6 carbon atoms, a residual atom group in which $m^2$ hydrogen atom(s) are eliminated from a phenyl group, a residual atom group in which $m^2$ hydrogen atom(s) are eliminated from a triazinyl group, a residual atom group in which $m^2$ hydrogen atom(s) are eliminated from an alkyl group substituted by a triazinyl group, and a residual atom group in which $m^2$ hydrogen atom(s) are eliminated from an aryl group substituted by a triazinyl group; and further preferable examples may include a residual atom group in which $m^2$ hydrogen atom(s) are eliminated from a hexyl group, a residual atom group in which $m^2$ hydrogen atom(s) are eliminated from a phenyl group, and a residual atom group in which $m^2$ hydrogen atom(s) are eliminated from a phenyl group substituted by a triazinyl group.

In the formulae, definition, specific examples, and preferable examples of R' and m are the same as the definition, the specific examples, and the preferable examples of R' and m in formula (I) to formula (IX) as described above.

A number average molecular weight, in terms of polystyrene, of the conjugated compound used as the electron injection material in the present invention is preferably $1\times10^3$ or more and $1\times10^7$ or less, and more preferably $1\times10^3$ or more and $1\times10^6$ or less. In the present invention, the number average molecular weight and a weight average molecular weight in terms of polystyrene can be determined by using a gel permeation chromatography (GPC).

Specific examples of the usable electron injection material for the electron injection layer 44 of the present invention may include a conjugated compound having a structural unit represented by following formula (c-1) to formula (c-37), formula (d-1) to formula (d-47), formula (e-1) to formula (e-16), formula (f-1) to formula (f-35), and formula (g-1) to formula (g-24). In these formulae, $n^3$ represents an integer of 2 or more, and is preferably an integer of 2 to 30, more preferably an integer of 2 to 20, and further preferably an integer of 6 to 10. $n^4$ represents an integer of 1 or more, and is preferably an integer of 1 to 10, and further preferably an integer of 2 to 6.

In these formulae, R represents a hydrogen atom, or a hydrocarbyl group optionally having a substituent. As R, an alkyl group having 1 to 6 carbon atoms is preferable, and a methyl group, an ethyl group, a propyl group, and a butyl group are further preferable.

In these specific examples of the electron injection material, one or more hydrogen atoms in the structural unit may be substituted by a substituent. Definition, specific examples, and preferable examples of the substituent are the same as the definition, the specific examples, and the preferable examples of the substituent represented by $R^3$ to $R^9$ that the hydrocarbyl group may have.

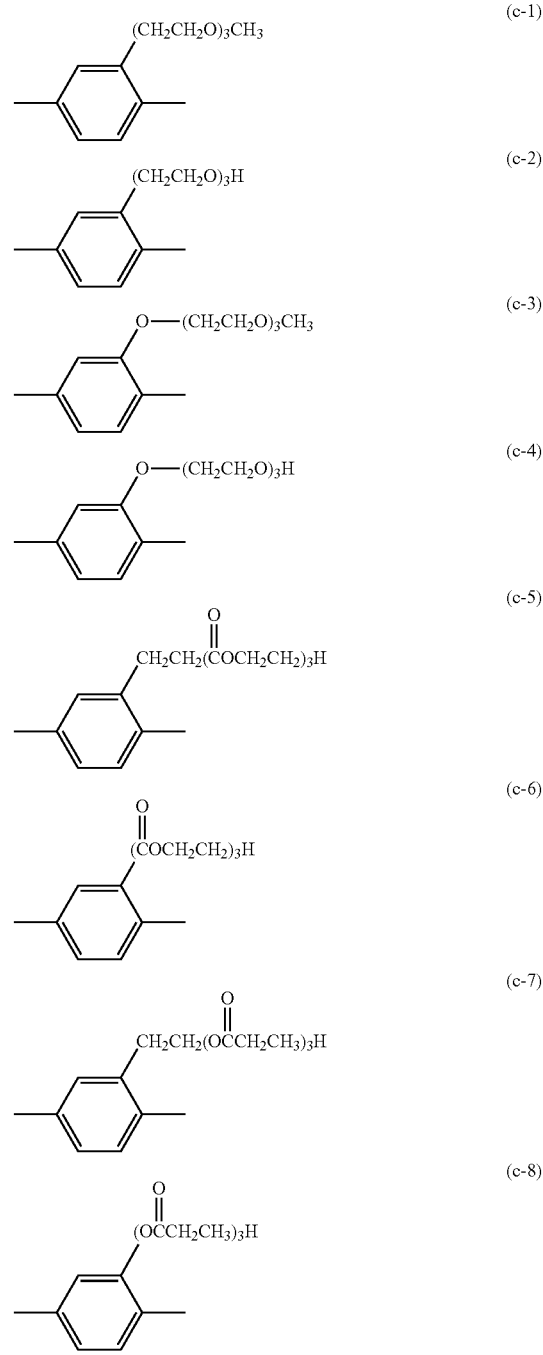

(c-9) 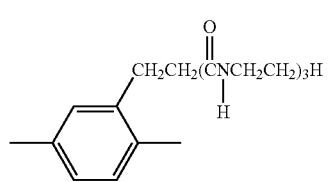
(c-10) 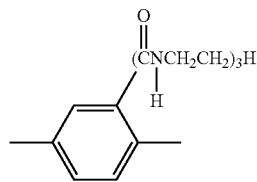
(c-11) 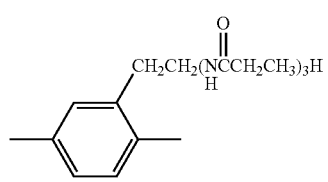
(c-12) 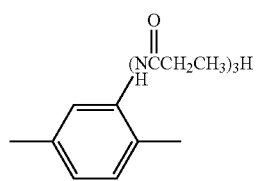
(c-13) 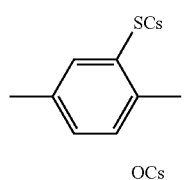
(c-14) 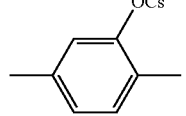
(c-15) 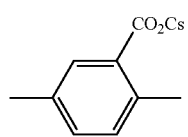
(c-16) 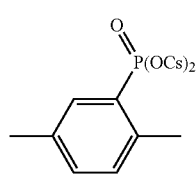
(c-17) 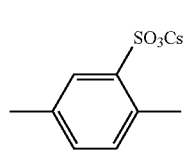
(c-18) 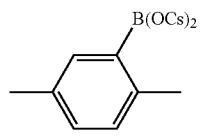
(c-19) 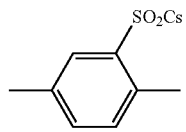
(c-20) 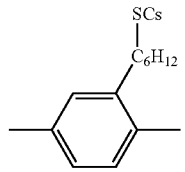
(c-21) 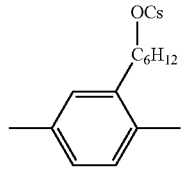
(c-22) 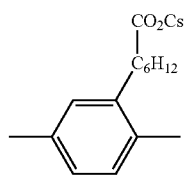
(c-23) 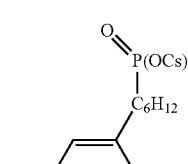
(c-24) 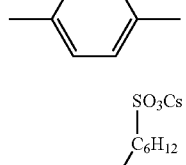
(c-25) 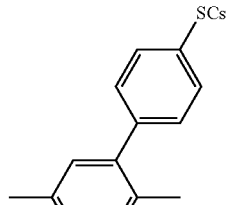
(c-26) 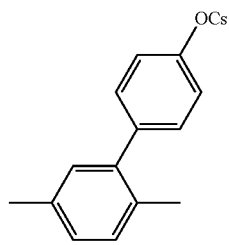

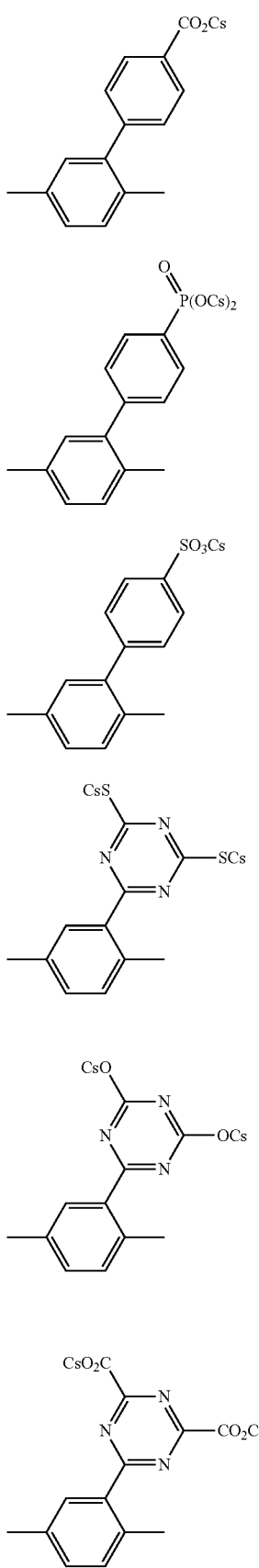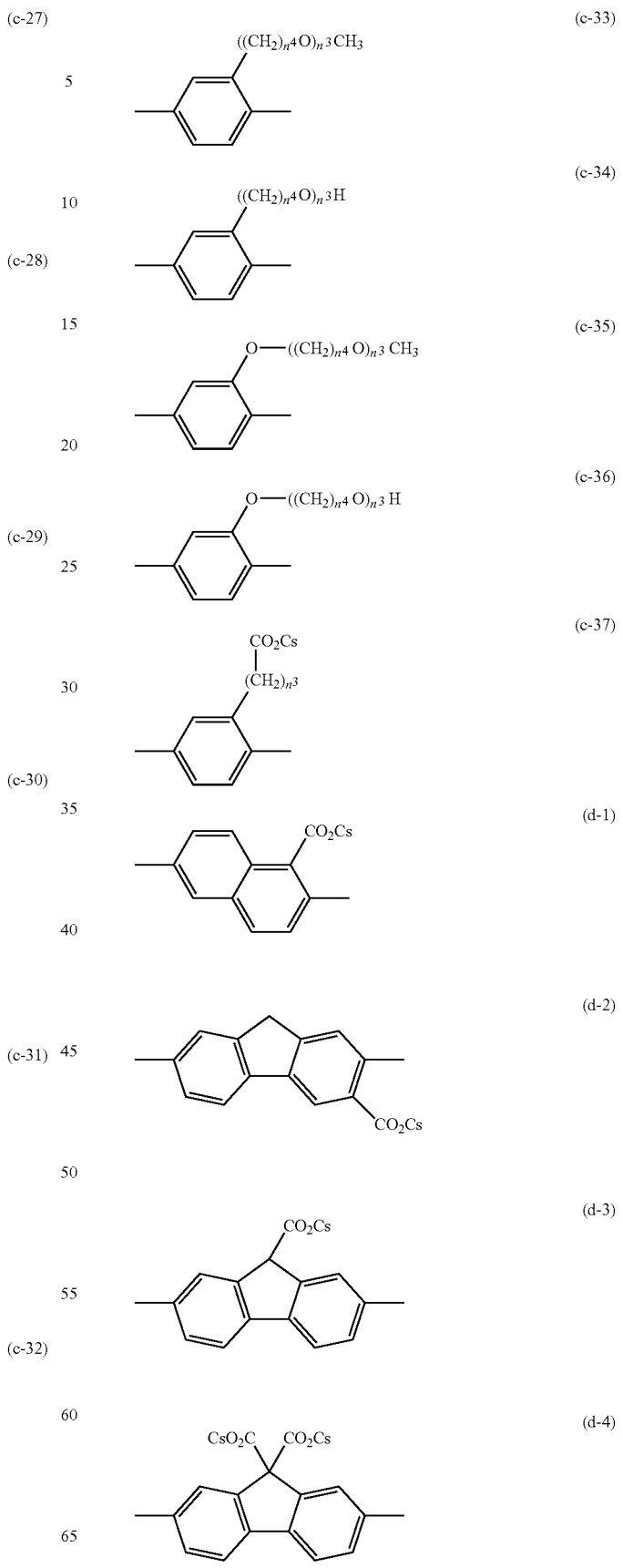

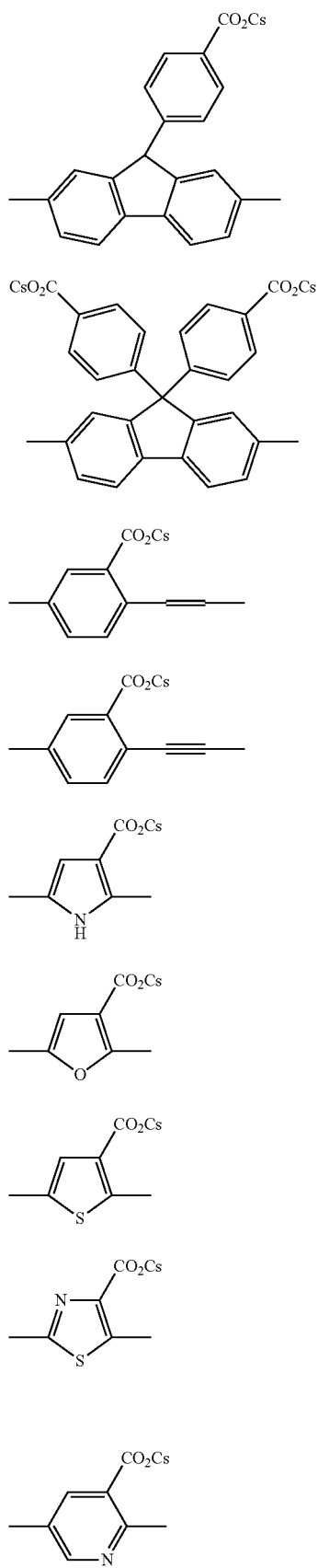
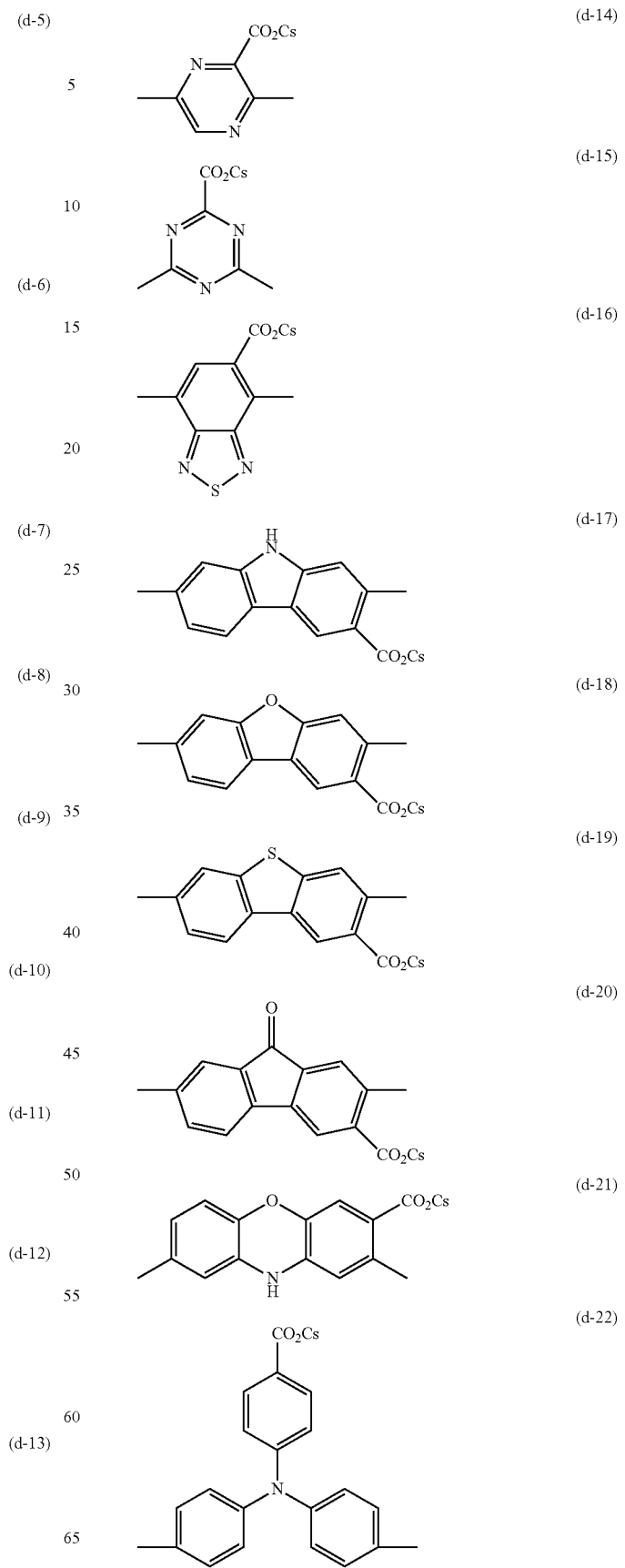

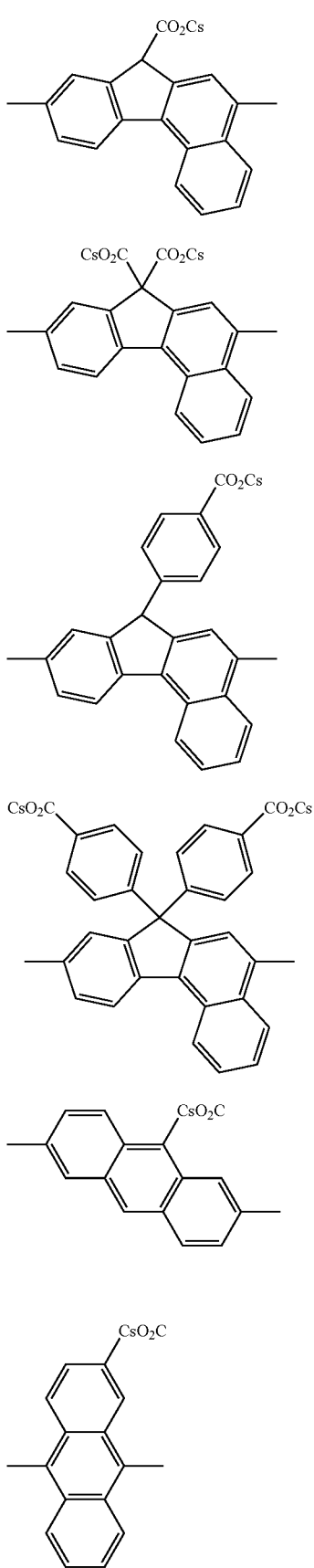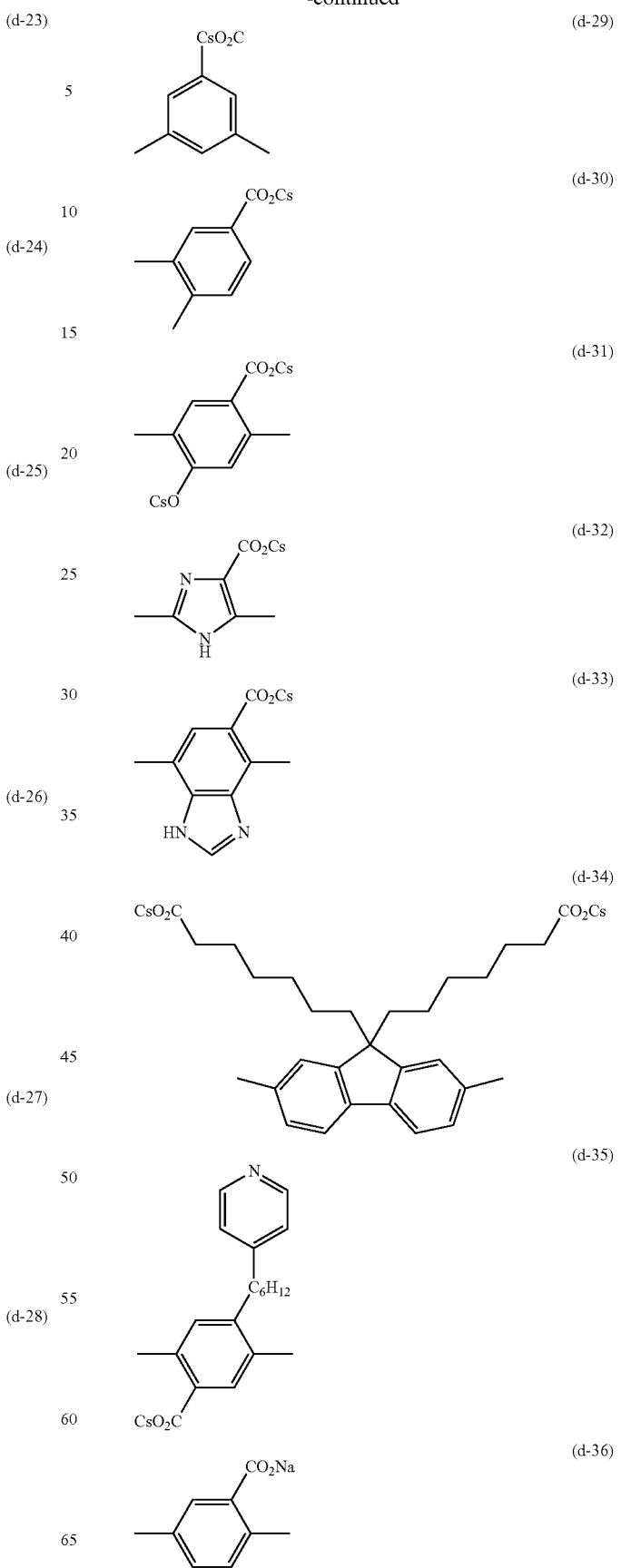

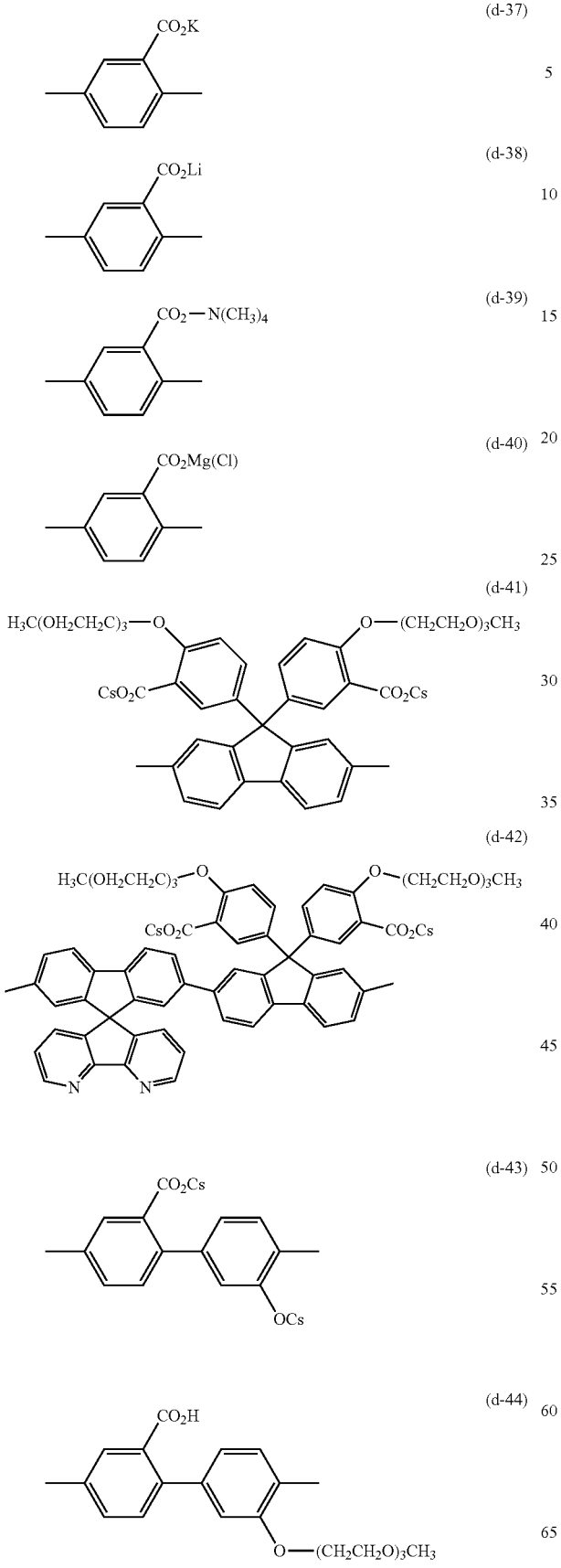

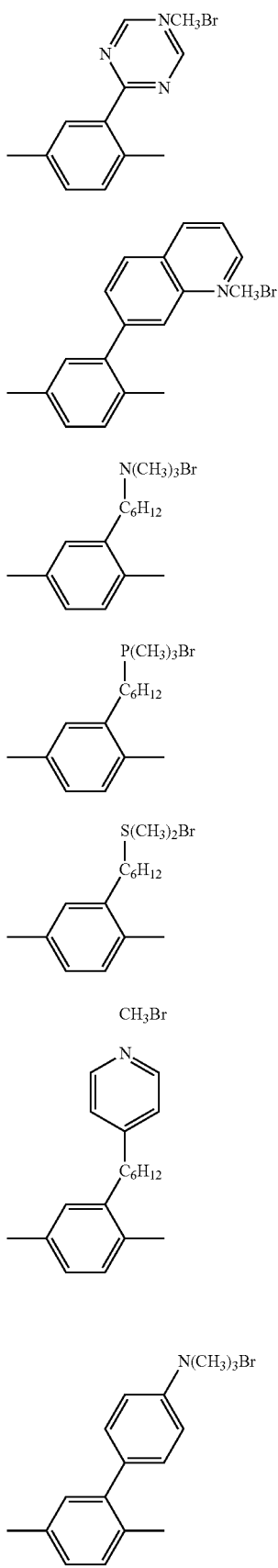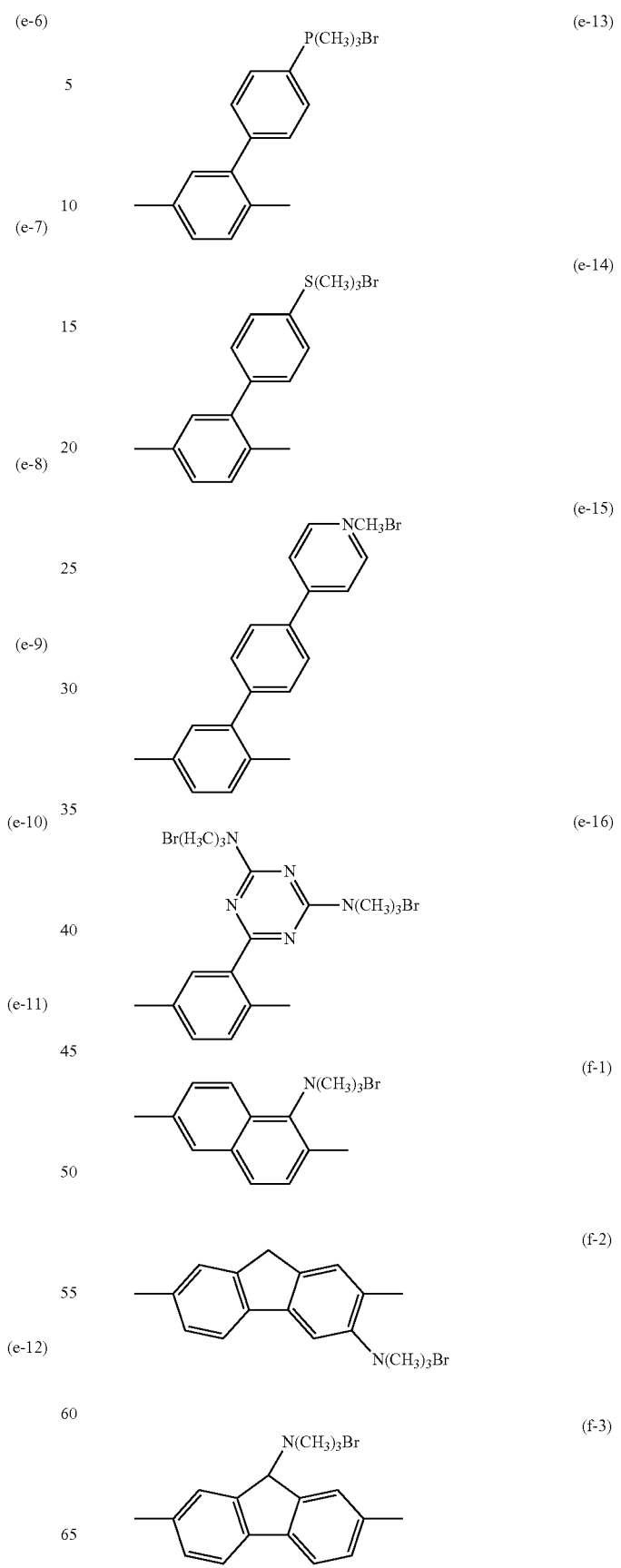

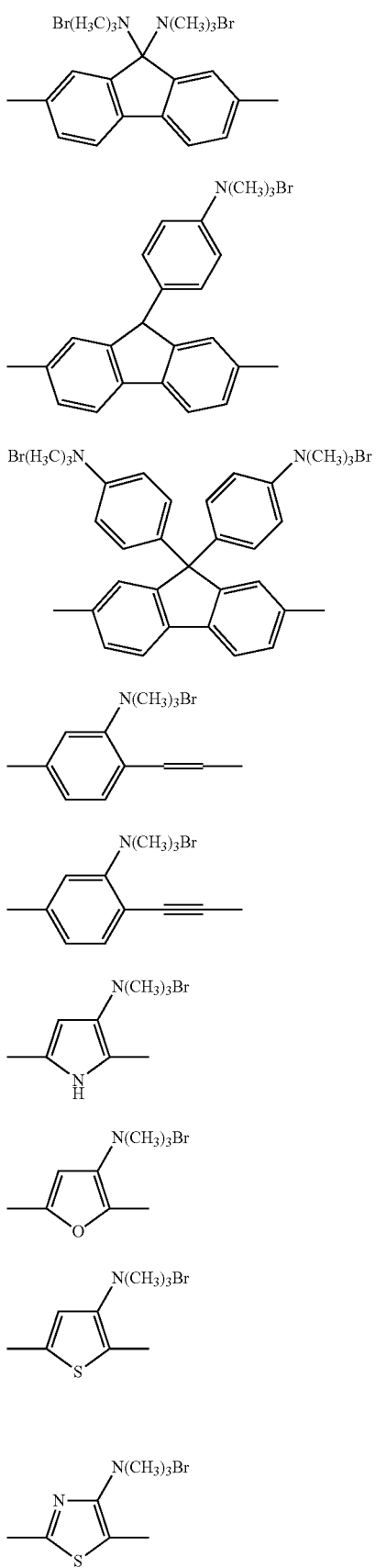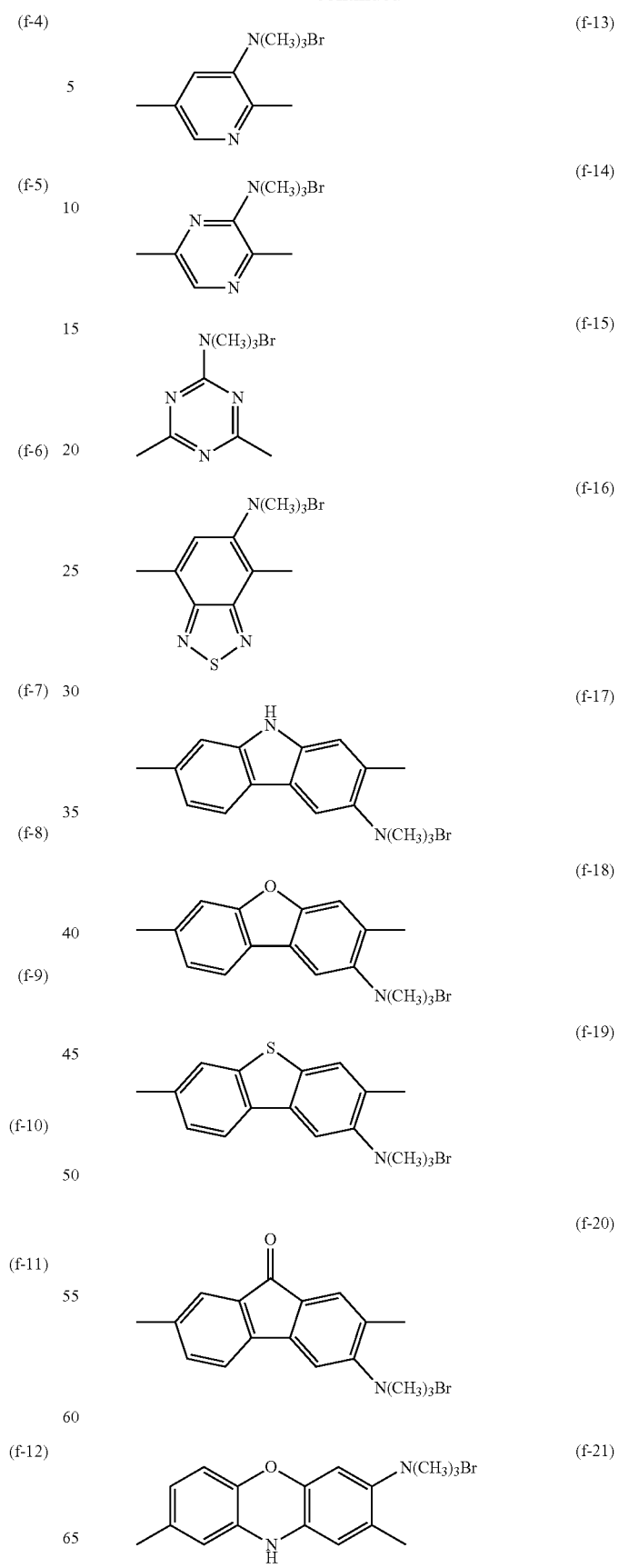

(f-22) 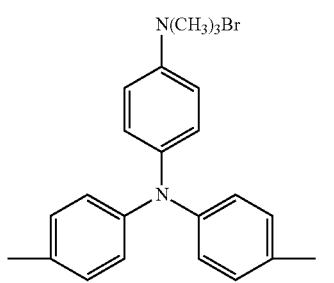
(f-23) 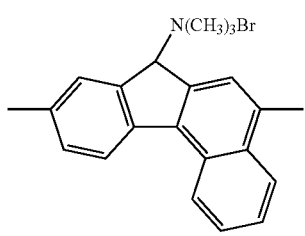
(f-24) 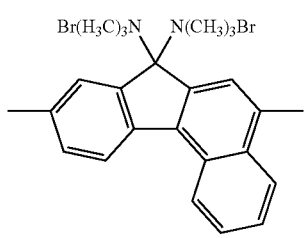
(f-25) 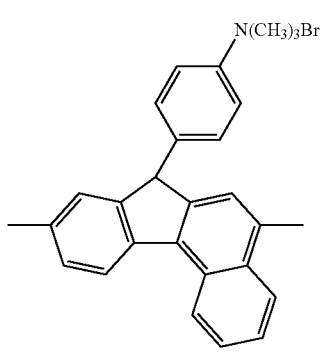
(f-26) 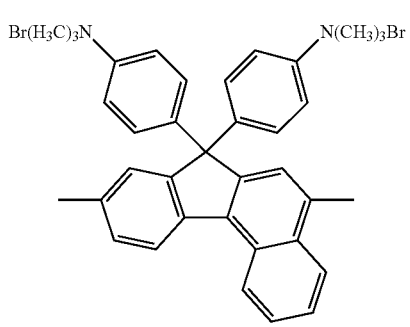
(f-27) 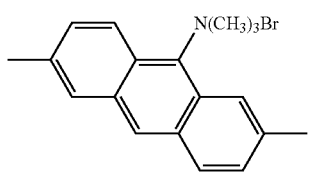
(f-28) 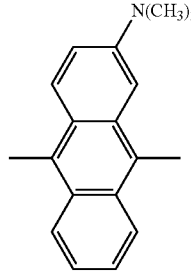
(f-29) 
(f-30) 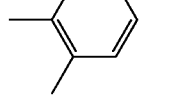
(f-31) 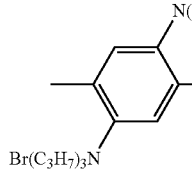
(f-32) 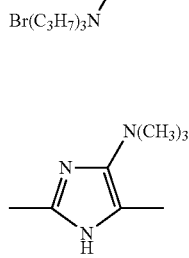
(f-33) 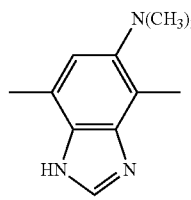
(f-34) 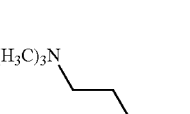
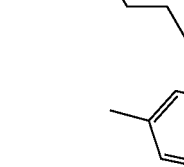

-continued
(f-35)
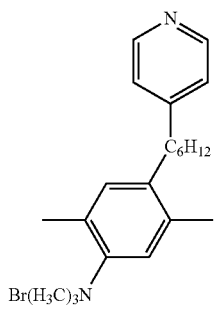
(g-1)
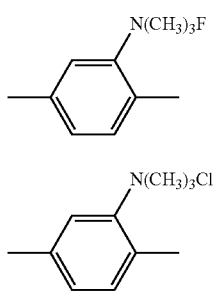
(g-2)
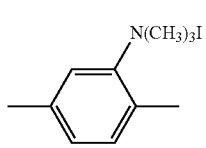
(g-3)
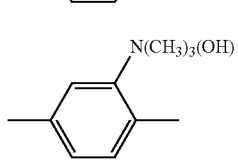
(g-4)
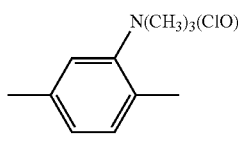
(g-5)
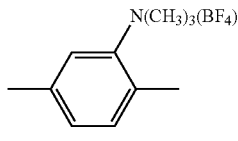
(g-6)
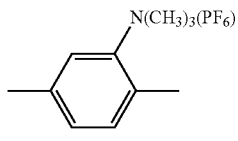
(g-7)
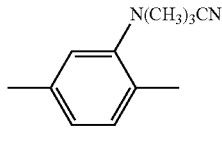
(g-8)
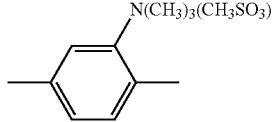
(g-9)
-continued
(g-10)
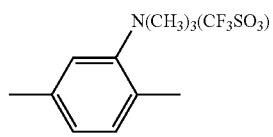
(g-11)
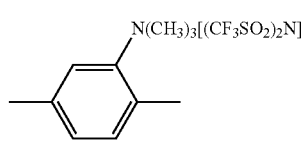
(g-12)
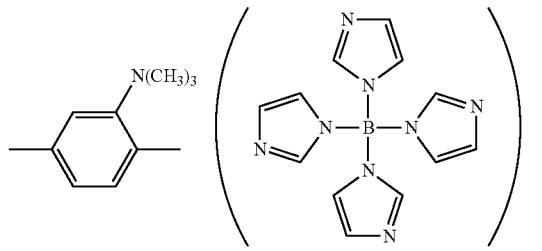
(g-13)
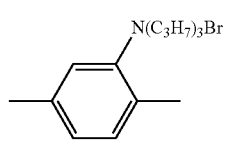
(g-14)
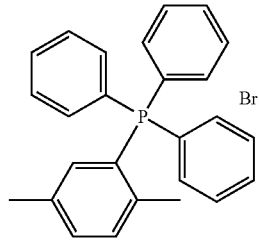
(g-15)
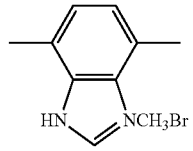
(g-16)
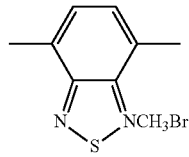
(g-17)

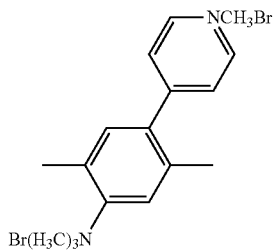
(g-18)

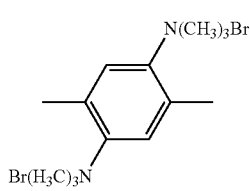
(g-19)

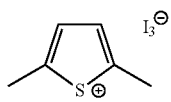
(g-20)

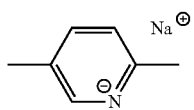
(g-21)

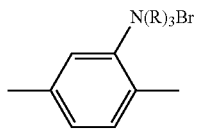
(g-22)

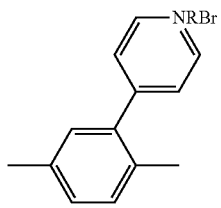
(g-23)

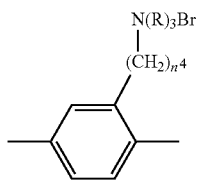
(g-24)

Since an electron injection characteristic is excellent, as the conjugated compound, conjugated compounds having a structural unit represented by formula (c-1) to formula (c-15), formula (c-17), formula (c-20) to formula (c-22), formula (c-24) to formula (c-27), formula (c-29), formula (c-30) to formula (c-37), formula (d-1) to formula (d-6), formula (d-9), formula (d-11) to formula (d-16), formula (d-22), formula (d-31) to formula (d-39), formula (d-41) to formula (d-47), formula (e-1) to formula (e-3), formula (e-5) to formula (e-16), formula (f-1) to formula (f-6), formula (f-9), formula (f-11) to formula (f-16), formula (f-22), formula (f-31) to formula (f-35), formula (g-1) to formula (g-13), and formula (g-16) to formula (g-24) are preferable; conjugated compounds having a structure unit represented by formula (c-1) to formula (c-15), formula (c-17), formula (c-20) to formula (c-22), formula (c-24) to formula (c-27), formula (c-29) to formula (c-32), formula (c-34) to formula (c-37), formula (d-1) to formula (d-6), formula (d-9), formula (d-11), formula (d-13), formula (d-15), formula (d-16), formula (d-22), formula (d-31) to formula (d-39), formula (d-41), formula (d-42), formula (d-47), formula (e-1), formula (e-5) to formula (e-8), formula (e-11), formula (e-12), formula (e-15), formula (e-16), formula (f-1) to formula (f-6), formula (f-9), formula (f-11), formula (f-13), formula (f-15), formula (f-16), formula (f-22), formula (f-31), formula (f-34), formula (f-35), formula (g-1) to formula (g-3), formula (g-6) to formula (g-13), and formula (g-16) to formula (g-24) are more preferable; conjugated compounds having a structure unit represented by formula (c-1) to formula (c-4), formula (c-13) to formula (c-15), formula (c-20) to formula (c-22), formula (c-25) to formula (c-27), formula (c-30) to formula (c-32), formula (d-1), formula (d-2), formula (d-5), formula (d-6), formula (d-9), formula (d-11), formula (d-13), formula (d-22), formula (d-31) to formula (d-38), formula (d-41), formula (d-42), formula (d-47), formula (e-1), formula (e-5), formula (e-7), formula (e-8), formula (e-11), formula (e-12), formula (e-15), formula (e-16), formula (f-1), formula (f-2), formula (f-5), formula (f-6), formula (f-9), formula (f-11), formula (f-13), formula (f-22), formula (f-31), formula (f-34), formula (f-35), formula (g-1) to formula (g-3), formula (g-6), formula (g-7), formula (g-9) to formula (g-13), and formula (g-18) to formula (g-21) are further preferable; conjugated compounds having a structure unit represented by formula (c-1) to formula (c-4), formula (c-15), formula (c-22), formula (c-27), formula (d-6), formula (d-22), formula (d-34) to formula (d-38), formula (d-41), formula (d-42), formula (e-1), formula (e-5), formula (e-8), formula (e-12), formula (e-15), formula (f-6), formula (f-34), formula (g-2), formula (g-6), formula (g-7), formula (g-10) to formula (g-12), and formula (g-18) to formula (g-21) are particularly preferable; conjugated compounds having a structure unit represented by formula (c-1) to formula (c-4), formula (d-6), formula (d-34), formula (d-36) to formula (d-38), formula (d-41), formula (d-42), formula (f-6), formula (f-34), formula (g-2), and formula (g-10) to formula (g-12) are especially preferable; and conjugated compounds having a structure unit represented by formula (c-1) to formula (c-4), (d-38), (d-41), and (d-42) are extremely preferable.

The conjugated compound may be used by doping a dopant. One part by weight or more and 50 parts by weight or less of the dopant with respect to 100 parts by weight of the conjugated compound is preferably used.

Examples of the dopant may include a halogen, a halogen compound, a Lewis acid, a protonic acid, a nitrile compound, an organometallic compound, an alkali metal, and an alkaline earth metal. Examples of the halogen may include chlorine, bromine, and iodine. Examples of the halogen compound may include iodine chloride, iodine bromide, and iodine fluoride. Examples of the Lewis acid may include phosphorus pentafluoride, arsenic pentafluoride, antimony pentafluoride, boron trifluoride, boron trichloride, boron tribromide, and sulfuric anhydride. Examples of the protonic acid may include inorganic acids such as hydrochloric acid, sulfuric acid, nitric acid, phosphoric acid, fluoroboric acid, hydrofluoric acid, and perchloric acid; and organic acids such as a carboxylic acid and a sulfonic acid. Examples of the organic carboxylic acids may include acids having an aliphatic, an aromatic, or a cycloaliphatic carbonyl group such as formic acid, acetic acid, oxalic acid, benzoic acid, phthalic acid, maleic acid, fumaric acid, malonic acid, tartaric acid, citric acid, lactic acid, succinic acid, monochloroacetic acid, dichloroacetic acid, trichloroacetic acid, trifluoroacetic acid, nitroacetic acid, and triphenylacetic acid. Examples of the organic sulfonic acid may include an organic sulfonic acid having an aliphatic, an aromatic, or a cycloaliphatic sulfo group, such as sulfonic acid compounds having one sulfo group in the molecule such as benzenesulfonic acid, p-toluenesulfonic acid, xylenesulfonic acid, naphthalenesulfonic acid, decylbenzenesulfonic acid, dodecylbenzenesulfonic acid, pentadecylbenzenesulfonic acid, methanesulfonic acid, ethanesulfonic acid, 1-propanesulfonic acid, 1-butanesulfonic acid, 1-hexanesulfonic acid, 1-heptanesulfonic acid, 1-octanesulfonic acid, 1-nonanesulfonic acid, 1-decanesulfonic acid, 1-dodecanesulfonic acid, vinylsulfonic acid, styrenesulfonic acid, and allylsulfonic acid; and sulfonic acid compounds having a plurality of sulfo groups in the molecule such as ethanedisulfonic acid, butanedisulfonic acid, pentanedisulfonic acid, decanedisulfonic acid, benzenedisulfonic acid, naphthalenedisulfonic acid, toluenedisulfonic acid, dimethylbenzenedisulfonic acid, diethylbenzenedisulfonic acid, methylnaphthalenedisulfonic acid, and ethylnaphthalenedisulfonic acid.

The organic acid used as the dopant used in the present invention may be a polymeric acid. Examples of the polymeric acid may include polyvinylsulfonic acid, polystyrenesulfonic acid, sulfonated styrene-butadiene copolymer, polyallylsulfonic acid, polymethallylsulfonic acid, poly-2-acrylamide-2-methylpropanesulfonic acid, and polyisoprenesulfonic acid.

Examples of the nitrile compound may include a compound having two more cyano groups in the conjugated bond. Examples of the compound having two or more cyano groups in the conjugated bond may include tetracyanoethylene, tetracyanoethylene oxide, tetracyanobenzene, tetracyanoquinodimethane, and tetracyanoazanaphthalene.

Examples of the organometallic compound may include tris(4-bromophenyl)ammonium hexachloroantimonate, bis(dithiobenzyl) nickel, zinc bis(tetrabutylammonium)bis(1,3-dithiol-2-thione-4,5-dithiolate) complex, and nickel (III) tetrabutylammonium bis(1,3-dithiol-2-thione-4,5-dithiolate) complex.

Examples of the alkali metal may include Li, Na, K, Rb, and Cs. Examples of the alkaline earth metal may include Be, Mg, Ca, Sr, and Ba.

The electron injection layer 44 may further include an ionic compound other than the organic compound having at least one of an ionic group and polar group. Definition, specific examples, and preferable examples of the ionic compound are the same as the definition, the specific examples, and the preferable examples of the ionic compound in the material used in the cathode as described above.

The ionic compound can be used singly or in combination of two or more compounds. A molecular weight of the ionic compound is preferably less than 1,000, more preferably less than 800, further preferably less than 500, and particular preferably less than 300.

The amount of added ionic compound in the electron injection layer 44 of the light-emitting device of the present invention is usually 0.01 parts by weight or more and 1,000 parts by weight or less, preferably 0.1 parts by weight or more and 100 parts by weight or less, and more preferably 1 part by weight or more and 50 parts by weight or less, with respect to 100 parts by weight of the organic compound having at least one of an ionic group and polar group.

Examples of a method for forming the electron injection layer 44 may include a vacuum evaporation method and a coating method. The coating method is preferable as the method for forming the electron injection layer 44. Definition, specific examples, and preferable examples of the coating method are the same as the definition, the specific examples, and the preferable examples of the method for forming the cathode by the coating method as described above.

In the present invention, an aspect "the cathode 34 and the electron injection layer 44 are adjacent (connected)" is realized by a process of forming the electron injection layer 44 after forming the cathode 34, and then stacking them, a process of forming the cathode 34 after forming the electron injection layer 44, and then stacking them, or a process of mixing an electron injection material and a cathode material to obtain an mixture, and thereafter forming a mixed layer by using the mixture. The cathode and the electron injection layer formed by the process described above may form a composite part in such a degree that adjacent parts cannot be distinguished.

In the light-emitting device of the present invention, at least one of the cathode, the anode, and the electron injection layer preferably contains an ionic compound. More preferably, the anode or the electron injection layer contains the ionic compound. Both of the cathode and the electron injection layer can contains the ionic compound. More preferably, the electron injection layer contains the ionic compound because operation stability of the light-emitting device is improved.

—Light-Emitting Layer—

The light-emitting layer 50 of the light-emitting device 10 has a function in which holes can be injected from the anode or the hole injection layer to the light-emitting layer at the time of application of an electric field, a function in which electrons can be injected from the cathode or the electron injection layer, a function in which the injected charge is moved by electric field force, and a function that provides a field of recombination of the electrons and the holes and leads to light-emitting. The light-emitting layer is a single layer constitution made of only one layer or a stacked layer constitution made of two or more layers. Examples of a light-emitting material may include a known low molecular weight compound containing an organic compound, a high molecular weight compound containing an organic compound, and a triplet light-emitting complex containing an organic compound.

Examples of the low molecular weight compound may include dyes such as a naphthalene derivative, anthracene and a derivative thereof, perylene and a derivative thereof, a polymethine dye, a xanthene dye, a coumarin dye, and cyanine dye; a metal complex of 8-hydroxyquinoline, a metal complex of 8-hydroxyquinoline derivative, an aromatic amine, tetraphenylcyclopentadiene and a derivative thereof, and tetraphenylbutadiene and a derivative thereof. Specifically, known compounds such as the compounds described in JP 57-51781 A and JP 59-194393 A can be used as the low molecular weight compound.

Examples of the high molecular weight compound may include a polymer and a copolymer (hereinafter, referred to as a "(co)polymer") whose structural unit is a fluorenediyl group, a (co)polymer whose structural unit is an arylene group, a (co)polymer whose structural unit is an arylenevinylene group, and a (co)polymer whose structural unit is a divalent aromatic amine residual group. Specifically, examples of the high weight compound may include the known compound described in WO 97/09394, WO 98/27136, WO 99/54385, WO 00/22027, WO 01/19834, GB 2340304 A, GB 2348316 B, U.S. Pat. No. 573,636 B, U.S. Pat. No. 5,741,921 B, U.S. Pat. No. 5,777,070 B, EP 707020 B, JP 9-111233 A, JP 10-324870 A, JP 2000-80167 A, JP 2001-123156 A, JP 2004-168999 A, JP 2007-162009 A, and "Development and Constitution Material of Organic EL Element", published by CMC Publishing Co., Ltd., 2006, and these compounds can be used.

Examples of the triplet light-emitting complex may include Ir(ppy)$_3$ and Btp$_2$Ir(acac) represented by the following formula and having iridium (Ir) as a center metal, ADS066GE (trade name, manufactured by American Dye Source, Inc.), PtOEP having platinum (Pt) as a center metal, and Eu(TTA)$_3$phen having europium (Eu) as a center metal.

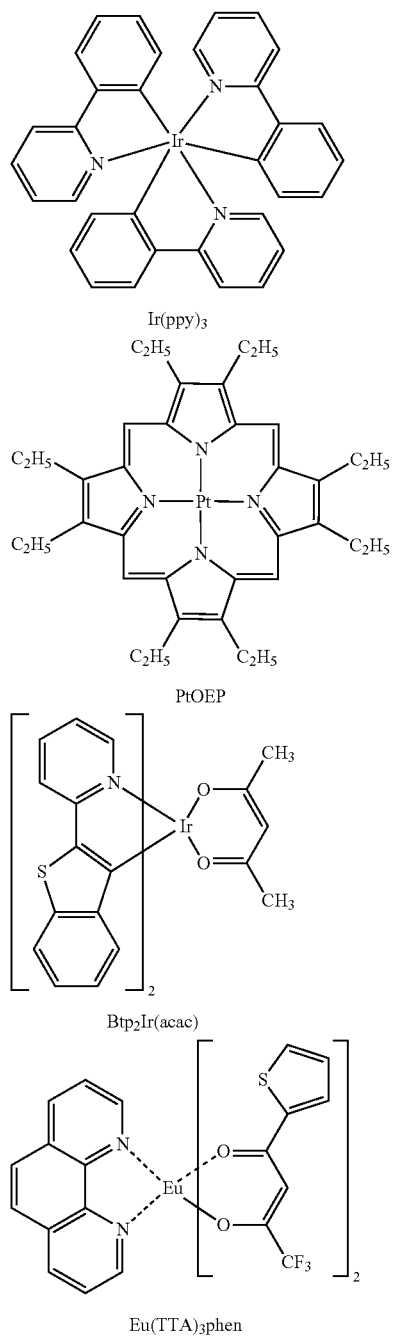

An optimum value of a thickness of the light-emitting layer varies depending on a material used. The thickness of the light-emitting layer may be selected so that drive voltage and light-emitting efficiency are reasonable values. The thickness of the light-emitting layer is usually 1 nm or more and 1 μm or less, preferably 2 nm or more and 500 nm or less, more preferably 5 nm or more and 200 nm or less, and further preferably 50 nm or more and 150 nm or less.

Examples of a method for forming the light-emitting layer 50 may include a vacuum evaporation method and a coating method. The coating method is preferable as the method for forming the light-emitting layer 50. Definition, specific examples, and preferable examples of the coating method are the same as the definition, the specific examples, and the preferable examples of the method for forming the cathode by the coating method as described above.

—Hole Injection Layer—

In the light-emitting device 10 of the present invention, it is possible to form the hole injection layer 42a using a hole injection material. The light-emitting device of the present invention may have the hole injection layer between the light-emitting layer and the anode. The hole injection layer is a single layer constitution made of only one layer or a stacked layer constitution made of two or more layers.

Examples of the hole injection material may include a carbazole derivative, a triazole derivative, an oxazole derivative, an oxadiazole derivative, an imidazole derivative, fluorene derivative, a polyarylalkane derivative, a pyrazoline derivative, a pyrazolone derivative, phenylenediamine derivative, a arylamine derivative, a star-burst-type amine, a phthalocyanine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidyne compound, a porphyrin compound, a polysilane compound, a poly(N-vinylcarbazole) derivative, an organic silane derivative, and a polymer containing these substances; conductive metal oxides such as vanadium oxide, tantalum oxide, tungsten oxide, molybdenum oxide, ruthenium oxide, and aluminum oxide; conductive polymeric materials and oligomers such as polyaniline, an aniline copolymer, a thiophene oligomer, and polythiophene; organic conductive materials and polymers containing thereof such as poly(3,4-ethylenedioxythiophene)/polystyrene sulfonic acid and polypyrrole; amorphous carbon; organic compounds having acceptor characteristic such as a tetracyanoquinodimethane derivative including 2,3,5,6-tetrafluoro-7,7,8,8-tetracyanoquinodimethane, a 1,4-naphthoquinone derivative, a diphenoquinone derivative, and a polynitro compound; and silane coupling agents such as octadecyltrimethoxysilane.

The hole injection material may be used as a single component or a composition made of a plurality of component. The hole injection layer 42a is a single layer structure made of only a single hole injection material or a multi-layered structure made of a plurality of layers constituted by an hole injection material made by the same composition or different compositions.

An optimum value of a thickness of the hole injection layer 42a varies depending on a material used. The thickness of the hole injection layer 42a may be selected so that drive voltage and light-emitting efficiency have reasonable values. The thickness of the hole injection layer 42a is usually 1 nm or more and 1 μm or less, preferably 2 nm or more and 500 nm or less, more preferably 5 nm or more and 200 nm or less, and further preferably 5 nm or more and 100 nm or less.

Examples of a method for forming the hole injection layer 42a may include a vacuum evaporation method and a coating method. The coating method is preferable as the method for forming the hole injection layer. Definition, specific examples, and preferable examples of the coating method are the same as the definition, the specific examples, and the preferable examples of the method for forming the cathode by the coating method as described above.

—Other Layers—

The light-emitting device of the present invention may further comprise a substrate, a hole transport layer, an electron transport layer, an interlayer, an electron injection layer, a hole blocking layer, an electron blocking layer, and a charge generation layer.

The hole transport layer refers to a layer having a function of transporting holes. The electron transport layer refers to a layer having a function of transporting electrons. The interlayer is a layer existing between the light-emitting layer and the anode and adjacent to the light-emitting layer, and having a role of separating the light-emitting layer and the anode, or the light-emitting layer and the hole injection layer or the hole transport layer. The hole blocking layer is a layer having a function of blocking holes mainly injected from the anode, and further having either a function of receiving electrons from the cathode or a function of transporting electrons, if necessary. The electron blocking layer is a layer having a function of blocking electrons mainly injected from the cathode, and further having either a function of receiving holes from the anode or a function of transporting holes, if necessary. The charge generation layer refers to a layer in which holes are injected to a layer closer to the adjacent cathode, and electrons are injected to a layer closer to the adjacent anode.

The electron transport layer and the hole transport layer are generically referred to as a charge transport layer. The electron injection layer and the hole injection layer generically referred to as a charge injection layer. The hole transport layer, the electron transport layer, the interlayer, the electron injection layer, the hole blocking layer, the electron blocking layer, and the charge generation layer may be a structure made of only one layer or a structure made of two more layers. Examples of a method for forming each of these layers may include a vacuum evaporation method and a coating method and the coating method is preferable. Definition, specific examples, and preferable examples of the coating method are the same as the definition, the specific examples, and the preferable examples of the method for forming the cathode by the coating method as described above.

—Method for Manufacturing Light-Emitting Device—

A method for manufacturing the light-emitting device according to the embodiments of the present invention may comprise a step for applying a coating solution that contains a conductive material having an aspect ratio of 1.5 or more, and thereby forming the cathode or the anode.

The light-emitting device can be manufactured by, for example, sequentially stacking each layer. The methods for forming each of the layers are as described above.

One embodiment of the method for manufacturing the light-emitting device of the present invention comprises a step for forming the cathode by a coating method. Preferably, the embodiment of the method for manufacturing the light-emitting device of the present invention further comprises steps for forming each of the remaining layers other than the anode by the coating method in addition to the step for forming the cathode by the coating method. In other words, the embodiment of the method for manufacturing the light-emitting device of the present invention comprises the step for forming the cathode by the coating method and the steps for forming each of the remaining layers other than the anode by the coating method. More preferably, the embodiment of the method for manufacturing the light-emitting device of the present invention further comprises a step for forming the anode by the coating method. In other words, the embodiment of the method for manufacturing the light-emitting device of the present invention comprises a step for forming the anode and the cathode by the coating method, or a step for forming all of the remaining layers in addition to the anode and the cathode by the coating method (that is, a step for forming each of the all layers by the coating method).

In one embodiment of the light-emitting device of the present invention, the cathode in the light-emitting device is formed by a coating method. In the embodiment of the light-emitting device, preferably, each of all of the remaining layers other than the anode in addition to the cathode is formed by the coating method. In other words, the cathode and each of all of the remaining layers other than the anode are formed by the coating method (that is, each of all the layers except the anode is formed by the coating method). More preferably, in the embodiment of the light-emitting device, the anode is further formed by the coating method. In other words, each of the anode and the cathode is formed by the coating method, or each of all of the other remaining layers in addition to the anode and the cathode is formed by the coating method (that is, each of all the layers is formed by the coating method).

—Structure of Light-Emitting Device—

The structure of the light-emitting device has a forward stacked structure and an inverted stacked structure. The forward stacked structure is a structure manufactured by a method for manufacturing a structure in which electrodes and organic layers are sequentially stacked from the anode to the cathode, and for example, a structure in which the anode, the light-emitting layer, the electron injection layer, and the cathode are stacked on the substrate in this order so that the anode is located closer to the substrate.

The inverted stacked structure is a structure manufactured by a method for manufacturing a structure in which electrodes and organic layers are sequentially stacked from the cathode to the anode, and for example, a structure in which the cathode, the electron injection layer, the light-emitting layer, and the anode are stacked on the substrate in this order so that the cathode is located closer to the substrate.

Examples of the structure of the light-emitting device of the present invention may include structures represented by following formula a) to formula d). Examples of the inverted stacked structure include the structures represented by formula a) and formula b), and examples of the forward stacked structure include the structures represented by formula c) and formula d). The structure represented by formula c) and the structure represented by formula d) are preferable as the examples of the structure of the light-emitting device.

a) Cathode/Electron injection layer/Light-emitting layer/Anode b) Cathode/Electron injection layer/(Electron transport layer/) (Hole blocking layer/) Light-emitting layer/(Interlayer/) (Electron blocking layer/) (Hole transport layer/) (Hole injection layer/) (Charge generation layer/) (Electron injection layer/) (Electron transport layer/) (Light-emitting layer/) (Interlayer/) (Electron blocking layer/) (Hole transport layer/) (Hole injection layer/) Anode c) Anode/Light-emitting layer/Electron injection layer/Cathode d) Anode/(Hole injection layer/) (Hole transport layer/) (Electron blocking layer/) (Interlayer/) Light-emitting layer/ (Hole blocking layer/) (Electron transport layer/) (Electron injection layer/) (Charge generation layer/) (Hole injection layer/) (Hole transport layer/) (Electron blocking layer/) (Interlayer/) (Light-emitting layer/) (Hole blocking layer/) (Electron transport layer/) Electron injection layer/Cathode Here, the symbol "/" represents that each layers interposing the symbol "/" are adjacently connected each other. The layers in the parentheses each independently may not be provided. Here, the cathode and the electron injection layer must be adjacently connected each other.

Each layer may be a layer having a plurality of functions, that is, a layer having both its own function and functions that other layers have.

At least one of the anode and the cathode usually has optical transparency, and preferably the cathode has the optical transparency.

The light-emitting device may have either a top emission-type structure in which light is emitted from an exposed surface of the opposite side to the substrate in a thickness direction of the substrate, or a bottom emission-type structure in which light is emitted from an exposed surface of the substrate side.

The light-emitting device is preferably a top emission-type structure in which the light-emitting device further provides a substrate and the anode is connected to the substrate, and light is emitted from a side closer to the cathode opposite to the substrate in a thickness direction of the substrate.

When the light-emitting device is an inverted stacked structure, a bottom emission-type structure in which a transparent substrate having optical transparency is used as the substrate and the cathode is connected to the transparent substrate, and light is emitted from a side closer to the cathode (a substrate side) may be used.

In another embodiment of the light-emitting device of the present invention, a device of both-sided light emitting-type device in which both of the anode and the cathode have optical transparency and light is emitted from both the side closer to the anode and the side closer to the cathode by using a material having optical transparency for the anode and the cathode can be manufactured.

In the both-sided light emitting-type light-emitting device, layers other than the cathode and the anode (such as the electron injection layer and the light-emitting layer) in the device may be opaque layers or transparent layers. When the layers other than the cathode and the anode are transparent, the both-sided light emitting-type device has optical transparency when light is not emitted. However, the device is opaque at the time of emitting light because transparency of light is prevented by the light-emitting of the device.

—Application of Light-Emitting Device—

A display device and a lighting device can be manufactured by using the light-emitting device of the present invention. The display device provides the light-emitting device as one pixel unit. An array of the pixel units can be an array usually employed for display devices such as a television set, and can be a form of arraying a large number of pixels on one substrate. In the display device, the pixels arrayed on the substrate may be formed in a pixel region defined by a bank.

<Photovoltaic Cell>

Figure 2A:
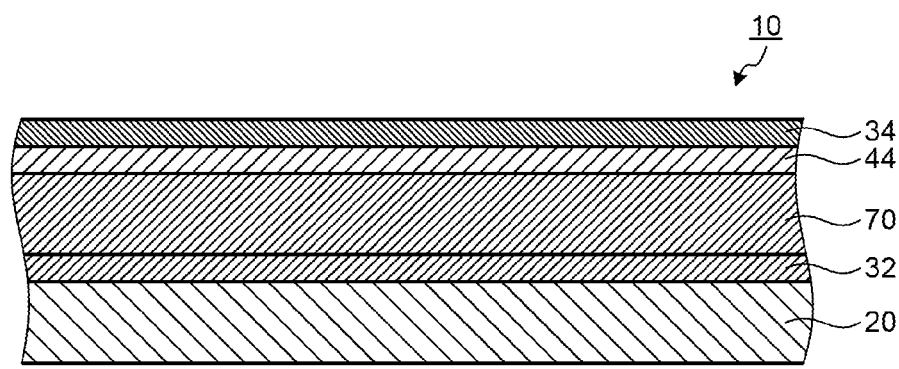
FIG. 2A is a cross-sectional view schematically illustrating constitution example (1) of a photovoltaic cell.
Figure 2B:
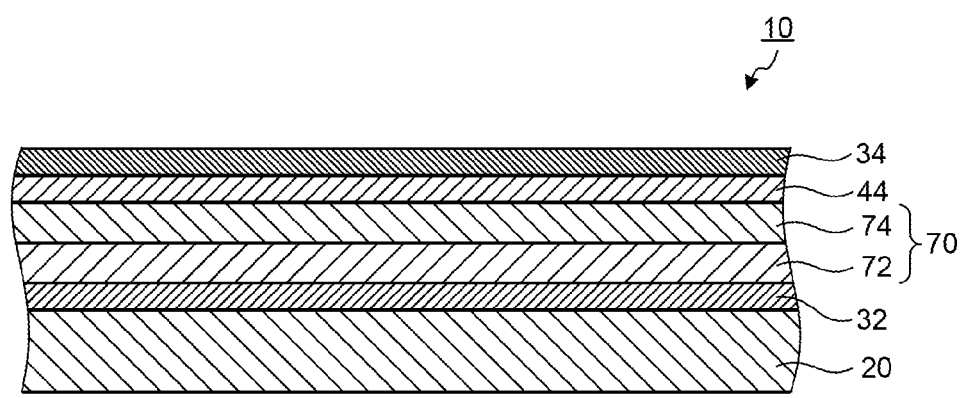
FIG. 2B is a cross-sectional view schematically illustrating constitution example (2) of a photovoltaic cell.

With reference to FIG. 2A and FIG. 2B, a constitutional example of a photovoltaic cell will be described.

FIG. 2A is a cross-sectional view schematically illustrating constitutional example (1) of a photovoltaic cell. FIG. 2B is a cross-sectional view schematically illustrating constitutional example (2) of a photovoltaic cell.

The photovoltaic cell of an embodiment of the present invention comprises a cathode, an anode, a charge separation layer interposed between the cathode and the anode, and an electron injection layer provided between the cathode and the charge separating layer and connected to the cathode, in which at least one of the cathode and the anode contains a conductive material having an aspect ratio of 1.5 or more, and the electron injection layer contains an organic compound having at least one of an ionic group and a polar group.

The cathode, the anode, and the electron injection layer of the photovoltaic cell may further contain an ionic compound. Definition, specific examples, and preferable examples of the ionic compound are the same as the definition, the specific examples, and the preferable examples of the ionic compound in the cathode of the light-emitting device as described above.

The ionic compound can be used singly or in combination of two or more compounds. A molecular weight of the ionic compound is preferably less than 1,000, more preferably less than 800, further preferably less than 500, and particular preferably less than 300.

When the cathode 34 of the photovoltaic cell contains ionic compound, the amount of added ionic compound in the cathode is usually 0.01 parts by weight or more and 1,000 parts by weight or less, preferably 0.1 parts by weight or more and 100 parts by weight or less, and more preferably 1 part by weight or more and 50 parts by weight or less, with respect to 100 parts by weight of the material of the cathode.

When the anode 32 of the photovoltaic cell of the present invention contains the ionic compound, the amount of added ionic compound in the anode is usually 0.01 parts by weight or more and 1,000 parts by weight or less, preferably 0.1 parts by weight or more and 100 parts by weight or less, and more preferably 1 part by weight or more and 50 parts by weight or less, with respect to 100 parts by weight of the material of the anode.

When the electron injection layer 44 of the photovoltaic cell of the present invention contains ionic compound, the amount of added ionic compound in the manufacturing process of the electron injection layer is usually 0.01 parts by weight or more and 1,000 parts by weight or less, preferably 0.1 parts by weight or more and 100 parts by weight or less, and more preferably 1 part by weight or more and 50 parts by weight or less, with respect to 100 parts by weight of the organic compound having at least one of an ionic group and a polar group.

Of the cathode and the anode, at least an electrode at the side when light is incident, that is, at least one electrode is an transparent or semi-transparent electrode that transmits the incident light.

Constitutional Example (1)

As illustrated in FIG. 2A, the photovoltaic cell 10 of constitutional example (1) comprises a pair of electrodes comprising the anode 32 and cathode 34, and a charge separation layer 70 interposed between the pair of electrodes. Namely, the photovoltaic cell 10 of constitutional example (1) is a bulk heterojunction-type photovoltaic cell.

A photovoltaic cell is usually formed on a substrate. Namely, the photovoltaic cell 10 is provided on the main surface of the substrate 20.

When the substrate 20 is opaque, the cathode 34 that faces to the anode 32 and provided at the opposite side to the substrate side (that is, a further electrode from the substrate 20) is preferably transparent or semi-transparent.

The charge separation layer 70 is interposed between the cathode 32 and the anode 34, and is in contact with them. The charge separation layer 70 is an organic layer containing an electron acceptor compound and an electron donor compound, and a layer having an essential function for a photovoltaic function.

The anode 32 is provided on the main surface of the substrate 20. The charge separation layer 70 is provided so as to cover the anode 32. The electron injection layer 44 is connected to the charge separation layer 70. The cathode 34 is connected to the electron injection layer 44.

The photovoltaic cell 10 of constitutional example (1) is preferable because the charge separation layer 70 has a constitution of the electron acceptor compound and the electron donor compound contained in the single layer, and more heterojunction interfaces are comprised therein, and as a result, photovoltaic efficiency is improved.

Constitutional Example (2)

As illustrated in FIG. 2B, the photovoltaic cell of constitutional example (2) comprises the pair of electrodes comprising the anode 32 and cathode 34, and the charge separation layer 70 interposed between the pair of electrodes, the charge separation layer 70 comprising an electron acceptor layer 74 containing the electron acceptor compound and an electron donor layer 72 containing the electron donor compound and connected to the electron acceptor layer 74. Namely, the photovoltaic cell 10 of constitutional example (2) is a heterojunction-type photovoltaic cell.

The photovoltaic cell 10 is provided on the main surface of the substrate 20. The anode 32 is provided on the main surface of the substrate 20.

The charge separation layer 70 is interposed between the anode 32 and the electron injection layer 44, and is in contact with them. The charge separation layer 70 of constitutional example 2 is a layered structure in which the electron acceptor layer 74 containing the electron acceptor compound and the electron donor layer 72 containing the electron donor compound are connected.

The electron donor layer 72 is provided so as to be connected to the anode 32. The electron acceptor layer 74 is provided so as to be connected to the electron donor layer 72. The electron injection layer 44 is connected to the electron acceptor layer 74. The cathode 34 is connected to the electron injection layer 44.

—Charge Separation Layer—

The charge separation layer 70 may contain each of the electron donor compound and the electron acceptor compound singly or in combination of two more compounds. The electron donor compound or the electron acceptor compound is relatively determined by energy level of these compounds.

Examples of the electron donor compound may include a pyrazoline derivative, an arylamine derivative, a stilbene derivative, a triphenyldiamine derivative, and a conjugated macromolecular compound. Examples of the conjugated macromolecular compound may include oligothiophene and a derivative thereof, polyfluorene and a derivative thereof, polyvinylcarbazole and a derivative thereof, polysilane and a derivative thereof, a polysiloxane derivative having aromatic amines in the main chain or the side chain thereof, polyaniline and a derivative thereof, polypyrrole and a derivative thereof, a polyphenylenevinylene and derivative thereof, and polythienylenevinylene and a derivative thereof.

Examples of the electron acceptor compound may include an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, polyquinoline and a derivative thereof, polyquinoxaline and a derivative thereof, polyfluorene and a derivative thereof, fullerenes such as $C_{60}$ fullerene and a derivative thereof, phenanthrene derivatives such as bathocuproine, metal oxides such as titanium oxide, and a carbon nanotube. As the electron acceptor compounds, titanium oxide, the carbon nanotube, the fullerenes, and the fullerene derivatives are preferable, and the fullerenes and the fullerene derivatives are particularly preferable.

A thickness of the charge separation layer is preferably 1 nm or more and 100 µm or less, more preferably 2 nm or more and 1,000 nm or less, further preferably 5 nm or more and 500 nm or less, and particularly preferably 20 nm or more and 200 nm or less.

The charge separation layer is formed by any methods, and examples of a method for forming the charge separation layer may include a vacuum evaporation method and a coating method. The coating method is preferable as the method for forming the charge separation layer. The coating method is the same as the method in relation to each layer constituting the light-emitting device as described above.

—Layers Other than Charge Separation Layer—

In the photovoltaic cell 10, for example, an additional layer such as a layer having a function of improving an injection characteristic (a transport characteristic) of charges (electrons and holes) may be provided between one of the electrodes of the anode 32 and the cathode 34 and the charge separation layer.

Examples of the additional layer may include the electron injection layer and the hole injection layer (the charge injection layer), the hole transport layer and the electron transport layer (the charge transport layer), and the interlayer.

Similar constitution to the constitution for the light-emitting device as previously described may be used for constitution of layers other than the charge separation layer, that is, the cathode, the anode, the substrate, the electron injection layer, the hole injection layer, the hole transport layer, the electron transport layer, the interlayer, and the like. Therefore, the detailed description of constitution of these layers is omitted.

—Method for Manufacturing Photovoltaic Cell—

In a method for manufacturing a photovoltaic cell according to an embodiment of the present invention comprising a cathode, an anode, a charge separation layer interposed between the cathode and the anode, and an electron injection layer provided between the cathode and the charge separation layer and connected to the cathode, the method comprises the steps of: applying a coating solution that contains an organic compound having at least one of an ionic group and a polar group, thereby forming the electron injection layer, and applying a coating solution that contains the conductive material having the aspect ratio of 1.5 or more, thereby forming the cathode connected to the electron injection layer.

The photovoltaic cell can be manufactured by, for example, sequentially stacking each layer described above on the substrate. Methods for forming each of the layers described above other than the charge separation layer can be performed the same methods for forming each of the corresponding layers of the light-emitting device. Therefore, the detailed description of these methods is omitted.

One embodiment of the method for manufacturing the photovoltaic cell of the present invention comprises a step for forming the cathode by the coating method. Preferably, the embodiment of the method for manufacturing the photovoltaic cell comprises steps for forming each of the remaining layers other than the anode by the coating method in addition to the step for forming the cathode by the coating method. In other words, the embodiment of the method for manufacturing the photovoltaic cell comprises the step for forming the cathode by a coating method and the steps for forming each of the remaining layers other than the anode by the coating method.

More preferably, the embodiment of the method for manufacturing the photovoltaic cell further comprises a step for forming the anode by the coating method. In other words, the embodiment of the method for manufacturing the photovoltaic cell comprises steps for forming each of the anode and the cathode by the coating method, or a step for forming all of the remaining layers in addition to the anode and the cathode by the coating method (that is, steps for forming each of the all layers by the coating method).

In one embodiment of the photovoltaic cell of the present invention, the cathode in the photovoltaic cell is formed by the coating method. Preferably, in the embodiment of the photovoltaic cell, each of all the remaining layers other than the anode in addition to the cathode is formed by the coating method. In other words, the cathode and each of all the remaining layers other than the anode are formed by the coating method (that is, each of all the remaining layers other than the anode is formed by the coating method). More preferably, in the embodiment of the photovoltaic cell, the anode is further formed by the coating method. In other words, each of the anode and the cathode is formed by the coating method, or each of all the other remaining layers in addition to the anode and the cathode is formed by the coating method (that is, each of all the layers is formed by the coating method).

EXAMPLES

Hereinafter, Examples and Comparative examples will be specifically described. However, the present invention is not limited to following Examples.
<Analysis Methods>
A weight average molecular weight (Mw) and a number average molecular weight (Mn) of the conjugated compound were determined by using gel permeation chromatography (GPC) (manufactured by TOSOH CORPORATION, Trade name: HLC-8220GPC) as the weight average molecular weight and the number average molecular weight in terms of polystyrene. A sample for measurement was dissolved into tetrahydrofuran so that a concentration of the solution is about 0.5% by weight, and the 50 μL of dissolved sample was injected into the GPC. As a mobile phase of the GPC, tetrahydrofuran was used and flowed at a flow rate of 0.5 mL/min. A detection wavelength was set to 254 nm.
Structural analysis of the conjugated compounds was performed by $^1$H-NMR analysis using a 300 MHz NMR spectrometer (manufactured by Varian, Inc.). $^1$H-NMR analysis was performed by using a sample dissolved into a deuteration solvent that can dissolve the sample so as to be a concentration of 20 mg/mL.

Synthesis Example 1

Synthesis of Silver Nano-Structure A

A flask having a volume of 50 mL and containing 5 mL of ethylene glycol was immerged into an oil bath having a temperature of 150° C. The ethylene glycol was pre-heated for 60 minutes with bubbling air. After the pre-heating, gas for the bubbling was changed from air to nitrogen gas to replace the atmosphere in the flask by nitrogen gas, and then the bubbling was stopped. Subsequently, 1.5 mL of 0.1 M silver nitrate-ethylene glycol solution, 1.5 mL of 0.15 mol/L polyvinylpyrrolidone (hereinafter, also referred to as "PVP", manufactured by Sigma-Aldrich Co. LLC., a weight average molecular weight described in the brochure: $5.5 \times 10^4$) ethylene glycol solution, and 40 μL of 4 mmol/L copper chloride dihydrate ethylene glycol solution were further added and the mixture was stirred for 120 minutes, thus obtaining a dispersion liquid of a silver nano-structure. After cooling the obtained dispersion liquid to 40° C., the dispersion liquid was centrifuged to obtain a precipitate. The obtained precipitate was dried, thus obtaining the silver nano-structure (hereinafter, referred to as the "silver nano-structure A").

A photograph of the obtained silver nano-structure A taken by a scanning electron microscope (manufactured by JEOL Ltd., trade mane: JSM-5500) (hereinafter, referred to as "SEM") was visually observed. The silver nano-structure A is wire-shaped, an average value of the shortest diameter of about 30 nm, and an average value of the longest diameter of about 15 μm. An average value of an aspect ratio of at least 10 particles of silver nano-structure A determined by the SEM was about 500.

Synthesis Example 2

Synthesis of Conjugated Compound P-1

52.5 g (0.16 mol) of 2,7-dibromo-9-fluorenone, 154.8 g (0.93 mol) of ethyl salicylate, and 1.4 g (0.016 mol) of mercaptoacetic acid were placed into a flask having a volume of 3,000 mL, and the atmosphere in the flask was replaced by nitrogen gas. Methanesulfonic acid (630 mL) was further added into the flask and the mixture was stirred overnight at 75° C. The mixture was allowed to cool. When the mixture was added to ice water and the resultant mixture was stirred for 1 hour, a solid was generated. The generated solid was separated by filtration and the solid was washed with heated acetonitrile. The washed solid was dissolved into acetone. A solid was obtained by recrystallization from the obtained acetone solution and separated by filtration. The obtained solid (62.7 g), 2-[2-(2-methoxyethoxy)ethoxy]ethoxy-p-toluenesulfonate (86.3 g, 0.27 mmol), potassium carbonate (62.6 g, 0.45 mmol), and 18-crown-6 (7.2 g, 0.027 mol) were dissolved into N,N-dimethylformamide (DMF) (670 mL). The obtained solution was transferred to a flask and stirred overnight at 105° C. The obtained solution was allowed to cool to the room temperature. The mixture is added to ice water, and the resultant mixture was stirred for 1 hour. Chloroform was added the solution to perform liquid separation and extraction. 2,7-dibromo-9,9-bis[3-ethoxycarbonyl-4-[2-[2-(2-methoxyethoxy)ethoxy]ethoxy]phenyl-fluorene (compound B) (51.2 g) was obtained by concentrating the obtained solution. The yield was 31%.

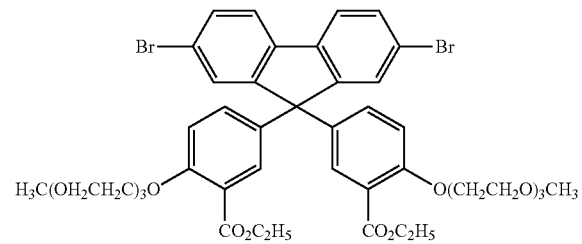

Compound B 4,5-diaza-2',7'-dibromo, 9,9'-spirobifluorene (compound C) represented by the following formula was synthesized by a method described in K.-T. Wong, R.-T. Chen, F.-C. Fang, C.-c. Wu, and Y.-T. Lin, Organic Letters, Vol. 7, p. 1979.

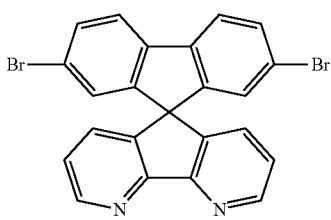

Compound C 810 mg (3.0 mmol) of bis(1,5-cyclooctadiene) nickel, 469 mg (3.0 mmol) of 2,2'-bipyridyl, 325 mg (3.0 mmol) of 1,5-cyclooctadiene, and a mixed solvent of 10 mL of toluene and 10 mL of N,N-dimethylformamide were placed in a flack having a volume of 100 mL whose inner gas was replaced by argon gas, and the mixture was dissolved. A solution in which 850 mg (0.90 mmol) of the compound B and 48 mg (0.10 mmol) of the compound C were dissolved into a mixed solvent of 5 mL of toluene and 15 mL of dimethylformamide was further added into the flask. After stirring the reaction solution for 6 hours at 80° C., 16 mg (0.10 mmol) of bromobenzene was added, and the mixture was further stirred for 1 hour at 80° C. After cooling the obtained reaction solution to the room temperature, the obtained reaction solution was added dropwise to 300 mL of methanol. When the mixture was stirred for 1 hour, a solid was deposited. The solid was filtrated, and the residue was washed with hydrochloric acid, distilled water, aqueous ammonia, and distilled water in this order, and dried, thus obtaining 596 mg of the conjugated compound P-1. The yield was 81%.

From the result of NMR analysis, the conjugated compound P-1 contains two structural units represented by the following formulae in a molar ratio of 9:1 (a theoretical value from the amount of fed raw materials) in the order of description.

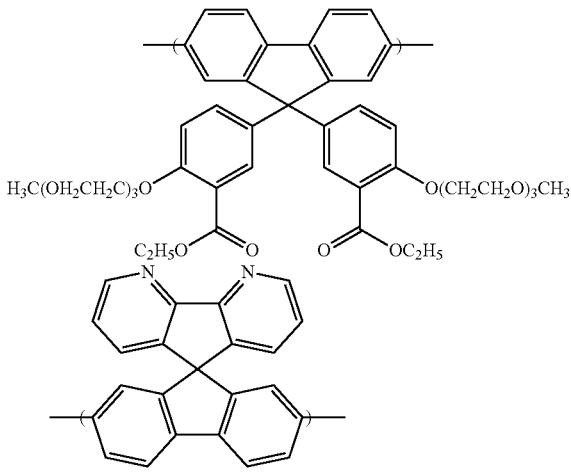

A number average molecular weight of the conjugated compound P-1 in terms of polystyrene was $2.0 \times 10^4$.

Synthesis Example 3

Synthesis of Conjugated Compound P-2

The conjugated compound P-1 (100 mg) was fed into a flask whose inner gas was replaced by argon gas, and was dissolved into 20 mL of tetrahydrofuran and 2 mL of ethanol. 3 mL of aqueous solution containing 334 mg of cesium hydroxide was added to the obtained solution and the resultant solution was stirred for 2 hours at 55° C. 5 mL of methanol was added to the obtained reaction solution, and the resultant solution was stirred with heating for 3 hours at 60° C. Subsequently, 3 mL of aqueous solution containing 334 mg of cesium hydroxide was added to the reaction solution, and the resultant solution was refluxed by heating for 2 hours at 65° C. When the solvent of the obtained reaction solution was removed by distillation, a solid was deposited. The solid was washed with water. The solid after washing was filtrated and the residue was dried, thus obtaining a 110 mg of conjugated compound containing two structural units represented by the following formulae in a molar ratio of 9:1 (a theoretical value from the amount of fed raw materials) in the order of description (hereinafter, referred to as "conjugated compound P-2") was obtained.

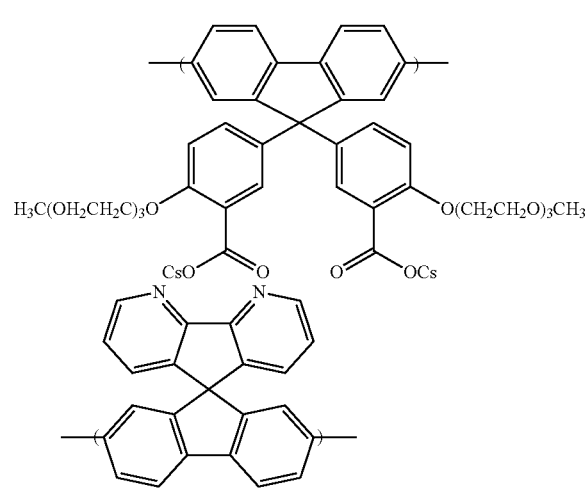

The yield was 88%. It was confirmed by NMR spectrum that a signal based on an ethyl group of an ethyl ester part in the conjugated compound P-1 was completely disappeared.

Synthesis Example 4

Synthesis of Conjugated Compound P-3

The compound B (15 g), bis(pinacolato)diboron (8.9 g), [1,1'-bis(diphenylphosphino)ferrocene]dichloropalladium (II) dichloromethane complex (0.8 g), 1,1'-bis(diphenylphosphino)ferrocene (0.5 g), potassium acetate (9.4 g), and dioxane (400 mL) were added into a flack having a volume of 1,000 mL whose inner gas was replaced by argon gas, and mixed. The mixture was heated at 110° C., and refluxed by heating for 10 hours. After allowing to cool, the reaction solution was filtrated and the filtrate was concentrated under reduced pressure. The reaction mixture was washed three times with methanol. The precipitate was dissolved in toluene, and activated carbon was added to the solution and the resultant mixture was stirred. Thereafter, the obtained mixture was filtrated and the filtrate was concentrated under reduced pressure, thus obtaining 2,7-bis(4,4,5,5-tetramethyl-1,3,2-dioxaborolane-2-yl)-9,9-bis[3-ethoxycarbonyl-4-[2-[2-(2-methoxyethoxy)ethoxy]ethoxy]phenyl]-fluorene (compound D) (11.7 g) represented by the following formula was obtained.

Compound D

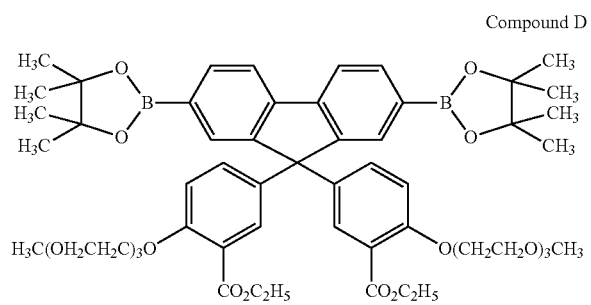

The compound B (0.55 g), the compound D (0.61 g), tetrakistriphenylphosphine palladium (0.01 g), methyltrioctyl ammonium chloride (manufactured by Aldrich Co. LLC., trade name: Aliquat 336 (registered trademark)) (0.20 g), and toluene (10 mL) were added into a flask having a volume of 100 mL whose inner gas was replaced by argon gas, and mixed. The mixture was heated at 105° C. 2M sodium carbonate aqueous solution (6 mL) was added dropwise to the reaction solution, and the resultant solution was refluxed for 8 hours. 4-tert-butylphenylboronic acid (0.01 g) was added to the reaction solution and the resultant solution was refluxed for 6 hours. Subsequently, sodium diethyldithiocarbamate aqueous solution (10 mL, concentration: 0.05 g/mL) was added, and the resultant solution was stirred for 2 hours. The obtained solution was added dropwise to 300 mL of methanol and the obtained mixture was stirred for 1 hour. The deposited precipitate was filtered, dried for 2 hours under reduced pressure, and dissolved in 20 mL of tetrahydrofuran. The obtained solution was added dropwise to a mixed solvent of 120 mL of methanol and 50 mL of acetic acid aqueous solution (3% by weight) and the resultant solution was stirred for 1 hour, and thereafter, the deposited precipitate was filtered. The obtained precipitate was dissolved in 20 mL of tetrahydrofuran. The obtained solution was added dropwise to 200 mL of methanol and the resultant solution was stirred for 30 minutes, and thereafter, the deposited precipitate was filtered to obtain a solid. The obtained solid was dissolved in tetrahydrofuran to obtain a tetrahydrofuran solution. The tetrahydrofuran solution was purified by passing through an alumina column and a silica gel column. The tetrahydrofuran solution recovered from the column was concentrated, and thereafter, the concentrated solution was added dropwise to methanol. A deposited solid was filtrated and the residue was dried, thus obtaining 520 mg of a conjugated compound (hereinafter, referred to as the "conjugated compound P-3").

From the result of NMR measurement, the conjugated compound P-3 has a structural unit represented by the following formula.

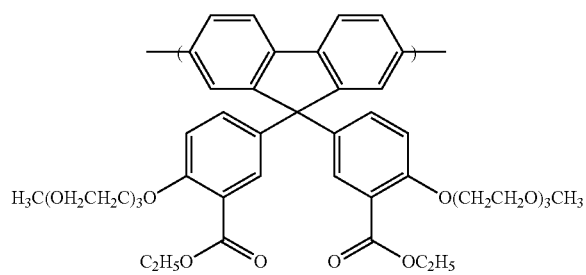

A number average molecular weight of the conjugated compound P-3 in terms of polystyrene was $5.2 \times 10^4$.

Synthesis Example 5

Synthesis of Conjugated Compound P-4

The conjugated compound P-3 (200 mg) was added into a flask having a volume of 100 mL, and the gas in the flask was replaced by nitrogen gas. Tetrahydrofuran (20 mL) and ethanol (20 mL) were added and the mixture was heated to 55° C. An aqueous solution made by dissolving cesium hydroxide (200 mg) in water (2 mL) was added to the mixture and the resultant mixture was stirred for 6 hours at 55° C. The mixture was cooled to the room temperature, and thereafter, the reaction solvent was removed by distillation under reduced pressure. The generated solid was washed with water, and dried under reduced pressure, thus obtaining 150 mg of a conjugated compound having a structural unit represented by the following formula (hereinafter, referred to as "conjugated compound P-4").

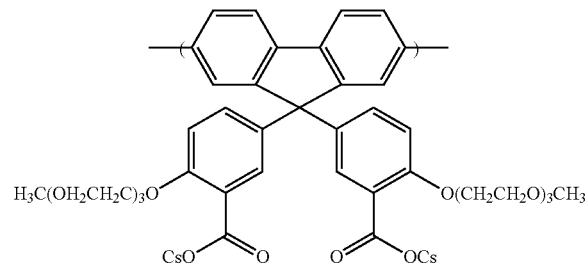

It was confirmed by NMR spectrum in which a signal based on an ethyl group of an ethyl ester part in the conjugated compound P-3 completely disappeared.

Synthesis Example 6

Synthesis of Hole Transport Material A

In a three-necked round bottom flask having a volume of 1 L and equipped with a reflux condenser and an overhead stirrer, 2,7-bis(1,3,2-dioxyborole)-9,9-di(1-octyl)fluorene (3.863 g, 7.283 mmol), N,N-di(p-bromophenyl)-N-(4-(butane-2-yl)phenyl)amine (3.177 g, 6.919 mmol), and di(4-bromophenyl)benzocyclobutane amine (156.3 mg, 0.364 mmol) were added. Subsequently, methyltrioctyl ammonium chloride (manufactured by Aldrich Co. LLC., trade name: Aliquat 336 (registered trademark)) (2.29 g), and 50 mL of toluene were added in this order. $PdCl_2(PPh_3)_2$ catalyst (4.9 mg) was added, and thereafter, the obtained mixture was stirred for 15 minutes in an oil bath having a temperature of 105° C. Sodium carbonate aqueous solution (2.0M, 14 mL) was added to the mixture to obtain a reactant. The reactant was stirred for 16.5 hours in an oil bath having a temperature of 105° C. Subsequently, phenylboronic acid (0.5 g) was added and the resultant reactant was stirred for 7 hours.

A water layer was removed from the reactant and an organic layer was washed with water. The organic layer was returned to the flask, and 0.75 g of sodium diethyldithiocarbamate and 50 mL of water were added into the flask. The reaction solution was stirred for 16 hours in an oil bath having a temperature of 85° C. to obtain a reaction solution. A water layer was removed from the reaction solution and an organic layer was washed three times with water. Thereafter, the organic layer was passed through a column packed with silica gel and basic alumina. An operation to generate precipitate from the obtained toluene solution in methanol was repeated two times. The obtained precipitate was dried at 60° C. under vacuum, thus obtaining 4.2 g of a macromolecular compound being a hole transport material A. A number average molecular weight of the hole transport material A in terms of polystyrene was $4.4 \times 10^4$.

Synthesis Example 7

Synthesis of Hole Transport Material B

Under inert gas atmosphere, 2,7-dibromo-9,9-di(octyl)fluorene (1.4 g, 2.5 mmol), 2,7-bis(4,4,5,5-tetramethyl-1,3,2-dioxaborolan-2-yl)-9,9-di(octyl)fluorene (6.4 g, 10.0 mmol), N,N-bis(4-bromophenyl)-N',N'-bis(4-butylphenyl)-1,4-phenylenediamine (4.1 g, 6 mmol), bis(4-bromophenyl)benzocyclobutene amine (0.6 g, 1.5 mmol), tetraethylammonium hydroxide (1.7 g, 2.3 mmol), palladium acetate (4.5 mg, 0.02 mmol), tri(2-methoxyphenyl)phosphine (0.03 g, 0.08 mmol), and toluene (100 mL) were mixed, and the mixture was stirred for 2 hours with heating at 100° C. Subsequently, phenylboronic acid (0.06 g, 0.5 mmol) was added and the obtained mixture was stirred for 10 hours. After allowing to cool the mixture, a water layer was removed, and sodium diethyldithiocarbamate aqueous solution was added. After stirring the mixture, an aqueous layer was removed, and an organic layer was washed with water and further washed with acetic acid aqueous solution (3% by weight). When the organic layer wad poured into methanol, precipitate was generated. The precipitate was filtrated, and the residue was dissolved again in toluene. Thereafter, the solution was passed through a silica gel column and an alumina column. The eluted toluene solution was recovered. When the recovered eluted toluene solution was poured into methanol, precipitate was generated. After filtrating the precipitate, the precipitate was dried at 50° C. under vacuum, thus obtaining a macromolecular compound being a hole transport material (12.1 g). According to gel permeation chromatography measurement, a weight average molecular weight of the obtained hole transport material in terms of polystyrene was $3.0 \times 10^5$, and a molecular weight distribution index (Mw/Mn) was 3.1.

The hole transport material B is a copolymer having a structural unit represented by the following formula:

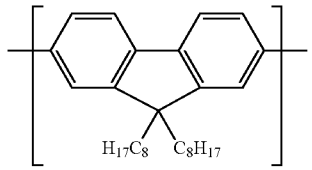

a structural unit represented by the following formula:

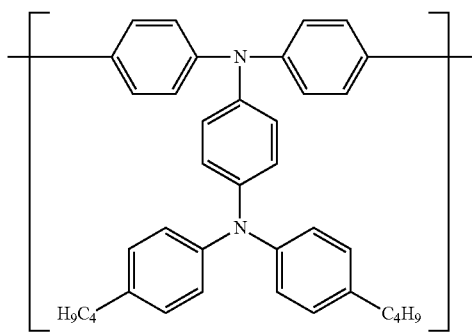

and a structural unit represented by the following formula:

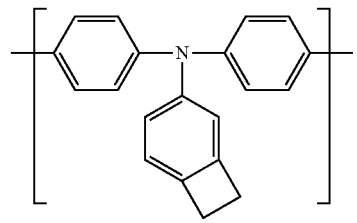

in a molar ratio of 62.5:30:7.5 (a theoretical value from the amount of fed raw materials) in the order of description.

Synthesis Example 8

Synthesis of Light-Emitting Material B

Under inert gas atmosphere, 2,7-dibromo-9,9-di(octyl)fluorene (9.0 g, 16.4 mmol), N,N'-bis(4-bromophenyl)-N,N'-bis(4-tert-butyl-2,6-dimethylphenyl)1,4-phenylenediamine (1.3 g, 1.8 mmol), 2,7-bis(4,4,5,5-tetramethyl-1,3,2-dioxaborolan-2-yl)-9,9-di(4-hexylphenyl)fluorene (13.4 g, 18.0 mmol), tetraethylammonium hydroxide (43.0 g, 58.3 mmol), palladium acetate (8 mg, 0.04 mmol), tri(2-methoxyphenyl)phosphine (0.05 g, 0.1 mmol), and toluene (200 mL) were mixed, and the mixture was stirred for 8 hours with heating at 90° C. Subsequently, phenylboronic acid (0.22 g, 1.8 mmol) was added and the obtained mixture was stirred for 14 hours. After allowing to cool the mixture, a water layer was removed, and sodium diethyldithiocarbamate aqueous solution was added. After stirring the mixture, an aqueous layer was removed, and an organic layer was washed with water and further washed with acetic acid aqueous solution (3% by weight). When the organic layer was poured into methanol, precipitate was generated. The precipitate was filtrated, and the residue was dissolved again in toluene. Thereafter, when the solution was passed through a silica gel column and an alumina column, precipitate was generated. The eluted toluene solution containing the precipitate was recovered. When the recovered eluted toluene solution was poured into methanol, precipitate was generated. The precipitate was dried at 50° C. under vacuum, thus obtaining a macromolecular compound being the light-emitting material (12.5 g). According to gel permeation chromatography, a weight average molecular weight of the obtained light-emitting material in terms of polystyrene was $3.1 \times 10^5$, and a molecular weight distribution index (Mw/Mn) was 2.9.

The light-emitting material B is a copolymer having a structural unit represented by the following formula:

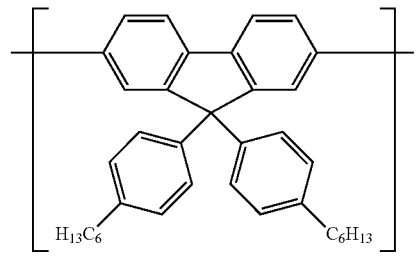

a structural unit represented by the following formula:

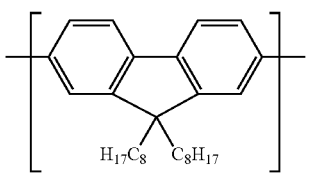

and a structural unit represented by the following formula:

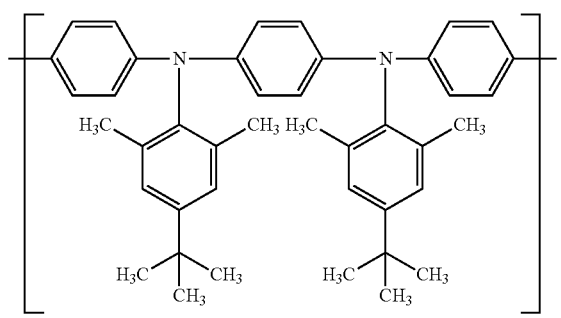

in a molar ratio of 50:45:5 (a theoretical value from the amount of fed raw materials) in the order of description.

Example 1

Manufacture of Light-Emitting Device k-1

On an ITO film that is formed on the glass substrate as an anode, 0.5 mL of poly(3,4-ethylenedioxythiophene)/polystyrene sulfonic acid (manufactured by H.C. Starck GmbH, PEDOT:PSS solution, trade name: CLEVIOS (registered trademark) P VP AI 4083) being a hole injection material solution was applied, and then a film was made so as to be a thickness of 70 nm by a spin coating method. The obtained glass substrate was heated in the air for 10 minutes at 200° C., and thereafter, the glass substrate was allowed to naturally cool to the room temperature, thus obtaining a glass substrate A over which a hole injection layer was formed.

5.2 mg of the hole transport material A obtained in synthesis example 6 and 1 mL of xylene were mixed to prepare a composition for the hole transport layer containing 0.6% by weight of the hole transport material A.

The composition for the hole transport layer was applied by the spin coating method onto the glass substrate A over which the hole injection layer was formed, thus forming a coating film having a thickness of 25 nm. The glass substrate over which the coating film was formed was heated under nitrogen atmosphere for 20 minutes at 200° C. to insolubilize the coating film, and thereafter, the glass substrate was allowed to naturally cool to the room temperature, thus obtaining a glass substrate B over which a hole transport layer was formed.

A light-emitting material A (manufactured by Sumation Co., Ltd., trade name: BP 361) (11.3 mg) and 1 mL of xylene were mixed to prepare a composition for the light-emitting layer containing 1.3% by weight of the light-emitting material.

The composition for the light-emitting layer was applied by the spin coating method onto the glass substrate B over which the hole transport layer was formed, thus forming a coating film having a thickness of 80 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate C over which a light-emitting layer was formed.

The conjugated compound P-4 (2.0 mg) obtained in synthesis example 5 and 1 mL of methanol was mixed to prepare a composition for the electron injection layer containing 0.2% by weight of the conjugated compound P-4.

The composition for the electron injection layer was applied by the spin coating method onto the glass substrate C over which the light-emitting layer was formed, thus forming a coating film having a thickness of 10 nm. The substrate over which the coating film was formed was heated under nitrogen atmosphere for 10 minutes at 130° C. to evaporate the solvent, and thereafter, the substrate was allowed to naturally cool to the room temperature, thus obtaining a glass substrate D over which an electron injection layer was formed.

The silver nano-structure A (10.0 mg) and 1.3 mL of methanol was mixed and stirred for 1 hour to prepare a composition for the cathode.

The composition for the cathode was applied by a casting method onto the glass substrate D over which the electron injection layer was formed, thus forming a coating film having a thickness of 200 nm. The substrate over which the coating film was formed was heated under nitrogen atmosphere for 10 minutes at 130° C. to evaporate the solvent, and thereafter, the substrate was allowed to naturally cool to the room temperature, thus obtaining a glass substrate E over which the cathode was formed.

Finally, the glass substrate E over which the cathode was formed was sealed under nitrogen atmosphere by using a sealing glass and a two-liquid mixing-type epoxy resin (Robnor resins Ltd., trade name: PX681C/NC) to prepare a light-emitting device (hereinafter, referred to as a "light-emitting device k-1").

A forward direction voltage of 14 V was applied to the light-emitting device k-1, and light-emitting brightness of emitted light from a side closer to the anode in a thickness direction of the glass substrate was measured. The light-emitting brightness was 113 cd/m$^2$.

The light-emitting device k-1 emits light also from a side closer to the cathode, because the light-emitting device k-1 is a both-sided light-emitting device. Whole light-emitting brightness of the light-emitting device k-1 in total of light-emitting brightness from the side closer to the anode and the side closer to the cathode was almost two times the value described above.

Example 2

Manufacture of Light-Emitting Device k-2

5.2 mg of the hole transport material B obtained in synthesis example 7 and 1 mL of xylene were mixed to prepare a composition for the hole transport layer containing 0.6% by weight of the hole transport material B.

The composition for the hole transport layer was applied by the spin coating method onto the glass substrate A over which the hole injection layer was formed, thus forming a coating film having a thickness of 33 nm. The glass substrate over which the coating film was formed was heated under nitrogen atmosphere for 20 minutes at 200° C. to insolubilize the coating film, and thereafter, the glass substrate was allowed to naturally cool to the room temperature, thus obtaining a glass substrate F over which a hole transport layer was formed.

The light-emitting material B (11.3 mg) obtained in synthesis example 8 and 1 mL of xylene were mixed to prepare a composition for the light-emitting layer containing 1.3% by weight of the light-emitting material B.

The composition for the light-emitting layer was applied by the spin coating method onto the glass substrate F over which the hole transport layer was formed, thus forming a coating film having a thickness of 99 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate G over which a light-emitting layer was formed.

The conjugated compound P-4 (2.0 mg) obtained in synthesis example 5 and 1 mL of methanol were mixed to prepare a composition for the electron injection layer containing 0.2% by weight of the conjugated compound P-4.

The composition for the electron injection layer was applied by the spin coating method onto the glass substrate G over which the light-emitting layer was formed, thus forming a coating film having a thickness of 10 nm. The substrate over which the coating film was formed was heated under nitrogen atmosphere for 10 minutes at 130° C. to evaporate the solvent, and thereafter, the substrate was allowed to naturally cool to the room temperature, thus obtaining a glass substrate H over which an electron injection layer was formed.

The silver nano-structure A (10.0 mg) and 1.3 mL of water was mixed and stirred for 1 hour to prepare a composition for the cathode.

The composition for the cathode was applied by a casting method onto the glass substrate H over which the electron injection layer was formed, thus forming a coating film having a thickness of 200 nm. The substrate over which the coating film was formed was heated under nitrogen atmosphere for 10 minutes at 130° C. to evaporate the solvent, and thereafter, the substrate was allowed to naturally cool to the room temperature, thus obtaining a glass substrate I over which a cathode was formed.

Finally, the glass substrate I over which the cathode was formed was sealed under nitrogen atmosphere by using the sealing glass and the two-liquid mixing-type epoxy resin (Robnor resins Ltd., trade name: PX681C/NC) to prepare a light-emitting device (hereinafter, referred to as a "light-emitting device k-2").

A forward direction voltage of 14 V was applied to the light-emitting device k-2, and light-emitting brightness of emitted light from a side closer to the anode in a thickness direction of the glass substrate was measured. The light-emitting brightness was 1.8 cd/m$^2$.

The light-emitting device k-2 emits light also from a side closer to the cathode, because the light-emitting device k-2 is a both-sided light-emitting device. Whole light-emitting brightness of the light-emitting device k-2 in total of light-emitting brightness from the side closer to the anode and the side closer to the cathode was almost twice the value described above.

Example 3

Manufacture of Light-Emitting Device k-3

A light-emitting device was prepared in a similar way to Example 2 except that a composition for the electron injection layer made by mixing the conjugated compound P-4 (2.0 mg), cesium hydroxide monohydrate (0.68 mg), and 1 mL of methanol was used instead of the composition for the electron injection layer containing 0.2% by weight of the conjugated compound P-4 made by mixing the conjugated compound P-4 (2.0 mg) and 1 mL of methanol (hereinafter, referred to as a "light-emitting device k-3").

A forward direction voltage of 14 V was applied to the light-emitting device k-3 to which a forward direction voltage of 14 V was applied, and light-emitting brightness of emitted light from a side closer to the anode in a thickness direction of the glass substrate was measured. As a result, the light-emitting brightness was 21 cd/m$^2$. The light-emitting device k-3 emits light also from a side closer to the cathode, because the light-emitting device k-3 is a both-sided light-emitting device. Whole light-emitting brightness of the light-emitting device k-3 in total of light-emitting brightness from the side closer to the anode and the side closer to the cathode was almost twice the value described above.

Comparative Example 1

Manufacture of Light-Emitting Device k-4

A light-emitting device was prepared in a similar way to Example 2 except that the electron injection layer was not formed (hereinafter, referred to a "light-emitting device k-4"). Although a forward direction voltage of 14 V was applied to the light-emitting device k-4, the light-emitting device k-4 did not emit light.

Example 4

Manufacture of Light-Emitting Device k-5

A glass substrate on which an ITO film was formed was inserted into a small-scale vacuum evaporation apparatus (trade name: VPC-260F, manufactured by ULVAC KIKO, Inc.), and an aluminum film is formed onto the ITO film by a vacuum evaporation method so that a thickness of the aluminum film is 100 nm. Thereby, a glass substrate A' over which a cathode was formed was obtained.

The conjugated compound P-2 and methanol was mixed to prepare a composition for the electron injection layer so that a concentration of the conjugated compound P-2 is 0.25% by weight.

The obtained composition for the electron injection layer was applied by the spin coating method onto the cathode over the glass substrate A', thus forming a coating film having a thickness of 10 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate B' over which an electron injection layer was formed.

The light-emitting material (manufactured by Sumation Co., Ltd., trade name: BP 361) and xylene were mixed to prepare a composition for the light-emitting layer containing 1.3% by weight of the light-emitting material.

The composition for the light-emitting layer was applied by the spin coating method onto the glass substrate B' over which the electron injection layer was formed, thus forming a coating film having a thickness of 80 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate C' over which a light-emitting layer was formed.

The silver nano-structure A (10 mg), 0.5 g of methanol, and 1.0 g of poly(3,4-ethylenedioxythiophene)/polystyrene sulfonic acid (manufactured by H. C. Starck GmbH, PEDOT:

PSS solution, trade name: CLEVIOS (registered trademark) P VP Al 4083) were mixed to prepare a composition for a mixed layer j-1 that contains the anode and the hole injection material and that contains 0.67% by weight of the silver nano-structure A.

The composition for the mixed layer j-1 was applied by a casting method onto the glass substrate C' over which the light-emitting layer was formed, thus forming a coating film having a thickness of 1 µm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate D' over which a mixed layer comprising the hole injection layer and the anode was formed.

The silver nano-structure A (10 mg) and 0.5 g of methanol was mixed to prepare a composition for the anode j-2 that contains 2.0% by weight of the silver nano-structure A.

The composition for the anode j-2 was applied by a casting method onto the glass substrate D' over which the mixed layer comprising the hole injection layer and the anode was formed, thus forming a coating film having a thickness of 1 µm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate E' over which an anode was formed.

The glass substrate E' over which the anode was formed was sealed under nitrogen atmosphere by using the sealing glass and the two-liquid mixing-type epoxy resin (Robnor resins Ltd., trade name: PX681C/NC) to prepare a light-emitting device k-5.

A forward direction voltage of 12 V was applied to the light-emitting device k-5, and light-emitting brightness was measured. The light-emitting brightness was 89 cd/m$^2$. The light-emitting device k-5 is a top emission type light-emitting device having an inverted stacked structure prepared by the coating method.

Example 5

Manufacture of Light-Emitting Device k-6

A light-emitting device k-6 was prepared in the same way to Example 1 except that the composition for the anode j-2 was used instead of the composition for the mixed layer j-1 that contains the anode and the hole injection material, and a composition for a mixed layer j-3 that is prepared by mixing the silver nano-structure A (10 mg), 0.5 g of methanol, and 0.5 g of poly(3,4-ethylenedioxythiophene)/polystyrene sulfonic acid (manufactured by H. C. Starck GmbH, PEDOT:PSS solution, trade name: CLEVIOS (registered trademark) P VP Al 4083) containing 1.0% by weight of the silver nano-structure A containing an anode and a hole injection material was used instead of the composition for the anode j-2 in Example 4.

A forward direction voltage of 18 V was applied to the light-emitting device k-6, and light-emitting brightness was measured. The light-emitting brightness was 5.4 cd/m$^2$. The light-emitting device k-6 is a top emission type light-emitting device having an inverted stacked structure prepared by the coating method.

Example 6

Manufacture of Light-Emitting Device k-7

The silver nano-structure A (10 mg) and 0.5 g of methanol were mixed to prepare the composition for the anode j-2 that contains 2.0% by weight of the silver nano-structure A.

The composition for the anode j-2 was applied by the spin coating method onto the glass substrate on which the ITO film was formed, thus forming a coating film having a thickness of 100 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate F' over which an anode was formed.

Poly(3,4-ethylenedioxythiophene)/polystyrene sulfonic acid (manufactured by H. C. Starck GmbH, PEDOT:PSS solution, trade name: CLEVIOS (registered trademark) P VP Al 4083) as the hole injection material was applied by the spin coating method onto the anode of the glass substrate F' over which the anode was formed, thus forming a coating film having a thickness of 120 nm. The substrate over which the coating film was formed was heated under nitrogen atmosphere for 10 minutes at 200° C., and thereafter, the substrate was allowed to naturally cool to the room temperature, thus obtaining a glass substrate G' over which a hole injection layer was formed.

5.2 mg of the hole transport material B and 1 mL of xylene were mixed to prepare the composition for the hole transport layer containing 0.6% by weight of the hole transport material B.

The composition for the hole transport layer was applied by the spin coating method onto the glass substrate G' on which the hole injection layer was formed, thus forming a coating film having a thickness of 33 nm. The glass substrate on which the coating film was formed was heated under nitrogen atmosphere for 20 minutes at 200° C. to insolubilize the coating film, and thereafter, the glass substrate was allowed to naturally cool to the room temperature, thus obtaining a glass substrate H' over which a hole transport layer was formed.

The light-emitting material and xylene were mixed to prepare a composition for the light-emitting layer containing 1.3% by weight of the light-emitting material B.

The composition for light-emitting layer was applied by the spin coating method onto the glass substrate H' over which the hole transport layer was formed, thus forming a coating film having a thickness of 99 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate I' over which a light-emitting layer was formed.

The conjugated compound P-4 and methanol were mixed to prepare a composition for the electron injection layer containing 0.2% by weight of the conjugated compound P-4.

The obtained composition for the electron injection layer was applied by the spin coating method onto the light-emitting layer over the glass substrate I', thus forming a coating film having a thickness of 10 nm. The substrate over which the coating film was formed was heated under nitrogen atmosphere for 15 minutes at 130° C. to evaporate the solvent, and thereafter, the substrate was allowed to naturally cool to the room temperature, thus obtaining a glass substrate J' over which an electron injection layer was formed.

A glass substrate J' on which the electron injection layer was formed was inserted into a small-scale vacuum evaporation apparatus (trade name: VPC-260F, manufactured by ULVAC KIKO, Inc.), and an aluminum layer was formed over the electron injection layer by a vacuum evaporation method so that a thickness of the aluminum film is 100 nm. Thereby, a glass substrate K' over which a cathode was formed was obtained.

The glass substrate K' over which the cathode was formed was sealed under nitrogen atmosphere by using the sealing glass and the two-liquid mixing-type epoxy resin (Robnor resins Ltd., trade name: PX681C/NC) to prepare a light-emitting device k-7.

A forward direction voltage of 12 V was applied to the light-emitting device k-7, and light-emitting brightness was measured. The light-emitting brightness was 1,145 cd/m$^2$. The light-emitting device k-7 is a bottom emission type light-emitting device having a forward stacked structure prepared by the coating method.

It is acknowledged that light transparency of the light-emitting device of the present invention can improved because the light-emitting device comprises electrodes having high conductivity and high transparency even in the case of thin thickness of the electrode, and characteristics such as light-emitting brightness of the light-emitting device can be improved because the electron injection layer contains the organic compound having at least one of the ionic group and the polar group.

Similarly, it is acknowledged that light transparency of the photovoltaic cell can be improved because the photovoltaic cell comprises electrodes having high transparency, and characteristics such as photovoltaic efficiency can be improved because the electron injection layer contains the organic compound having at least one of the ionic group and the polar group.

In addition, it is acknowledged that at least one of the cathode, the anode, and the electron injection layer further contains an ionic compound in addition to the organic compound having at least one of the ionic group and the polar group, and thereby the electron injection characteristic can be improved, and as a result, characteristics of the light-emitting device and the photovoltaic cell can further be improved.

With method for manufacturing of the present invention, a formation step of the cathode following the forming step of an electron injection layer is formed by a convenient coating method that can be performed under air atmosphere. Since these steps can be continuously performed, the method for manufacturing can be more simplified, and the light-emitting device and the photovoltaic cell having more excellent characteristics can be manufactured in higher productivity.

As described above, the present invention provides extremely significant contribution to the light-emitting device, the photovoltaic cell, and the methods for manufacturing thereof.

EXPLANATIONS OF LETTERS OR NUMERALS 10 light-emitting device, photovoltaic cell
20 substrate
22 first substrate
24 second substrate
32 anode
34 cathode
42a hole injection layer
42b hole transport layer
44 electron injection layer
50 light-emitting layer
60 layered structure body
70 charge separation layer
72 electron donor layer
74 electron acceptor layer

The invention claimed is:

1. A light-emitting device comprising:
  a cathode, an anode, a light-emitting layer interposed between the cathode and the anode, and an electron injection layer provided between the cathode and the light-emitting layer and connected to the cathode, wherein
  at least one of the cathode and the anode comprises a conductive material having an aspect ratio of 1.5 or more, and
  the electron injection layer comprises an organic compound having at least one of an ionic group and a polar group.

2. The light-emitting device according to claim 1, wherein the light-emitting device further comprises a substrate, and the cathode, the electron injection layer, the light-emitting layer and the anode are stacked on the substrate in this order such that the cathode is closer to the substrate.

3. The light-emitting device according to claim 1, wherein the cathode has optical transparency.

4. The light-emitting device according to claim 1, wherein the conductive material contains a material selected from the group consisting of a metal, a metal oxide, a carbon material, and combinations thereof.

5. The light-emitting device according to claim 1, wherein the ionic group is at least one group selected from the group consisting of:
  a group represented by formula: —SM, a group represented by formula: —C(=O)SM, a group represented by formula: —CS$_2$M, a group represented by formula: —OM, a group represented by formula: —CO$_2$M, a group represented by formula: —NM$_2$, a group represented by formula: —NRM, a group represented by formula: —PO$_3$M, a group represented by formula: —OP(=O)(OM)$_2$, a group represented by formula: —P(=O)(OM)$_2$, a group represented by formula: —C(=O)NM$_2$, a group represented by formula: —C(=O)NRM, a group represented by formula: —C(=S)NRM, a group represented by formula: —C(=S)NM$_2$, a group represented by formula: —B(OM)$_2$, a group represented by formula: —BR$_3$M, a group represented by formula: —B(OR)$_3$M, a group represented by formula: —SO$_3$M, a group represented by formula: —SO$_2$M, a group represented by formula: —NRC(=O)OM, a group represented by formula: —NRC(=O)SM, a group represented by formula: —NRC(=S)OM, a group represented by formula: —NRC(=S)SM, a group represented by formula: —OC(=O)NM$_2$, a group represented by formula: —OC(=O)NRM, a group represented by formula: —OC(=S)NM$_2$, a group represented by formula: —OC(=S)NRM, a group represented by formula: —SC(=O)NM$_2$, a group represented by formula: —SC(=O)NRM, a group represented by formula: —SC(=S)NM$_2$, a group represented by formula: —SC(=S)NRM, a group represented by formula: —NRC(=O)NM$_2$, a group represented by formula: —NRC(=O)NRM, a group represented by formula: —NRC(=S)NM$_2$, a group represented by formula: —NRC(=S)NRM, a group represented by formula: —NR$_3$M', a group represented by formula: —PR$_3$M', a group represented by formula: —OR$_2$M', a group represented by formula: —SR$_2$M', a group represented by formula: —IRM', a group represented by eliminating a hydrogen atom from an aromatic ring selected from aromatic compounds represented by following formula (n-1) to formula (n-13), wherein R represents a hydrogen atom or a hydrocarbyl group optionally having a substituent, M represents a metal cation or an ammonium cation that may have a substituent, and M' represents an anion:

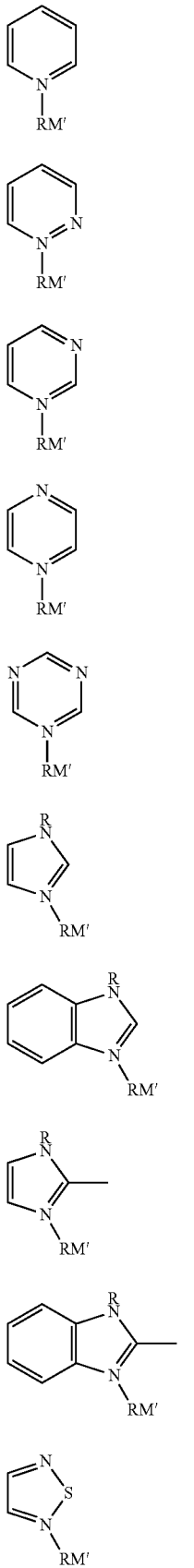

(n-1)
(n-2)
(n-3)
(n-4)
(n-5)
(n-6)
(n-7)
(n-8)
(n-9)
(n-10)

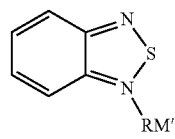

(n-11)

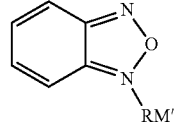

(n-12)

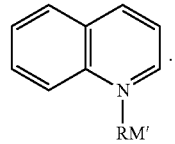

(n-13)

6. The light-emitting device according to claim 1, wherein the polar group is at least one group selected from the group consisting of a carboxy group, a sulfo group, a hydroxy group, a mercapto group, an amino group, a hydrocarbylamino group, a cyano group, a pyrrolidonyl group, a monovalent heterocyclic group and a group represented by following formula (I) to formula (IX):

$$—O—(R'O)_m—R''  \quad (I)$$

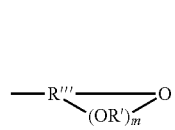

$$—S—(R'S)_q—R''  \quad (III)$$

$$—C(=O)—(R'—C(=O))_q—R''  \quad (IV)$$

$$—C(=S)—(R'—C(=S))_q—R''  \quad (V)$$

$$—N\{(R')_qR''\}_2  \quad (VI)$$

$$—C(=O)O—(R'—C(=O)O)_q—R''  \quad (VII)$$

$$—C(=O)—O—(R'O)_q—R''  \quad (VIII)$$

$$—NHC(=O)—(R''NHC(=O))_q—R''  \quad (IX)$$

wherein, in formula (I) to formula (IX),
R' represents a hydrocarbylene group optionally having a substituent,
R" represents a hydrogen atom, a hydrocarbyl group optionally having a substituent, a carboxy group, a sulfo group, a hydroxy group, a mercapto group, an amino group, a group represented by formula: —$NR^c_2$, a cyano group, or a group represented by formula: —C(=O)$NR^c_2$,
R'" represents a trivalent hydrocarbon group optionally having a substituent,
m represents an integer of 1 or more,
q represents an integer of zero or more,
$R^c$ represents an alkyl group having 1 to 30 carbon atoms that may have a substituent, or an aryl group having 6 to 50 carbon atoms that may have a substituent, and
when R', R", and R'" are each plurally present, each R', R", and R'" may be the same as or different from each other.

7. The light-emitting device according to claim 1, wherein the organic compound having at least one of an ionic group and a polar group is a conjugated compound.

8. The light-emitting device according to claim 7, wherein the conjugated compound has a structural unit represented by following formula (X):

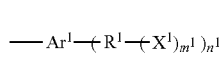
(X)

wherein, in formula (X), $Ar^1$ represents an aromatic group having a valence of $(n^1+1)$; $R^1$ represents a direct bond or a group having a valence of $(m^1+1)$; $X^1$ represents a group having an ionic group or a polar group; $m^1$ and $n^1$ are each independently an integer of 1 or more; when $R^1$ is a direct bond, $m^1$ is 1; when $R^1$, $X^1$ and $m^1$ are each plurally present, each $R^1$, $X^1$, and $m^1$ may be the same as or different from each other, or a structural unit represented by following formula (XI):

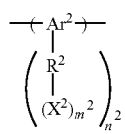
(XI)

wherein, in formula (XI), $Ar^2$ represents an aromatic group having a valence of $(n^2+2)$; $R^2$ represents a direct bond or a group having a valence of $(m^2+1)$; $X^2$ represents a group having an ionic group or a polar group; $m^2$ and $n^2$ are each independently an integer of 1 or more; when $R^2$ is a direct bond, $m^2$ is 1; when $R^2$, $X^2$ and $m^2$ are each plurally present, each $R^2$, $X^2$ and $m^2$ may be the same as or different from each other, or both of structural units represented by formula (X) and formula (XI).

9. The light-emitting device according to claim 8, wherein $Ar^1$ represents a group optionally having a substituent and represented by eliminating $(n^1+1)$ hydrogen atoms from an aromatic ring of aromatic compounds represented by any one of the following formulae; and $Ar^2$ represents a group optionally having a substituent and represented by eliminating $(n^2+2)$ hydrogen atoms from an aromatic ring of aromatic compounds represented by any one of the following formulae:

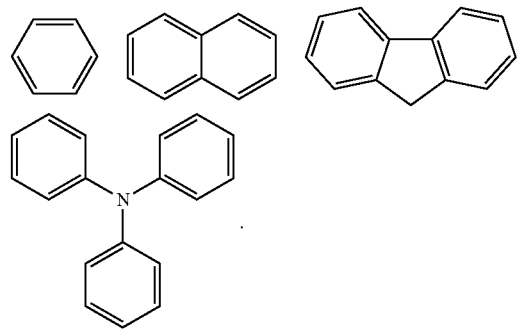

10. The light-emitting device according to claim 1, wherein at least one of the cathode, the anode, and the electron injection layer contains an ionic compound.

11. The light-emitting device according to claim 10, wherein the ionic compound is a compound having a structure represented by following formula (h-1):

(h-1)

wherein, in formula (h-1), $M^{m+}$ represents a metal cation; $X^{m'-}$ represents an anion; a and b are each independently an integer of 1 or more; when $M^{m+}$ and $X^{m'-}$ are each plurally present, each $M^{m+}$ and $X^{m'-}$ may be the same as or different from each other.

12. The light-emitting device according to claim 10, wherein the electron injection layer comprises the ionic compound, and the ratio of the ionic compound in the electron injection layer is 0.1 parts by weight or more and 100 parts by weight or less, with respect to 100 parts by weight of the organic compound having at least one of an ionic group and polar group.

13. A photovoltaic cell comprising:
a cathode, an anode, a charge separating layer interposed between the cathode and the anode, and an electron injection layer provided between the cathode and the charge separating layer and connected to the cathode, wherein
at least one of the cathode and the anode comprises a conductive material having an aspect ratio of 1.5 or more, and
the electron injection layer comprises an organic compound having at least one of an ionic group and a polar group.

* * * * *